United States Patent [19]
Pinilla et al.

[11] Patent Number: 5,556,762
[45] Date of Patent: Sep. 17, 1996

[54] SCANNING SYNTHETIC PEPTIDE COMBINATORIAL LIBRARIES: OLIGOPEPTIDE MIXTURE SETS HAVING A ONE PREDETERMINED RESIDUE AT A SINGLE, PREDETERMINED POSITION, METHODS OF MAKING AND USING THE SAME

[75] Inventors: Clemencia Pinilla; Jon R. Appel, Jr., both of Cardiff; Richard A. Houghten, Solana Beach, all of Calif.

[73] Assignee: Houghten Pharmaceutical Inc., San Diego, Calif.

[21] Appl. No.: 943,709

[22] Filed: Sep. 11, 1992

Related U.S. Application Data

[63] Continuation-in-part of Ser. No. 797,551, Nov. 19, 1991, abandoned, which is a continuation-in-part of Ser. No. 701,658, May 16, 1991, abandoned, which is a continuation-in-part of Ser. No. 617,023, Nov. 21, 1990, abandoned.

[51] Int. Cl.⁶ ............................................. G01N 33/53
[52] U.S. Cl. ...................... 435/7.21; 435/7.1; 435/7.2; 436/501; 436/518; 530/333; 530/334
[58] Field of Search ............................... 435/7.2, 7.21, 435/7.1; 436/501, 536, 86; 530/333, 345

[56] References Cited

U.S. PATENT DOCUMENTS

| | | | |
|---|---|---|---|
| 3,544,404 | 12/1970 | Johnson et al. | 156/148 |
| 4,226,857 | 10/1980 | Momany | 424/177 |
| 4,282,143 | 8/1981 | Sarantakis | 260/112.55 |
| 4,304,692 | 12/1981 | Hughes et al. | 260/8 |
| 4,483,964 | 11/1984 | Urdea et al. | 525/54.23 |
| 4,507,433 | 3/1985 | Miller et al. | 525/54.11 |
| 4,631,211 | 12/1986 | Houghten | 428/35 |
| 4,708,871 | 11/1987 | Geysen | 424/88 |
| 5,010,175 | 4/1991 | Rutter et al. | 530/334 |
| 5,182,366 | 1/1993 | Huebner et al. | 530/334 |
| 5,194,392 | 3/1993 | Geysen | 436/518 |

FOREIGN PATENT DOCUMENTS

| | | |
|---|---|---|
| 8403506 | 9/1984 | WIPO. |
| 8403564 | 9/1984 | WIPO. |
| 8600991 | 2/1986 | WIPO. |

OTHER PUBLICATIONS

Pinilla et al BioTechniques 13 #6 (Dec. 1992) "Rapid Identification at High Affinity Peptide Ligands Using Positional Scanning Synthetic Peptide Combinatorial Libraries".
Geysen et al., *Proc. Natl. Acad. Sci. USA*, 81:3998–4002 (Jul., 1984).
Geysen et al., *Proc. Natl. Acad. Sci. USA*, 82:178–182 (Jan., 1985).
Geysen et al., "The Delineation of Peptides Able to Mimic Assembled Epitopes", in 1986 Synthetic Peptides as Antigens, (CIBA Foundation Symposium 119), pp. 130–149 (1986)–[1986a].
Geysen et al., *Molecular Immunology*, 23(7):709–715 (1986)–[1986b].
Geysen et al., *J. Immunol. Meth.*, 102:259–274 (1987).
Mason et al., "Diversity of the Antibody Response", in Vaccines 86, pp. 97–103 (1986).
Merrifield, *J. Amer. Chem. Soc.*, 85(14); 2149–2154 (Jul. 20, 1963).
Rodda et al., *Molecular Immunology*, 23(6):603–610 (1986).
Schoofs et al., *J. Immunol.*, 140(2):611–616 (Jan. 15, 1988).
Furka et al., (1988, 14th International Congress of Biochemistry, vol. 5, Abstract FR:013).
Houghten, *Proc. Natl. Acad. Sci.*, 82:5131–5135 (1985).
Houghten, et al., *Biotechniques*, 4(6):522–528 (1986).
Devlin et al., *Science*, 249:404–405 (1990).
Scott et al., *Science*, 249:386–390 (1990).
Fodor et al., *Science*, 251:767–773 (1991).
Houghten et al., *Vaccines 1986*, pp. 21–25 (1987).
Houghten et al., *Nature*, 354:84–86 (Nov. 7, 1991).
Lam et al., *Letters to Nature*, 354:82 (Nov. 7, 1991).
Furka et al, *Int. J. Peptide Protein Res.*, 37:487–493 (1991).
Van der Zee et al., *Eur. J. Immunol.*, 19:43–47 (1989).
Merrifield, *Angew. Chem. Int. Ed. Engl.*, 24:799 (Oct. 1985).
Abstract No. 288, *Xth International Symposium on Medicinal Chemistry*, Budapest, Hungary, Aug. 15–18, 1988, p. 168.

*Primary Examiner*—Margaret Parr

*Assistant Examiner*—Lora M. Green
*Attorney, Agent, or Firm*—Welsh & Katz, Ltd.

[57] ABSTRACT

Synthetic peptide combinatorial libraries (sets) having a single, predetermined amino acid residue at a single, predetermined oligopeptide chain position and mixtures of amino acid residues at the other chain positions are disclosed, as are their processes of synthesis and use in determining the amino acid residue sequence of an oligopeptide ligand that binds to an acceptor molecule.

17 Claims, 4 Drawing Sheets

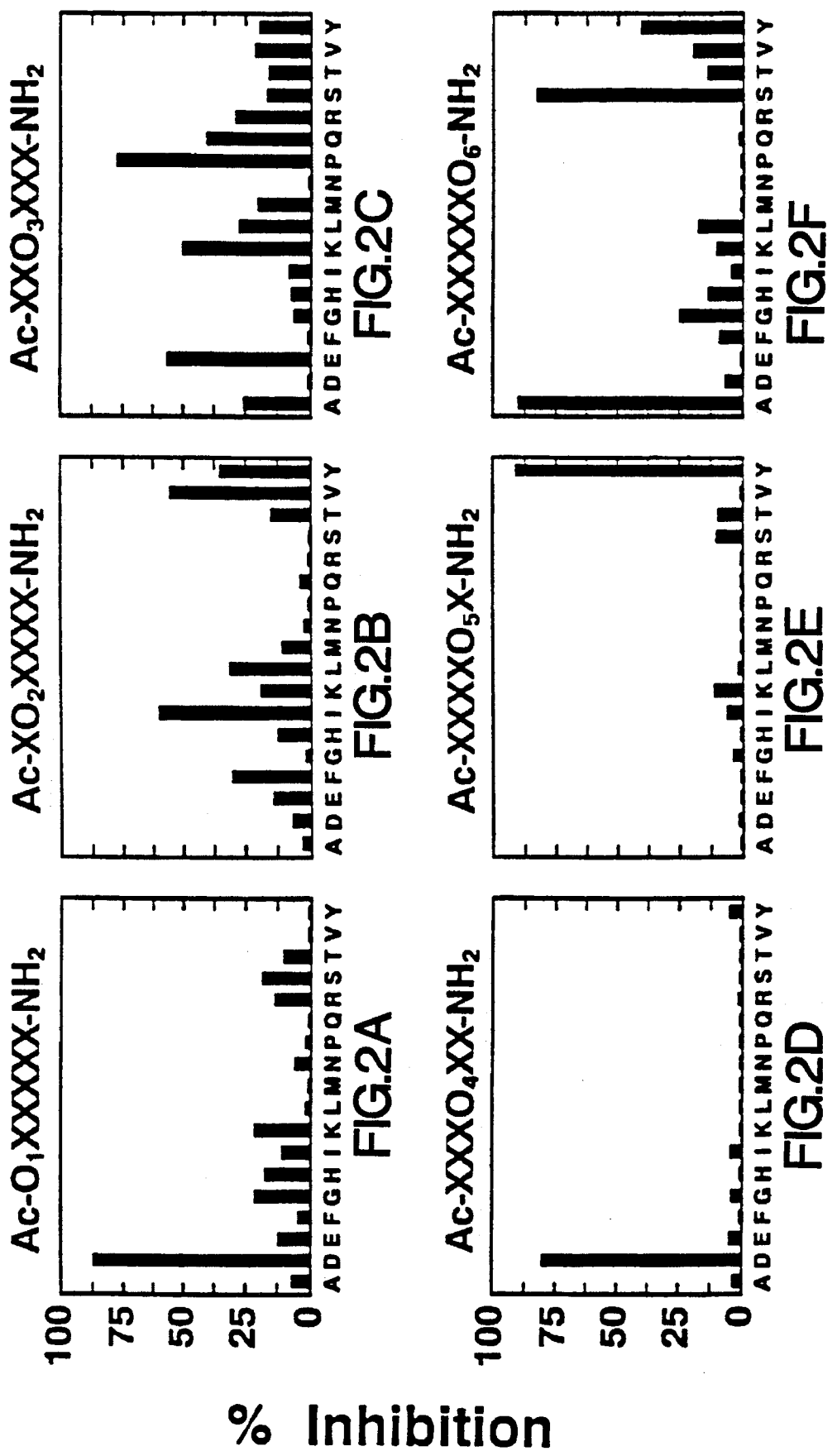

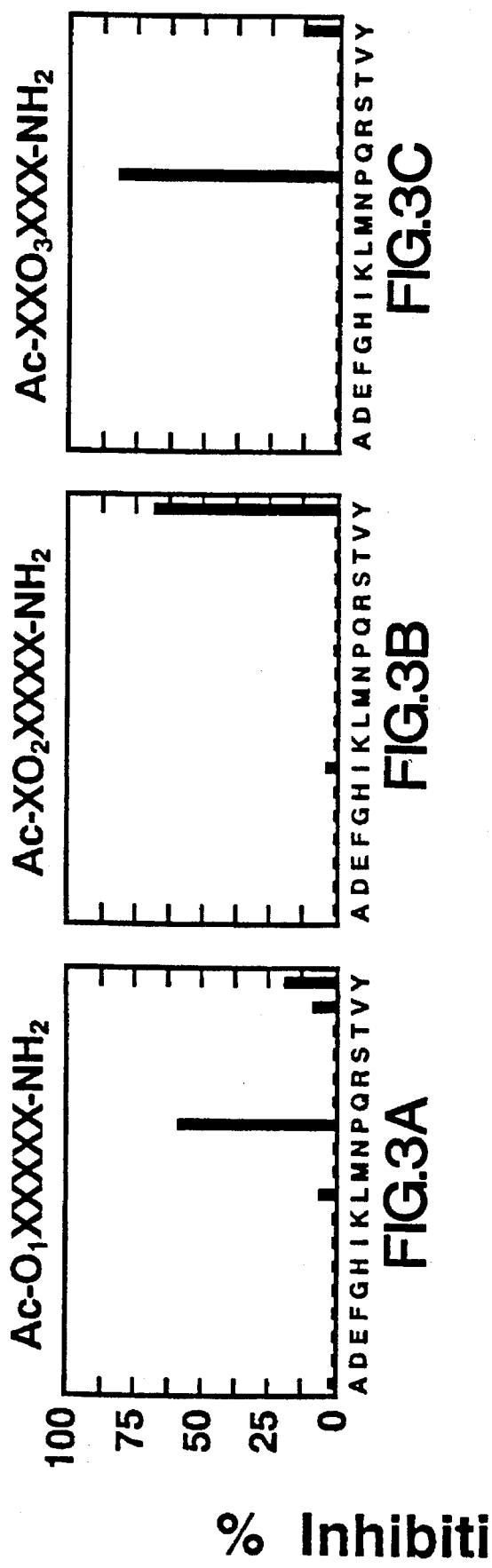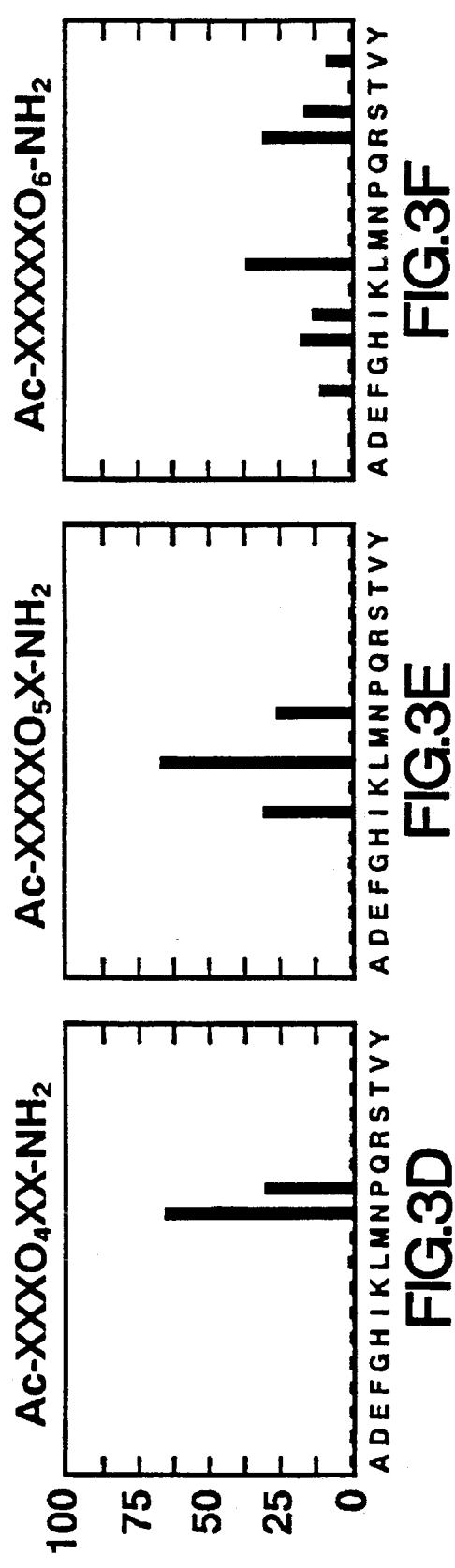

SEQUENCE LISTING ( 1 ) GENERAL INFORMATION:

( i i i ) NUMBER OF SEQUENCES: 119

( 2 ) INFORMATION FOR SEQ ID NO:1:

( i ) SEQUENCE CHARACTERISTICS:
      ( A ) LENGTH: 13 amino acids
      ( B ) TYPE: amino acid
      ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /note="Xaa is Ac—Tyr."

( i x ) FEATURE:
  ( A ) NAME/KEY: Modified-site
  ( B ) LOCATION: 13
  ( D ) OTHER INFORMATION: /note="Xaa is Ser—NH2."

( x i ) SEQUENCE DESCRIPTION: SEQ ID NO:1:

Xaa  Pro  Tyr  Asp  Val  Pro  Asp  Tyr  Ala  Ser  Leu  Arg  Xaa
1                  5                           10

( 2 ) INFORMATION FOR SEQ ID NO:2:

( i ) SEQUENCE CHARACTERISTICS:
    ( A ) LENGTH: 13 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Gly."

( i x ) FEATURE:
    ( A ) NAME/KEY: Modified-site
    ( B ) LOCATION: 13
    ( D ) OTHER INFORMATION: /note="Xaa is Thr—NH2."

( x i ) SEQUENCE DESCRIPTION: SEQ ID NO:2:

Xaa  Ala  Ser  Pro  Tyr  Pro  Asn  Leu  Ser  Asn  Gln  Gln  Xaa
1                  5                           10

( 2 ) INFORMATION FOR SEQ ID NO:3:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:3:

Asp  Val  Pro  Asp  Tyr  Ala
1                  5

( 2 ) INFORMATION FOR SEQ ID NO:4:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:4:

Pro  Tyr  Pro  Asn  Leu  Leu
1                  5

( 2 ) INFORMATION FOR SEQ ID NO:5:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide

```
    ( i x ) FEATURE:
            ( A ) NAME/KEY: Modified-site
            ( B ) LOCATION: 4
            ( D ) OTHER INFORMATION: /note="Xaa is
                    Phe—NH(CH3SCH2CH2)CHCH2OH)."

( x i ) SEQUENCE DESCRIPTION: SEQ ID NO:5:

Tyr  Gly  Gly  Xaa
    1

( 2 ) INFORMATION FOR SEQ ID NO:6:

( i ) SEQUENCE CHARACTERISTICS:
            ( A ) LENGTH: 4 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 4
            ( D ) OTHER INFORMATION: /note="Xaa is
                    Phe—NH[(CH3)2CHCH2]CHCH2OH."

( x i ) SEQUENCE DESCRIPTION: SEQ ID NO:6:

Tyr  Gly  Gly  Xaa
    1

( 2 ) INFORMATION FOR SEQ ID NO:7:

( i ) SEQUENCE CHARACTERISTICS:
            ( A ) LENGTH: 6 amino acids
            ( B ) TYPE: amino acid
            ( D ) TOPOLOGY: linear ( i i ) MOLECULE TYPE: peptide ( i x ) FEATURE:
            ( A ) NAME/KEY: Region
            ( B ) LOCATION: 3
            ( D ) OTHER INFORMATION: /note="Xaa is Phe or Gly."

( i x ) FEATURE:
            ( A ) NAME/KEY: Region
            ( B ) LOCATION: 5
            ( D ) OTHER INFORMATION: /note="Xaa is Phe, Tyr, Met, Leu
                    or Arg."

( i x ) FEATURE:
            ( A ) NAME/KEY: Modified-site
            ( B ) LOCATION: 6
            ( D ) OTHER INFORMATION: /note="Xaa is Arg—NH2, Phe—NH2,
                    Tyr—NH2, Thr—NH2 or Lys—NH2, with Arg—NH2, Phe—NH2
                    and Tyr—NH2 being preferred."

( x i ) SEQUENCE DESCRIPTION: SEQ ID NO:7:

Tyr  Gly  Xaa  Phe  Xaa  Xaa
    1                    5

( 2 ) INFORMATION FOR SEQ ID NO:8:

( i ) SEQUENCE CHARACTERISTICS:
            ( A ) LENGTH: 6 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 6
            ( D ) OTHER INFORMATION: /note="Xaa is Tyr—NH2."
```

( x i ) SEQUENCE DESCRIPTION: SEQ ID NO:8:

Tyr  Gly  Gly  Phe  Met  Xaa
 1                     5

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Arg—NH2."

( x i ) SEQUENCE DESCRIPTION: SEQ ID NO:9:

Tyr  Gly  Gly  Phe  Met  Xaa
 1                     5

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Tyr—NH2."

( x i ) SEQUENCE DESCRIPTION: SEQ ID NO:10:

Tyr  Gly  Gly  Phe  Tyr  Xaa
 1                     5

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Tyr—NH2."

( x i ) SEQUENCE DESCRIPTION: SEQ ID NO:11:

Tyr  Gly  Gly  Phe  Leu  Xaa
 1                     5

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Arg—NH2."

( x i ) SEQUENCE DESCRIPTION: SEQ ID NO:12:

Tyr Gly Gly Phe Leu Xaa
1               5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Tyr—NH2."

( x i ) SEQUENCE DESCRIPTION: SEQ ID NO:13:

Tyr Gly Gly Phe Phe Xaa
1               5

( 2 ) INFORMATION FOR SEQ ID NO:14:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Phe—NH2."

( x i ) SEQUENCE DESCRIPTION: SEQ ID NO:14:

Tyr Gly Gly Phe Met Xaa
1               5

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Tyr—NH2."

( x i ) SEQUENCE DESCRIPTION: SEQ ID NO:15:

Tyr Gly Phe Phe Met Xaa
1               5

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Arg—NH2."

( x i ) SEQUENCE DESCRIPTION: SEQ ID NO:16:

Tyr Gly Gly Phe Phe Xaa
1               5

( 2 ) INFORMATION FOR SEQ ID NO:17:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Phe—NH2."

( x i ) SEQUENCE DESCRIPTION: SEQ ID NO:17:

Tyr Gly Gly Phe Leu Xaa
1               5

( 2 ) INFORMATION FOR SEQ ID NO:18:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Arg—NH2."

( x i ) SEQUENCE DESCRIPTION: SEQ ID NO:18:

Tyr Gly Gly Phe Tyr Xaa
1               5

( 2 ) INFORMATION FOR SEQ ID NO:19:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Tyr—NH2."

( x i ) SEQUENCE DESCRIPTION: SEQ ID NO:19:

Tyr Gly Phe Phe Tyr Xaa
1               5

( 2 ) INFORMATION FOR SEQ ID NO:20:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Tyr—NH2."

( x i ) SEQUENCE DESCRIPTION: SEQ ID NO:20:

Tyr Gly Phe Phe Leu Xaa
1               5

( 2 ) INFORMATION FOR SEQ ID NO:21:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Arg—NH2."

( x i ) SEQUENCE DESCRIPTION: SEQ ID NO:21:

Tyr Gly Phe Phe Met Xaa
1               5

( 2 ) INFORMATION FOR SEQ ID NO:22:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Arg—NH2."

( x i ) SEQUENCE DESCRIPTION: SEQ ID NO:22:

Tyr Gly Phe Phe Leu Xaa
1               5

( 2 ) INFORMATION FOR SEQ ID NO:23:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Arg—NH2."

( x i ) SEQUENCE DESCRIPTION: SEQ ID NO:23:

Tyr Gly Phe Phe Tyr Xaa
1               5

( 2 ) INFORMATION FOR SEQ ID NO:24:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Phe—NH2."

( x i ) SEQUENCE DESCRIPTION: SEQ ID NO:24:

Tyr Gly Gly Phe Phe Xaa
1               5

( 2 ) INFORMATION FOR SEQ ID NO:25:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Phe—NH2."

( x i ) SEQUENCE DESCRIPTION: SEQ ID NO:25:

Tyr Gly Phe Phe Met Xaa
1               5

( 2 ) INFORMATION FOR SEQ ID NO:26:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Arg—NH2."

( x i ) SEQUENCE DESCRIPTION: SEQ ID NO:26:

Tyr Gly Phe Phe Phe Xaa
1               5

( 2 ) INFORMATION FOR SEQ ID NO:27:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Phe—NH2."

( x i ) SEQUENCE DESCRIPTION: SEQ ID NO:27:

Tyr Gly Gly Phe Tyr Xaa
1               5

( 2 ) INFORMATION FOR SEQ ID NO:28:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is Tyr—NH2."

( x i ) SEQUENCE DESCRIPTION: SEQ ID NO:28:

Tyr Gly Phe Phe Phe Xaa
1               5

( 2 ) INFORMATION FOR SEQ ID NO:29:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 6
    ( D ) OTHER INFORMATION: /note="Xaa is Phe—NH2."

( x i ) SEQUENCE DESCRIPTION: SEQ ID NO:29:

Tyr Gly Phe Phe Leu Xaa
1               5

( 2 ) INFORMATION FOR SEQ ID NO:30:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 6
    ( D ) OTHER INFORMATION: /note="Xaa is Phe—NH2."

( x i ) SEQUENCE DESCRIPTION: SEQ ID NO:30:

Tyr Gly Phe Phe Tyr Xaa
1               5

( 2 ) INFORMATION FOR SEQ ID NO:31:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 6
    ( D ) OTHER INFORMATION: /note="Xaa is Phe—NH2."

( x i ) SEQUENCE DESCRIPTION: SEQ ID NO:31:

Tyr Gly Phe Phe Phe Xaa
1               5

( 2 ) INFORMATION FOR SEQ ID NO:32:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Arg."

( i x ) FEATURE:
  ( A ) NAME/KEY: Region
  ( B ) LOCATION: 3
  ( D ) OTHER INFORMATION: /note="Xaa is Met, Leu, Phe or
    Tyr, with Met being preferred."

( i x ) FEATURE:
  ( A ) NAME/KEY: Region
  ( B ) LOCATION: 4
  ( D ) OTHER INFORMATION: /note="Xaa is Phe, Tyr, Arg, Ala,
    Leu, Asn, Gly or Lys, with Phe and Tyr being
    preferred."

( i x ) FEATURE:
  ( A ) NAME/KEY: Modified-site
  ( B ) LOCATION: 6
  ( D ) OTHER INFORMATION: /note="Xaa is Phe—NH2, Arg—NH2,
    Tyr—NH2 or Leu—NH2, with Phe—NH2 being preferred."

( x i ) SEQUENCE DESCRIPTION: SEQ ID NO:32:

Xaa Phe Xaa Xaa Phe Xaa
1         5

( 2 ) INFORMATION FOR SEQ ID NO:33:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /note="Xaa is Ac—Arg."

( i x ) FEATURE:
  ( A ) NAME/KEY: Region
  ( B ) LOCATION: 4
  ( D ) OTHER INFORMATION: /note="Xaa is Phe, Tyr, Arg, Ala,
    Leu, Asn, Gly or Lys, with Phe or Tyr being
    preferred."

( i x ) FEATURE:
  ( A ) NAME/KEY: Modified-site
  ( B ) LOCATION: 6
  ( D ) OTHER INFORMATION: /note="Xaa is Phe—NH2."

( x i ) SEQUENCE DESCRIPTION: SEQ ID NO:33:

Xaa Phe Met Xaa Phe Xaa
1         5

( 2 ) INFORMATION FOR SEQ ID NO:34:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( i x ) FEATURE:
  ( A ) NAME/KEY: Modified-site
  ( B ) LOCATION: 6
  ( D ) OTHER INFORMATION: /note="Xaa is Ala—NH2, Arg—NH2,
    Asn—NH2, Asp—NH2, Gln—NH2, Glu—NH2, Gly—NH2,
    His—NH2, Ile—NH2, Leu—NH2, Lys—NH2, Met—NH2,
    Phe—NH2, Pro—NH2, Ser—NH2, Thr—NH2, Tyr—NH2,
    or Val—NH2."

( i x ) FEATURE:
  ( A ) NAME/KEY: Modified-site
  ( B ) LOCATION: 1
  ( D ) OTHER INFORMATION: /note="Xaa is Ac—Arg."

(x i) SEQUENCE DESCRIPTION: SEQ ID NO:34:

Xaa Phe Met Trp Met Xaa
1                    5

(2) INFORMATION FOR SEQ ID NO:35:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i x) FEATURE:
        (A) NAME/KEY: Modified-site
        (B) LOCATION: 1
        (D) OTHER INFORMATION: /note="Xaa is Ac—Arg."

(i x) FEATURE:
        (A) NAME/KEY: Modified-site
        (B) LOCATION: 6
        (D) OTHER INFORMATION: /note="Xaa is Ala—NH2, Arg—NH2,
            Asn—NH2,, Asp—NH2, Gln—NH2, Glu—NH2, Gly—NH2,
            His—NH2, Ile—NH2, Leu—NH2, Lys—NH2, Met—NH2,
            Phe—NH2, Pro—NH2, Ser—NH2, Thr—NH2, Tyr—NH2,
            or Val—NH2."

(x i) SEQUENCE DESCRIPTION: SEQ ID NO:35:

Xaa Phe Met Trp Val Xaa
1                    5

(2) INFORMATION FOR SEQ ID NO:36:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i x) FEATURE:
        (A) NAME/KEY: Modified-site
        (B) LOCATION: 1
        (D) OTHER INFORMATION: /note="Xaa is Ac—Arg."

(i x) FEATURE:
        (A) NAME/KEY: Modified-site
        (B) LOCATION: 6
        (D) OTHER INFORMATION: /note="Xaa is Ala—NH2, Arg—NH2,
            Asn—NH2, Asp—NH2, Gln—NH2, Glu—NH2, Gly—NH2,
            His—NH2, Ile—NH2, Leu—NH2, Lys—NH2, Met—NH2,
            Phe—NH2, Pro—NH2, Ser—NH2, Thr—NH2, Tyr—NH2,
            or Val—NH2."

(x i) SEQUENCE DESCRIPTION: SEQ ID NO:36:

Xaa Phe Met Trp Gln Xaa
1                    5

(2) INFORMATION FOR SEQ ID NO:37:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i x) FEATURE:
        (A) NAME/KEY: Modified-site
        (B) LOCATION: 1
        (D) OTHER INFORMATION: /note="Xaa is Ac—Arg."

(i x) FEATURE:
        (A) NAME/KEY: Region (B) LOCATION: 5
(D) OTHER INFORMATION: /note="Xaa is Met, Val or Gln."

(ix) FEATURE:
(A) NAME/KEY: Modified-site
(B) LOCATION: 6
(D) OTHER INFORMATION: /note="Xaa is Ala—NH2, Arg—NH2, Asn—NH2, Asp—NH2, Gln—NH2, Glu—NH2, Gly—NH2, His—NH2, Ile—NH2, Leu—NH2, Lys—NH2, Met—NH2, Phe—NH2, Pro—NH2, Ser—NH2, Thr—NH2, Tyr—NH2, or Val—NH2."

(xi) SEQUENCE DESCRIPTION: SEQ ID NO:37:

Xaa Phe Met Trp Xaa Xaa
1                 5

(2) INFORMATION FOR SEQ ID NO:38:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="Xaa is Ac—Arg."

(ix) FEATURE:
(A) NAME/KEY: Modified-site
(B) LOCATION: 6
(D) OTHER INFORMATION: /note="Xaa is Thr—NH2."

(xi) SEQUENCE DESCRIPTION: SEQ ID NO:38:

Xaa Phe Met Trp Met Xaa
1                 5

(2) INFORMATION FOR SEQ ID NO:39:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="Xaa is Ac—Arg."

(ix) FEATURE:
(A) NAME/KEY: Modified-site
(B) LOCATION: 6
(D) OTHER INFORMATION: /note="Xaa is Arg—NH2."

(xi) SEQUENCE DESCRIPTION: SEQ ID NO:39:

Xaa Phe Met Trp Met Xaa
1                 5

(2) INFORMATION FOR SEQ ID NO:40:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1

( D ) OTHER INFORMATION: /note="Xaa is Ac—Arg."

( i x ) FEATURE:
    ( A ) NAME/KEY: Modified-site
    ( B ) LOCATION: 6
    ( D ) OTHER INFORMATION: /note="Xaa is Gly—NH2."

( x i ) SEQUENCE DESCRIPTION: SEQ ID NO:40:

Xaa Phe Met Trp Met Xaa
1                   5

( 2 ) INFORMATION FOR SEQ ID NO:41:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ac—Arg."

( i x ) FEATURE:
        ( A ) NAME/KEY: Modified-site
        ( B ) LOCATION: 6
        ( D ) OTHER INFORMATION: /note="Xaa is Lys—NH2."

( x i ) SEQUENCE DESCRIPTION: SEQ ID NO:41:

Xaa Phe Met Trp Met Xaa
1                   5

( 2 ) INFORMATION FOR SEQ ID NO:42:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ac—Arg."

( i x ) FEATURE:
        ( A ) NAME/KEY: Modified-site
        ( B ) LOCATION: 6
        ( D ) OTHER INFORMATION: /note="Xaa is Ser—NH2."

( x i ) SEQUENCE DESCRIPTION: SEQ ID NO:42:

Xaa Phe Met Trp Met Xaa
1                   5

( 2 ) INFORMATION FOR SEQ ID NO:43:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ac—Arg."

( i x ) FEATURE:
        ( A ) NAME/KEY: Modified-site
        ( B ) LOCATION: 6

( D ) OTHER INFORMATION: /note="Xaa is Leu—NH2."

( x i ) SEQUENCE DESCRIPTION: SEQ ID NO:43:

Xaa Phe Met Trp Met Xaa
1               5

( 2 ) INFORMATION FOR SEQ ID NO:44:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note="Xaa is Ac—Arg."

( i x ) FEATURE:
      ( A ) NAME/KEY: Modified-site
      ( B ) LOCATION: 6
      ( D ) OTHER INFORMATION: /note="Xaa is Asn—NH2."

( x i ) SEQUENCE DESCRIPTION: SEQ ID NO:44:

Xaa Phe Met Trp Met Xaa
1               5

( 2 ) INFORMATION FOR SEQ ID NO:45:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note="Xaa is Ac—Arg."

( i x ) FEATURE:
      ( A ) NAME/KEY: Modified-site
      ( B ) LOCATION: 6
      ( D ) OTHER INFORMATION: /note="Xaa is Ala—NH2."

( x i ) SEQUENCE DESCRIPTION: SEQ ID NO:45:

Xaa Phe Met Trp Met Xaa
1               5

( 2 ) INFORMATION FOR SEQ ID NO:46:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note="Xaa is Ac—Arg."

( i x ) FEATURE:
      ( A ) NAME/KEY: Modified-site
      ( B ) LOCATION: 6
      ( D ) OTHER INFORMATION: /note="Xaa is Met—NH2."

( x i ) SEQUENCE DESCRIPTION: SEQ ID NO:46:

Xaa Phe Met Trp Met Xaa 1               5

(2) INFORMATION FOR SEQ ID NO:47:

(i) SEQUENCE CHARACTERISTICS:
       (A) LENGTH: 6 amino acids
       (B) TYPE: amino acid
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /note="Xaa is Ac—Arg."

(ix) FEATURE:
       (A) NAME/KEY: Modified-site
       (B) LOCATION: 6
       (D) OTHER INFORMATION: /note="Xaa is Tyr—NH2."

(xi) SEQUENCE DESCRIPTION: SEQ ID NO:47:

Xaa  Phe  Met  Trp  Met  Xaa
   1                    5

(2) INFORMATION FOR SEQ ID NO:48:

(i) SEQUENCE CHARACTERISTICS:
       (A) LENGTH: 6 amino acids
       (B) TYPE: amino acid
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /note="Xaa is Ac—Arg."

(ix) FEATURE:
       (A) NAME/KEY: Modified-site
       (B) LOCATION: 6
       (D) OTHER INFORMATION: /note="Xaa is His—NH2."

(xi) SEQUENCE DESCRIPTION: SEQ ID NO:48:

Xaa  Phe  Met  Trp  Met  Xaa
   1                    5

(2) INFORMATION FOR SEQ ID NO:49:

(i) SEQUENCE CHARACTERISTICS:
       (A) LENGTH: 6 amino acids
       (B) TYPE: amino acid
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /note="Xaa is Ac—Arg."

(ix) FEATURE:
       (A) NAME/KEY: Modified-site
       (B) LOCATION: 6
       (D) OTHER INFORMATION: /note="Xaa is Gln—NH2."

(xi) SEQUENCE DESCRIPTION: SEQ ID NO:49:

Xaa  Phe  Met  Trp  Met  Xaa
   1                    5

(2) INFORMATION FOR SEQ ID NO:50:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Arg."

( i x ) FEATURE:
    ( A ) NAME/KEY: Modified-site
    ( B ) LOCATION: 6
    ( D ) OTHER INFORMATION: /note="Xaa is Pro—NH2."

( x i ) SEQUENCE DESCRIPTION: SEQ ID NO:50:

Xaa Phe Met Trp Met Xaa
1               5

( 2 ) INFORMATION FOR SEQ ID NO:51:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Arg."

( i x ) FEATURE:
    ( A ) NAME/KEY: Modified-site
    ( B ) LOCATION: 6
    ( D ) OTHER INFORMATION: /note="Xaa is Val—NH2."

( x i ) SEQUENCE DESCRIPTION: SEQ ID NO:51:

Xaa Phe Met Trp Met Xaa
1               5

( 2 ) INFORMATION FOR SEQ ID NO:52:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Arg."

( i x ) FEATURE:
    ( A ) NAME/KEY: Modified-site
    ( B ) LOCATION: 6
    ( D ) OTHER INFORMATION: /note="Xaa is Trp—NH2."

( x i ) SEQUENCE DESCRIPTION: SEQ ID NO:52:

Xaa Phe Met Trp Met Xaa
1               5

( 2 ) INFORMATION FOR SEQ ID NO:53:

( i ) SEQUENCE CHARACTERISTICS:
    ( A ) LENGTH: 6 amino acids
    ( B ) TYPE: amino acid
    ( D ) TOPOLOGY: linear (i i) MOLECULE TYPE: peptide (i x) FEATURE:
    (A) NAME/KEY: Modified-site
    (B) LOCATION: 1
    (D) OTHER INFORMATION: /note="Xaa is Ac—Arg."

(i x) FEATURE:
    (A) NAME/KEY: Modified-site
    (B) LOCATION: 6
    (D) OTHER INFORMATION: /note="Xaa is Phe—NH2."

(x i) SEQUENCE DESCRIPTION: SEQ ID NO:53:

Xaa  Phe  Met  Trp  Met  Xaa
1                        5

(2) INFORMATION FOR SEQ ID NO:54:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i x) FEATURE:
    (A) NAME/KEY: Modified-site
    (B) LOCATION: 1
    (D) OTHER INFORMATION: /note="Xaa is Ac—Arg."

(i x) FEATURE:
    (A) NAME/KEY: Modified-site
    (B) LOCATION: 6
    (D) OTHER INFORMATION: /note="Xaa is Cys—HN2."

(x i) SEQUENCE DESCRIPTION: SEQ ID NO:54:

Xaa  Phe  Met  Trp  Met  Xaa
1                        5

(2) INFORMATION FOR SEQ ID NO:55:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i x) FEATURE:
    (A) NAME/KEY: Modified-site
    (B) LOCATION: 1
    (D) OTHER INFORMATION: /note="Xaa is Ac—Arg."

(i x) FEATURE:
    (A) NAME/KEY: Modified-site
    (B) LOCATION: 6
    (D) OTHER INFORMATION: /note="Xaa is Ile—NH2."

(x i) SEQUENCE DESCRIPTION: SEQ ID NO:55:

Xaa  Phe  Met  Trp  Met  Xaa
1                        5

(2) INFORMATION FOR SEQ ID NO:56:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i x) FEATURE:
    (A) NAME/KEY: Modified-site
    (B) LOCATION: 1

( D ) OTHER INFORMATION: /note="Xaa is Ac—Arg."

( i x ) FEATURE:
    ( A ) NAME/KEY: Modified-site
    ( B ) LOCATION: 6
    ( D ) OTHER INFORMATION: /note="Xaa is Glu—NH2."

( x i ) SEQUENCE DESCRIPTION: SEQ ID NO:56:

Xaa Phe Met Trp Met Xaa
1               5

( 2 ) INFORMATION FOR SEQ ID NO:57:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ac—Arg."

( i x ) FEATURE:
        ( A ) NAME/KEY: Modified-site
        ( B ) LOCATION: 6
        ( D ) OTHER INFORMATION: /note="Xaa is Asp—NH2."

( x i ) SEQUENCE DESCRIPTION: SEQ ID NO:57:

Xaa Phe Met Trp Met Xaa
1               5

( 2 ) INFORMATION FOR SEQ ID NO:58:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:58:

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

( 2 ) INFORMATION FOR SEQ ID NO:59:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ac—Ile."

( i x ) FEATURE:
        ( A ) NAME/KEY: Region
        ( B ) LOCATION: 4
        ( D ) OTHER INFORMATION: /label=Xaa-4
            / note="Xaa-4 is Phe or Cys."

( i x ) FEATURE:
        ( A ) NAME/KEY: Region
        ( B ) LOCATION: 5
        ( D ) OTHER INFORMATION: /note="Xaa is Phe, Ala Gly or Asp when Xaa-4 is Phe, and Leu, Phe, Met, Gln, Val, Pro, Asn or Asp when Xaa-4 is Cys."

( i x ) FEATURE:
    ( A ) NAME/KEY: Modified-site
    ( B ) LOCATION: 6
    ( D ) OTHER INFORMATION: /note="Xaa is Glu—NH2, Trp—NH2, Thr—NH2, Phe—NH2, Gly—NH2, Asp—NH2, Tyr—NH2, Cys—NH2, Val—NH2, Leu—NH2 or Ala—NH2 when Xaa-4 is Phe, and Gln—NH2, Asp—NH2, Asn—NH2, Met—NH2, Tyr—NH2, Thr—NH2, Ser—NH2, Glu—NH2, Trp—NH2, Val—NH2, Pro—NH2 or Cys—NH2 when Xaa-4 is Cys."

( x i ) SEQUENCE DESCRIPTION: SEQ ID NO:59:

Xaa  Val  Ile  Xaa  Xaa  Xaa
1                             5

( 2 ) INFORMATION FOR SEQ ID NO:60:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Trp."

( i x ) FEATURE:
    ( A ) NAME/KEY: Modified-site
    ( B ) LOCATION: 6
    ( D ) OTHER INFORMATION: /note="Xaa is Ile—NH2."

( x i ) SEQUENCE DESCRIPTION: SEQ ID NO:60:

Xaa  Ile  Gln  Ile  Phe  Xaa
1                             5

( 2 ) INFORMATION FOR SEQ ID NO:61:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Val."

( i x ) FEATURE:
    ( A ) NAME/KEY: Modified-site
    ( B ) LOCATION: 6
    ( D ) OTHER INFORMATION: /note="Xaa is Val—NH2."

( x i ) SEQUENCE DESCRIPTION: SEQ ID NO:61:

Xaa  Ile  Gln  Gln  Phe  Xaa
1                             5

( 2 ) INFORMATION FOR SEQ ID NO:62:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site (B) LOCATION: 1
(D) OTHER INFORMATION: /note="Xaa is Ac—Val."

(ix) FEATURE:
(A) NAME/KEY: Modified-site
(B) LOCATION: 6
(D) OTHER INFORMATION: /note="Xaa is Ile—NH2."

(xi) SEQUENCE DESCRIPTION: SEQ ID NO:62:

Xaa Ile Val Ile Ile Xaa
1               5

(2) INFORMATION FOR SEQ ID NO:63:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="Xaa is Ac—Val."

(ix) FEATURE:
(A) NAME/KEY: Modified-site
(B) LOCATION: 6
(D) OTHER INFORMATION: /note="Xaa is Val—NH2."

(xi) SEQUENCE DESCRIPTION: SEQ ID NO:63:

Xaa Ile Leu Val Phe Xaa
1               5

(2) INFORMATION FOR SEQ ID NO:64:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="Xaa is Ac—Trp."

(ix) FEATURE:
(A) NAME/KEY: Modified-site
(B) LOCATION: 6
(D) OTHER INFORMATION: /note="Xaa is Cys—NH2."

(xi) SEQUENCE DESCRIPTION: SEQ ID NO:64:

Xaa Met Leu Val Ile Xaa
1               5

(2) INFORMATION FOR SEQ ID NO:65:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="Xaa is Ac—Ile."

(ix) FEATURE:
(A) NAME/KEY: Modified-site (B) LOCATION: 6
(D) OTHER INFORMATION: /note="Xaa is Ile—NH2."

(x i) SEQUENCE DESCRIPTION: SEQ ID NO:65:

Xaa Val Asp Gln Ile Xaa
1               5

(2) INFORMATION FOR SEQ ID NO:66:

(i) SEQUENCE CHARACTERISTICS:
(A) LENGTH: 6 amino acids
(B) TYPE: amino acid
(D) TOPOLOGY: linear (i i) MOLECULE TYPE: peptide (i x) FEATURE:
(A) NAME/KEY: Modified-site
(B) LOCATION: 1
(D) OTHER INFORMATION: /note="Xaa is Ac—Val."

(i x) FEATURE:
(A) NAME/KEY: Modified-site
(B) LOCATION: 6
(D) OTHER INFORMATION: /note="Xaa is Val—NH2."

(x i) SEQUENCE DESCRIPTION: SEQ ID NO:66:

Xaa Ile Met Gln Cys Xaa
1               5

(2) INFORMATION FOR SEQ ID NO:67:

(i) SEQUENCE CHARACTERISTICS:
(A) LENGTH: 6 amino acids
(B) TYPE: amino acid
(D) TOPOLOGY: linear (i i) MOLECULE TYPE: peptide (i x) FEATURE:
(A) NAME/KEY: Modified-site
(B) LOCATION: 1
(D) OTHER INFORMATION: /note="Xaa is Ac—Ile."

(i x) FEATURE:
(A) NAME/KEY: Modified-site
(B) LOCATION: 6
(D) OTHER INFORMATION: /label=Xaa—NH2
/ note="Xaa—NH2 is Ala—NH2, Arg—NH2, Asn—NH2,
Asp—NH2, Gln—NH2, Glu—NH2, Gly—NH2, His—NH2,
Ile—NH2, Leu—NH2, Lys—NH2, Met—NH2, Phe—NH2,
Pro—NH2, Ser—NH2, Thr—NH2, Tyr—NH2 or Val—NH2."

(x i) SEQUENCE DESCRIPTION: SEQ ID NO:67:

Xaa Val Ile Cys Leu Xaa
1               5

(2) INFORMATION FOR SEQ ID NO:68:

(i) SEQUENCE CHARACTERISTICS:
(A) LENGTH: 6 amino acids
(B) TYPE: amino acid
(D) TOPOLOGY: linear (i i) MOLECULE TYPE: peptide (i x) FEATURE:
(A) NAME/KEY: Modified-site
(B) LOCATION: 1
(D) OTHER INFORMATION: /note="Xaa is Ac—Ile."

(i x) FEATURE:
(A) NAME/KEY: Modified-site
(B) LOCATION: 6

( D ) OTHER INFORMATION: /label=Xaa—NH2
/ note="Xaa—NH2 is Ala—NH2, Arg—NH2, Asn—NH2,
Asp—NH2, Gln—NH2, Glu—NH2, Gly—NH2, His—NH2,
Ile—NH2, Leu—NH2, Lys—NH2, Met—NH2, Phe—NH2,
Pro—NH2, Ser—NH2, Thr—NH2, Tyr—NH2 or Val—NH2."

( x i ) SEQUENCE DESCRIPTION: SEQ ID NO:68:

Xaa Val Ile Cys Phe Xaa
1               5

( 2 ) INFORMATION FOR SEQ ID NO:69:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="Xaa is Ac—Ile."

( i x ) FEATURE:
( A ) NAME/KEY: Modified-site
( B ) LOCATION: 6
( D ) OTHER INFORMATION: /label=Xaa—NH2
/ note="Xaa—NH2 is Ala—NH2, Arg—NH2, Asn—NH2,
Asp—NH2, Gln—NH2, Glu—NH2, Gly—NH2, His—NH2,
Ile—NH2, Leu—NH2, Lys—NH2, Met—NH2, Phe—NH2,
Pro—NH2, Ser—NH2, Thr—NH2, Tyr—NH2 or Val—NH2."

( x i ) SEQUENCE DESCRIPTION: SEQ ID NO:69:

Xaa Val Ile Cys Met Xaa
1               5

( 2 ) INFORMATION FOR SEQ ID NO:70:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="Xaa is Ac—Ile."

( i x ) FEATURE:
( A ) NAME/KEY: Modified-site
( B ) LOCATION: 6
( D ) OTHER INFORMATION: /label=Xaa—NH2
/ note="Xaa—NH2 is Ala—NH2, Arg—NH2, Asn—NH2,
Asp—NH2, Gln—NH2, Glu—NH2, Gly—NH2, His—NH2,
Ile—NH2, Leu—NH2, Lys—NH2, Met—NH2, Phe—NH2,
Pro—NH2, Ser—NH2, Thr—NH2, Tyr—NH2 or Val—NH2."

( x i ) SEQUENCE DESCRIPTION: SEQ ID NO:70:

Xaa Val Ile Cys Gln Xaa
1               5

( 2 ) INFORMATION FOR SEQ ID NO:71:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:

( A ) NAME/KEY: Modified-site
( B ) LOCATION: 1
( D ) OTHER INFORMATION: /note="Xaa is Ac—Ile."

( i x ) FEATURE:
( A ) NAME/KEY: Modified-site
( B ) LOCATION: 6
( D ) OTHER INFORMATION: /label=Xaa—NH2
/ note="Xaa—NH2 is Ala—NH2, Arg—NH2, Asn—NH2,
Asp—NH2, Gln—NH2, Glu—NH2, Gly—NH2, His—NH2,
Ile—NH2, Leu—NH2, Lys—NH2, Met—NH2, Phe—NH2,
Pro—NH2, Ser—NH2, Thr—NH2, Tyr—NH2 or Val—NH2."

( x i ) SEQUENCE DESCRIPTION: SEQ ID NO:71:

Xaa Val Ile Cys Val Xaa
1               5

( 2 ) INFORMATION FOR SEQ ID NO:72:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="Xaa is Ac—Ile."

( i x ) FEATURE:
( A ) NAME/KEY: Modified-site
( B ) LOCATION: 6
( D ) OTHER INFORMATION: /label=Xaa—NH2
/ note="Xaa—NH2 is Ala—NH2, Arg—NH2, Asn—NH2,
Asp—NH2, Gln—NH2, Glu—NH2, Gly—NH2, His—NH2,
Ile—NH2, Leu—NH2, Lys—NH2, Met—NH2, Phe—NH2,
Pro—NH2, Ser—NH2, Thr—NH2, Tyr—NH2 or Val—NH2."

( x i ) SEQUENCE DESCRIPTION: SEQ ID NO:72:

Xaa Val Ile Cys Pro Xaa
1               5

( 2 ) INFORMATION FOR SEQ ID NO:73:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="Xaa is Ac—Ile."

( i x ) FEATURE:
( A ) NAME/KEY: Modified-site
( B ) LOCATION: 6
( D ) OTHER INFORMATION: /label=Xaa—NH2
/ note="Xaa—NH2 is Ala—NH2, Arg—NH2, Asn—NH2,
Asp—NH2, Gln—NH2, Glu—NH2, Gly—NH2, His—NH2,
Ile—NH2, Leu—NH2, Lys—NH2, Met—NH2, Phe—NH2,
Pro—NH2, Ser—NH2, Thr—NH2, Tyr—NH2 or Val—NH2."

( x i ) SEQUENCE DESCRIPTION: SEQ ID NO:73:

Xaa Val Ile Cys Asn Xaa
1               5

( 2 ) INFORMATION FOR SEQ ID NO:74:

( i ) SEQUENCE CHARACTERISTICS:

(A) LENGTH: 6 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="Xaa is Ac—Ile."

(ix) FEATURE:
(A) NAME/KEY: Modified-site
(B) LOCATION: 6
(D) OTHER INFORMATION: /label=Xaa—NH2
/ note="Xaa—NH2 is Ala—NH2, Arg—NH2, Asn—NH2,
Asp—NH2, Gln—NH2, Glu—NH2, Gly—NH2, His—NH2,
Ile—NH2, Leu—NH2, Lys—NH2, Met—NHw, Phe—NH2,
Pro—NH2, Ser—NH2, Thr—NH2, Tyr—NH2 or Val—NH2."

(xi) SEQUENCE DESCRIPTION: SEQ ID NO:74:

Xaa Val Ile Cys Asp Xaa
1               5

(2) INFORMATION FOR SEQ ID NO:75:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="Xaa is Ac—Ile."

(ix) FEATURE:
(A) NAME/KEY: Modified-site
(B) LOCATION: 6
(D) OTHER INFORMATION: /label=Xaa—NH2
/ note="Xaa—NH2 is Ala—NH2, Arg—NH2, Asn—NH2,
Asp—NH2, Gln—NH2, Glu—NH2, Gly—NH2, His—NH2,
Ile—NH2, Leu—NH2, Lys—NH2, Met—NH2, Phe—NH2,
Pro—NH2, Ser—NH2, Thr—NH2, Tyr—NH2 or Val—NH2."

(xi) SEQUENCE DESCRIPTION: SEQ ID NO:75:

Xaa Val Ile Cys Ser Xaa
1               5

(2) INFORMATION FOR SEQ ID NO:76:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="Xaa is Ac—Ile."

(ix) FEATURE:
(A) NAME/KEY: Modified-site
(B) LOCATION: 6
(D) OTHER INFORMATION: /label=Xaa—NH2
/ note="Xaa—NH2 is Ala—NH2, Arg—NH2, Asn—NH2,
Asp—NH2, Gln—NH2, Glu—NH2, Gly—NH2, His—NH2,
Ile—NH2, Leu—NH2, Lys—NH2, Met—NH2, Phe—NH2,
Pro—NH2, Ser—NH2, Thr—NH2, Tyr—NH2 or Val—NH2."

(xi) SEQUENCE DESCRIPTION: SEQ ID NO:76:

```
Xaa  Val  Ile  Phe  Phe  Xaa
 1                 5
```

(2) INFORMATION FOR SEQ ID NO:77:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="Xaa is Ac—Ile."

(ix) FEATURE:
        (A) NAME/KEY: Modified-site
        (B) LOCATION: 6
        (D) OTHER INFORMATION: /label=Xaa—NH2
            /note="Xaa—NH2 is Ala—NH2, Arg—NH2, Asn—NH2,
            Asp—NH2, Gln—NH2, Glu—NH2, Gly—NH2, His—NH2,
            Ile—NH2, Leu—NH2, Lys—NH2, Met—NH2, Phe—NH2,
            Pro—NH2, Ser—NH2, Thr—NH2, Tyr—NH2 or Val—NH2."

(xi) SEQUENCE DESCRIPTION: SEQ ID NO:77:

```
Xaa  Val  Ile  Phe  Ala  Xaa
 1                 5
```

(2) INFORMATION FOR SEQ ID NO:78:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="Xaa is Ac—Ile."

(ix) FEATURE:
        (A) NAME/KEY: Modified-site
        (B) LOCATION: 6
        (D) OTHER INFORMATION: /label=Xaa—NH2
            /note="Xaa—NH2 is Ala—NH2, Arg—NH2, Asn—NH2,
            Asp—NH2, Gln—NH2, Glu—NH2, Gly—NH2, His—NH2,
            Ile—NH2, Leu—NH2, Lys—NH2, Met—NH2, Phe—NH2,
            Pro—NH2, Ser—NH2, Thr—NH2, Tyr—NH2 or Val—NH2."

(xi) SEQUENCE DESCRIPTION: SEQ ID NO:78:

```
Xaa  Val  Ile  Phe  Gly  Xaa
 1                 5
```

(2) INFORMATION FOR SEQ ID NO:79:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="Xaa is Ac—Ile."

(ix) FEATURE:
        (A) NAME/KEY: Modified-site
        (B) LOCATION: 6
        (D) OTHER INFORMATION: /label=Xaa—NH2

/ note="Xaa—NH2 is Ala—NH2, Arg—NH2, Asn—NH2,
Asp—NH2, Gln—NH2, Glu—NH2, Gly—NH2, His—NH2,
Ile—NH2, Leu—NH2, Lys—NH2, Met—NH2, Phe—NH2,
Pro—NH2, Ser—NH2, Thr—NH2, Tyr—NH2 or Val—NH2."

( x i ) SEQUENCE DESCRIPTION: SEQ ID NO:79:

Xaa Val Ile Phe Asp Xaa
1               5

( 2 ) INFORMATION FOR SEQ ID NO:80:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ac—Ile."

( i x ) FEATURE:
        ( A ) NAME/KEY: Modified-site
        ( B ) LOCATION: 6
        ( D ) OTHER INFORMATION: /note="Xaa is Gln—NH2."

( x i ) SEQUENCE DESCRIPTION: SEQ ID NO:80:

Xaa Val Ile Cys Gln Xaa
1               5

( 2 ) INFORMATION FOR SEQ ID NO:81:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ac—Ile."

( i x ) FEATURE:
        ( A ) NAME/KEY: Modified-site
        ( B ) LOCATION: 6
        ( D ) OTHER INFORMATION: /note="Xaa is Asp—NH2."

( x i ) SEQUENCE DESCRIPTION: SEQ ID NO:81:

Xaa Val Ile Cys Gln Xaa
1               5

( 2 ) INFORMATION FOR SEQ ID NO:82:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ac—Ile."

( i x ) FEATURE:
        ( A ) NAME/KEY: Modified-site
        ( B ) LOCATION: 6
        ( D ) OTHER INFORMATION: /note="Xaa is Asn—NH2."

( x i ) SEQUENCE DESCRIPTION: SEQ ID NO:82:

Xaa  Val  Ile  Cys  Gln  Xaa
1                      5

( 2 ) INFORMATION FOR SEQ ID NO:83:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ac—Ile."

( i x ) FEATURE:
        ( A ) NAME/KEY: Modified-site
        ( B ) LOCATION: 6
        ( D ) OTHER INFORMATION: /note="Xaa is Met—NH2."

( x i ) SEQUENCE DESCRIPTION: SEQ ID NO:83:

Xaa  Val  Ile  Cys  Gln  Xaa
1                      5

( 2 ) INFORMATION FOR SEQ ID NO:84:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ac—Ile."

( i x ) FEATURE:
        ( A ) NAME/KEY: Modified-site
        ( B ) LOCATION: 6
        ( D ) OTHER INFORMATION: /note="Xaa is Tyr—NH2."

( x i ) SEQUENCE DESCRIPTION: SEQ ID NO:84:

Xaa  Val  Ile  Cys  Gln  Xaa
1                      5

( 2 ) INFORMATION FOR SEQ ID NO:85:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ac—Ile."

( i x ) FEATURE:
        ( A ) NAME/KEY: Modified-site
        ( B ) LOCATION: 6
        ( D ) OTHER INFORMATION: /note="Xaa is Thr—NH2."

( x i ) SEQUENCE DESCRIPTION: SEQ ID NO:85:

Xaa  Val  Ile  Cys  Gln  Xaa
1                      5

( 2 ) INFORMATION FOR SEQ ID NO:86:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ac—Ile."

( i x ) FEATURE:
        ( A ) NAME/KEY: Modified-site
        ( B ) LOCATION: 6
        ( D ) OTHER INFORMATION: /note="Xaa is Ser—NH2."

( x i ) SEQUENCE DESCRIPTION: SEQ ID NO:86:

Xaa  Val  Ile  Cys  Gln  Xaa
1                          5

( 2 ) INFORMATION FOR SEQ ID NO:87:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ac—Ile."

( i x ) FEATURE:
        ( A ) NAME/KEY: Modified-site
        ( B ) LOCATION: 6
        ( D ) OTHER INFORMATION: /note="Xaa is Glu—NH2."

( x i ) SEQUENCE DESCRIPTION: SEQ ID NO:87:

Xaa  Val  Ile  Cys  Val  Xaa
1                          5

( 2 ) INFORMATION FOR SEQ ID NO:88:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ac—Ile."

( i x ) FEATURE:
        ( A ) NAME/KEY: Modified-site
        ( B ) LOCATION: 6
        ( D ) OTHER INFORMATION: /note="Xaa is Asp—NH2."

( x i ) SEQUENCE DESCRIPTION: SEQ ID NO:88:

Xaa  Val  Ile  Cys  Val  Xaa
1                          5

( 2 ) INFORMATION FOR SEQ ID NO:89:

( i ) SEQUENCE CHARACTERISTICS:
        ( A ) LENGTH: 6 amino acids ( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="Xaa is Ac—Ile."

( i x ) FEATURE:
( A ) NAME/KEY: Modified-site
( B ) LOCATION: 6
( D ) OTHER INFORMATION: /note="Xaa is Met—NH2."

( x i ) SEQUENCE DESCRIPTION: SEQ ID NO:89:

Xaa Val Ile Cys Val Xaa
1               5

( 2 ) INFORMATION FOR SEQ ID NO:90:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="Xaa is Ac—Ile."

( i x ) FEATURE:
( A ) NAME/KEY: Modified-site
( B ) LOCATION: 6
( D ) OTHER INFORMATION: /note="Xaa is Thr—NH2."

( x i ) SEQUENCE DESCRIPTION: SEQ ID NO:90:

Xaa Val Ile Cys Val Xaa
1               5

( 2 ) INFORMATION FOR SEQ ID NO:91:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="Xaa is Ac—Ile."

( i x ) FEATURE:
( A ) NAME/KEY: Modified-site
( B ) LOCATION: 6
( D ) OTHER INFORMATION: /note="Xaa is Trp—NH2."

( x i ) SEQUENCE DESCRIPTION: SEQ ID NO:91:

Xaa Val Ile Cys Val Xaa
1               5

( 2 ) INFORMATION FOR SEQ ID NO:92:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Ile."

( i x ) FEATURE:
    ( A ) NAME/KEY: Modified-site
    ( B ) LOCATION: 6
    ( D ) OTHER INFORMATION: /note="Xaa is Tyr—NH2."

( x i ) SEQUENCE DESCRIPTION: SEQ ID NO:92:

Xaa Val Ile Cys Val Xaa
1              5

( 2 ) INFORMATION FOR SEQ ID NO:93:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Ile."

( i x ) FEATURE:
    ( A ) NAME/KEY: Modified-site
    ( B ) LOCATION: 6
    ( D ) OTHER INFORMATION: /note="Xaa is Val—NH2."

( x i ) SEQUENCE DESCRIPTION: SEQ ID NO:93:

Xaa Val Ile Cys Val Xaa
1              5

( 2 ) INFORMATION FOR SEQ ID NO:94:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Ile."

( i x ) FEATURE:
    ( A ) NAME/KEY: Modified-site
    ( B ) LOCATION: 6
    ( D ) OTHER INFORMATION: /note="Xaa is Pro—NH2."

( x i ) SEQUENCE DESCRIPTION: SEQ ID NO:94:

Xaa Val Ile Cys Val Xaa
1              5

( 2 ) INFORMATION FOR SEQ ID NO:95:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Ile."

( i x ) FEATURE:
    ( A ) NAME/KEY: Modified-site
    ( B ) LOCATION: 6
    ( D ) OTHER INFORMATION: /note="Xaa is Ser—NH2."

( x i ) SEQUENCE DESCRIPTION: SEQ ID NO:95:

Xaa Val Ile Cys Val Xaa
1                  5

( 2 ) INFORMATION FOR SEQ ID NO:96:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Ile."

( i x ) FEATURE:
    ( A ) NAME/KEY: Modified-site
    ( B ) LOCATION: 6
    ( D ) OTHER INFORMATION: /note="Xaa is Cys—NH2."

( x i ) SEQUENCE DESCRIPTION: SEQ ID NO:96:

Xaa Val Ile Cys Val Xaa
1                  5

( 2 ) INFORMATION FOR SEQ ID NO:97:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Ile."

( i x ) FEATURE:
    ( A ) NAME/KEY: Modified-site
    ( B ) LOCATION: 6
    ( D ) OTHER INFORMATION: /note="Xaa is Asn—NH2."

( x i ) SEQUENCE DESCRIPTION: SEQ ID NO:97:

Xaa Val Ile Cys Val Xaa
1                  5

( 2 ) INFORMATION FOR SEQ ID NO:98:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Ile."

( i x ) FEATURE:
    ( A ) NAME/KEY: Modified-site
    ( B ) LOCATION: 6
    ( D ) OTHER INFORMATION: /note="Xaa is Glu—NH2."

( x i ) SEQUENCE DESCRIPTION: SEQ ID NO:98:

Xaa Val Ile Phe Ala Xaa
1               5

( 2 ) INFORMATION FOR SEQ ID NO:99:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="Xaa is Ac—Ile."

( i x ) FEATURE:
( A ) NAME/KEY: Modified-site
( B ) LOCATION: 6
( D ) OTHER INFORMATION: /note="Xaa is Trp—NH2."

( x i ) SEQUENCE DESCRIPTION: SEQ ID NO:99:

Xaa Val Ile Phe Ala Xaa
1               5

( 2 ) INFORMATION FOR SEQ ID NO:100:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="Xaa is Ac—Ile."

( i x ) FEATURE:
( A ) NAME/KEY: Modified-site
( B ) LOCATION: 6
( D ) OTHER INFORMATION: /note="Xaa is Thr—NH2."

( x i ) SEQUENCE DESCRIPTION: SEQ ID NO:100:

Xaa Val Ile Phe Ala Xaa
1               5

( 2 ) INFORMATION FOR SEQ ID NO:101:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="Xaa is Ac—Ile."

( i x ) FEATURE:
( A ) NAME/KEY: Modified-site
( B ) LOCATION: 6
( D ) OTHER INFORMATION: /note="Xaa is Phe—NH2."

( x i ) SEQUENCE DESCRIPTION: SEQ ID NO:101:

Xaa Val Ile Phe Ala Xaa
1               5

( 2 ) INFORMATION FOR SEQ ID NO:102:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ac—Ile."

( i x ) FEATURE:
        ( A ) NAME/KEY: Modified-site
        ( B ) LOCATION: 6
        ( D ) OTHER INFORMATION: /note="Xaa is Gly—NH2."

( x i ) SEQUENCE DESCRIPTION: SEQ ID NO:102:

Xaa  Val  Ile  Phe  Ala  Xaa
    1                          5

( 2 ) INFORMATION FOR SEQ ID NO:103:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ac—Ile."

( i x ) FEATURE:
        ( A ) NAME/KEY: Modified-site
        ( B ) LOCATION: 6
        ( D ) OTHER INFORMATION: /note="Xaa is Asp—NH2."

( x i ) SEQUENCE DESCRIPTION: SEQ ID NO:103:

Xaa  Val  Ile  Phe  Ala  Xaa
    1                          5

( 2 ) INFORMATION FOR SEQ ID NO:104:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ac—Ile."

( i x ) FEATURE:
        ( A ) NAME/KEY: Modified-site
        ( B ) LOCATION: 6
        ( D ) OTHER INFORMATION: /note="Xaa is Tyr—NH2."

( x i ) SEQUENCE DESCRIPTION: SEQ ID NO:104:

Xaa  Val  Ile  Phe  Ala  Xaa
    1                          5

( 2 ) INFORMATION FOR SEQ ID NO:105:

( i ) SEQUENCE CHARACTERISTICS:
        ( A ) LENGTH: 6 amino acids (B) TYPE: amino acid
(D) TOPOLOGY: linear (i i) MOLECULE TYPE: peptide (i x) FEATURE:
(A) NAME/KEY: Modified-site
(B) LOCATION: 1
(D) OTHER INFORMATION: /note="Xaa is Ac—Ile."

(i x) FEATURE:
(A) NAME/KEY: Modified-site
(B) LOCATION: 6
(D) OTHER INFORMATION: /note="Xaa is Cys—NH2."

(x i) SEQUENCE DESCRIPTION: SEQ ID NO:105:

Xaa Val Ile Phe Asp Xaa
1               5

(2) INFORMATION FOR SEQ ID NO:106:

(i) SEQUENCE CHARACTERISTICS:
(A) LENGTH: 6 amino acids
(B) TYPE: amino acid
(D) TOPOLOGY: linear (i i) MOLECULE TYPE: peptide (i x) FEATURE:
(A) NAME/KEY: Modified-site
(B) LOCATION: 1
(D) OTHER INFORMATION: /note="Xaa is Ac—Ile."

(i x) FEATURE:
(A) NAME/KEY: Modified-site
(B) LOCATION: 6
(D) OTHER INFORMATION: /note="Xaa is Trp—NH2."

(x i) SEQUENCE DESCRIPTION: SEQ ID NO:106:

Xaa Val Ile Phe Asp Xaa
1               5

(2) INFORMATION FOR SEQ ID NO:107:

(i) SEQUENCE CHARACTERISTICS:
(A) LENGTH: 6 amino acids
(B) TYPE: amino acid
(D) TOPOLOGY: linear (i i) MOLECULE TYPE: peptide (i x) FEATURE:
(A) NAME/KEY: Modified-site
(B) LOCATION: 1
(D) OTHER INFORMATION: /note="Xaa is Ac—Ile."

(i x) FEATURE:
(A) NAME/KEY: Modified-site
(B) LOCATION: 6
(D) OTHER INFORMATION: /note="Xaa is Phe—NH2."

(x i) SEQUENCE DESCRIPTION: SEQ ID NO:107:

Xaa Val Ile Phe Asp Xaa
1               5

(2) INFORMATION FOR SEQ ID NO:108:

(i) SEQUENCE CHARACTERISTICS:
(A) LENGTH: 6 amino acids
(B) TYPE: amino acid
(D) TOPOLOGY: linear (i i) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Ile."

( i x ) FEATURE:
    ( A ) NAME/KEY: Modified-site
    ( B ) LOCATION: 6
    ( D ) OTHER INFORMATION: /note="Xaa is Val—NH2."

( x i ) SEQUENCE DESCRIPTION: SEQ ID NO:108:

Xaa Val Ile Phe Asp Xaa
1                 5

( 2 ) INFORMATION FOR SEQ ID NO:109:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Ile."

( i x ) FEATURE:
    ( A ) NAME/KEY: Modified-site
    ( B ) LOCATION: 6
    ( D ) OTHER INFORMATION: /note="Xaa is Leu—NH2."

( x i ) SEQUENCE DESCRIPTION: SEQ ID NO:109:

Xaa Val Ile Phe Asp Xaa
1                 5

( 2 ) INFORMATION FOR SEQ ID NO:110:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Ile."

( i x ) FEATURE:
    ( A ) NAME/KEY: Modified-site
    ( B ) LOCATION: 6
    ( D ) OTHER INFORMATION: /note="Xaa is Ala—NH2."

( x i ) SEQUENCE DESCRIPTION: SEQ ID NO:110:

Xaa Val Ile Phe Asp Xaa
1                 5

( 2 ) INFORMATION FOR SEQ ID NO:111:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Ile."

( i x ) FEATURE:
    ( A ) NAME/KEY: Region
    ( B ) LOCATION: 5
    ( D ) OTHER INFORMATION: /label=Xaa-5
        / note="Xaa-5 is Gln or Val."

( i x ) FEATURE:
    ( A ) NAME/KEY: Modified-site
    ( B ) LOCATION: 6
    ( D ) OTHER INFORMATION: /note="Xaa is Gln—NH2, Asp—NH2,
        Asn—NH2, Met—NH2, Tyr—NH2, Thr—NH2 or Ser—NH2 when
        Xaa-5 is Gln, and Glu—NH2, Asp—NH2, Met—NH2,
        Thr—NH2, Trp—NH2, Tyr—NH2, Val—NH2, Pro—NH2,
        Ser—NH2, Cys—NH2 or Asn—NH2 when Xaa-5 is Val."

( x i ) SEQUENCE DESCRIPTION: SEQ ID NO:111:

Xaa Val Ile Cys Xaa Xaa
1                5

( 2 ) INFORMATION FOR SEQ ID NO:112:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Ile."

( i x ) FEATURE:
    ( A ) NAME/KEY: Region
    ( B ) LOCATION: 5
    ( D ) OTHER INFORMATION: /label=Xaa-5
        / note="Xaa-5 is Ala or Asp."

( i x ) FEATURE:
    ( A ) NAME/KEY: Modified-site
    ( B ) LOCATION: 6
    ( D ) OTHER INFORMATION: /note="Xaa is Glu—NH2, Trp—NH2,
        Thr—NH2, Phe—NH2, Gly—NH2, Asp—NH2 or Tyr—NH2
        when Xaa-5 is Ala, and Cys—NH2, Trp—NH2, Phe—NH2,
        Val—NH2, Leu—NH2 or Ala—NH2 when Xaa-5 is Asp."

( x i ) SEQUENCE DESCRIPTION: SEQ ID NO:112:

Xaa Val Ile Phe Xaa Xaa
1                5

( 2 ) INFORMATION FOR SEQ ID NO:113:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is Ac—Trp or Ac—Val."

( i x ) FEATURE:
    ( A ) NAME/KEY: Region
    ( B ) LOCATION: 3
    ( D ) OTHER INFORMATION: /note="Xaa is Gln, Val or Leu."

( i x ) FEATURE:
    ( A ) NAME/KEY: Region
    ( B ) LOCATION: 4
    ( D ) OTHER INFORMATION: /note="Xaa is Ile, Gln or Val."

( i x ) FEATURE:

( A ) NAME/KEY: Region
( B ) LOCATION: 5
( D ) OTHER INFORMATION: /note="Xaa is Ile or Val."

( i x ) FEATURE:
( A ) NAME/KEY: Modified-site
( B ) LOCATION: 6
( D ) OTHER INFORMATION: /note="Xaa is Ile—NH2 or Val—NH2."

( x i ) SEQUENCE DESCRIPTION: SEQ ID NO:113:

Xaa Ile Xaa Xaa Xaa Xaa
1               5

( 2 ) INFORMATION FOR SEQ ID NO:114:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="Xaa is Ac—Ala."

( i x ) FEATURE:
( A ) NAME/KEY: Modified-site
( B ) LOCATION: 6
( D ) OTHER INFORMATION: /note="Xaa is Pro—NH2."

( x i ) SEQUENCE DESCRIPTION: SEQ ID NO:114:

Xaa Lys Ile Tyr Arg Xaa
1               5

( 2 ) INFORMATION FOR SEQ ID NO:115:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="Xaa is Ac—Ala."

( i x ) FEATURE:
( A ) NAME/KEY: Modified-site
( B ) LOCATION: 6
( D ) OTHER INFORMATION: /note="Xaa is Glu—NH2."

( x i ) SEQUENCE DESCRIPTION: SEQ ID NO:115:

Xaa Lys Ile Tyr Arg Xaa
1               5

( 2 ) INFORMATION FOR SEQ ID NO:116:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="Xaa is Ac—Ala."

( i x ) FEATURE:

( A ) NAME/KEY: Modified-site
                ( B ) LOCATION: 6
                ( D ) OTHER INFORMATION: /note="Xaa is Asp—NH2."

( x i ) SEQUENCE DESCRIPTION: SEQ ID NO:116:

Xaa   Lys   Ile   Tyr   Arg   Xaa
1                       5

( 2 ) INFORMATION FOR SEQ ID NO:117:

( i ) SEQUENCE CHARACTERISTICS:
                ( A ) LENGTH: 6 amino acids
                ( B ) TYPE: amino acid
                ( D ) TOPOLOGY: linear ( i i ) MOLECULE TYPE: peptide ( i x ) FEATURE:
                ( A ) NAME/KEY: Modified-site
                ( B ) LOCATION: 1
                ( D ) OTHER INFORMATION: /note="Xaa is Ac—Met."

( i x ) FEATURE:
                ( A ) NAME/KEY: Modified-site
                ( B ) LOCATION: 6
                ( D ) OTHER INFORMATION: /note="Xaa is Thr—NH2."

( x i ) SEQUENCE DESCRIPTION: SEQ ID NO:117:

Xaa   Thr   Lys   Ile   Phe   Xaa
1                       5

( 2 ) INFORMATION FOR SEQ ID NO:118:

( i ) SEQUENCE CHARACTERISTICS:
                ( A ) LENGTH: 6 amino acids
                ( B ) TYPE: amino acid
                ( D ) TOPOLOGY: linear ( i i ) MOLECULE TYPE: peptide ( i x ) FEATURE:
                ( A ) NAME/KEY: Modified-site
                ( B ) LOCATION: 1
                ( D ) OTHER INFORMATION: /note="Xaa is Ac—Thr."

( i x ) FEATURE:
                ( A ) NAME/KEY: Modified-site
                ( B ) LOCATION: 6
                ( D ) OTHER INFORMATION: /note="Xaa is Thr—NH2."

( x i ) SEQUENCE DESCRIPTION: SEQ ID NO:118:

Xaa   Thr   Lys   Ile   Phe   Xaa
1                       5

( 2 ) INFORMATION FOR SEQ ID NO:119:

( i ) SEQUENCE CHARACTERISTICS:
                ( A ) LENGTH: 12 amino acids
                ( B ) TYPE: amino acid
                ( D ) TOPOLOGY: linear ( i i ) MOLECULE TYPE: peptide ( i x ) FEATURE:
                ( A ) NAME/KEY: Modified-site
                ( B ) LOCATION: 1
                ( D ) OTHER INFORMATION: /note="Xaa is Ac—Tyr."

( i x ) FEATURE:
                ( A ) NAME/KEY: Modified-site
                ( B ) LOCATION: 12
                ( D ) OTHER INFORMATION: /note="Xaa is Met—NH2."

( x i ) SEQUENCE DESCRIPTION: SEQ ID NO:119:

```
Xaa  Tyr  Gly  Ala  Lys  Ile  Tyr  Arg  Pro  Asp  Lys  Xaa
1              5                        10
```

SCANNING SYNTHETIC PEPTIDE COMBINATORIAL LIBRARIES: OLIGOPEPTIDE MIXTURE SETS HAVING A ONE PREDETERMINED RESIDUE AT A SINGLE, PREDETERMINED POSITION, METHODS OF MAKING AND USING THE SAME

CROSS-REFERENCE TO RELATED APPLICATIONS

This is a continuation-in-part of application Ser. No. 07/797,551, now abandoned, filed Nov. 19, 1991, that was a continuation-in-part of application Ser. No. 07/701,658, filed May 16, 1991, now abandoned, that was a continuation-in-part of application Ser. No. 07/617,023, filed Nov. 21, 1990, now abandoned.

TECHNICAL FIELD

The present invention relates to the organic synthesis of oligopeptide sequences. More particularly the invention relates to the synthesis and use of a plurality of independent sequence sets, their syntheses and uses.

BACKGROUND AND RELATED ART

Over the last several years, developments in peptide synthesis technology have resulted in automated synthesis of peptides accomplished through the use of solid phase synthesis methods. The solid phase synthesis chemistry that made this technology possible was first described in Merrifield et al. *J. Amer. Chem. Soc.*, 85:2149–2154 (1963). The "Merrifield method" has for the most part remained largely unchanged and is used in nearly all automated peptide synthesizers available today.

In brief, the Merrifield method involves synthesis of a peptide chain on solid support resin particles. These particles typically consist of polystyrene cross-linked with divinyl benzene to form porous beads which are insoluble in both water and various organic solvents used in the synthesis protocol. The resin particles contain a fixed amount of amino- or hydroxylmethyl aromatic moiety which serves as the linkage point for the first amino acid in the peptide.

Attachment of the first amino acid entails chemically reacting its carboxyl-terminal (C-terminal) end with derivatized resin to form the carboxyl-terminal end of the oligopeptide. The alpha-amino end of the amino acid is typically blocked with a t-butoxy-carbonyl group (t-Boc) or with a 9-fluorenylmethyloxycarbonyl (Fmoc) group to prevent the amino group which could otherwise react from participating in the coupling reaction. The side chain groups of the amino acids, if reactive, are also blocked (or protected) by various benzyl-derived protecting groups in the form of ethers, thioethers, esters, and carbamates.

The next step and subsequent repetitive cycles involve deblocking the amino-terminal (N-terminal) resin-bound amino acid (or terminal residue of the peptide chain) to remove the alpha-amino blocking group, followed by chemical addition (coupling) of the next blocked amino acid. This process is repeated for however many cycles are necessary to synthesize the entire peptide chain of interest. After each of the coupling and deblocking steps, the resin-bound peptide is thoroughly washed to remove any residual reactants before proceeding to the next. The solid support particles facilitate removal of reagents at any given step as the resin and resin-bound peptide can be readily filtered and washed while being held in a column or device with porous openings.

Synthesized peptides are released from the resin by acid catalysis (typically with hydrofluoric acid or trifluoroacetic acid), which cleaves the peptide from the resin leaving an amide or carboxyl group on its C-terminal amino acid. Acidolytic cleavage also serves to remove the protecting groups from the side chains of the amino acids in the synthesized peptide. Finished peptides can then be purified by any one of a variety of chromatography methods.

Though most peptides are synthesized with the above described procedure using automated instruments, a recent advance in the solid phase method by R. A. Houghten allows for synthesis of multiple independent peptides simultaneously through manually performed means. The "Simultaneous Multiple Peptide Synthesis" ("SMPS") process is described in U.S. Pat. No. 4,631,211 (1986); Houghten, *Proc. Natl. Acad. Sci.*, 82:5131–5135 (1985); Houghten et al., *Int. J. Peptide Protein Res.*, 27:673–678 (1986); Houghten et al., *Biotechniques*, 4, 6, 522–528 (1986), and Houghten, U.S. Pat. No. 4,631,211, whose disclosures are incorporated by reference.

Illustratively, the SMPS process employs porous containers such as plastic bags to hold the solid support synthesis resin. A Merrifield-type solid-phase procedure is carried out with the resin-containing bags grouped together appropriately at any given step for addition of the same, desired amino acid residue. The bags are then washed, separated and regrouped for addition of subsequent same or different amino acid residues until peptides of the intended length and sequence have been synthesized on the separate resins within each respective bag.

That method allows multiple, but separate, peptides to be synthesized at one time, since the peptide-linked resins are maintained in their separate bags throughout the process. The SMPS method has been used to synthesize as many as 200 separate peptides by a single technician in as little as two weeks, a rate vastly exceeding the output of most automated peptide synthesizers.

A robotic device for automated multiple peptide synthesis has been recently commercialized. The device performs the sequential steps of multiple, separate solid phase peptide synthesis through iterative mechanical-intensive means. This instrument can synthesize up to 96 separate peptides at one time, but is limited at present by the quantity of its peptide yield.

Of interest is work by Geysen et al., which deals with methods for synthesizing peptides with specific sequences of amino acids and then using those peptides to identify reactions with various receptors. Geysen et al.'s work presupposes that one has a prior knowledge of the general nature of the sequences required for the particular receptors, so that the appropriate group of peptides can be synthesized. See U.S. Pat. Nos. 4,708,871 and 4,833,092; P.C.T. Publications Nos. WO 84/03506 and WO 84/03564; Geysen et al., *Proc. Natl. Acad. Sci. U.S.A.*, 81:3998–4002 (1984); Geysen et al., *Proc. Natl. Acad. Sci. U.S.A.*, 82:178–182 (1985); Geysen et al., in *Synthetic Peptides as Antigens*, 130–149 (1986); Geysen et al., *J. Immunol. Meth.*, 1.02:259–274 (1987); and Schoofs et al., *J. Immunol.*, 140:611–616 (1988).

Several research groups have reported the synthesis of synthetic combinatorial libraries of peptides. Those reports are discussed below.

In published PCT application PCT/AU85/00165 (WO 86/00991), Geysen describes a method for determining so-called "mimotopes". A mimotope is defined as a catamer (a polymer of precisely defined sequence formed by the condensation of a precise number of small molecules), which in at least one of its conformations has a surface region with the equivalent molecule topology to the epitope of which it is a mimic. An epitope is defined as the surface of an antigenic molecule which is delineated by the area of interaction with an antibody molecule.

The mimotopes are synthesized on a series of solid polymer (e.g. polyethylene with a coating of grafted acrylic acid) rods having a diameter of about 4 mm and a length of about 50 mm. A spacer formed by reaction of the ε-amino group of t-Boc-lysine methyl ester and then t-Boc-alanine was added to the resins, followed by removal of the t-Boc group to provide an amino group to be used to begin the syntheses.

A mixture of blocked amino acids containing different amounts of each of the blocked twenty amino acids to be used was dissolved in dimethyl formamide and then coupled to the rods. That first coupling was repeated three times using conventional solid phase synthesis techniques. Twenty amino acid residues were individually next added so that twenty 5-mer sequences were prepared, each having a single, known amino acid residue at the amino-terminus and a mixture of amino acid residues at each of the four other positions of the chain. Each of those twenty rod-linked peptides was then individually reacted with each of the twenty amino acid residues to form 400 (20×20) 6-mer peptides having the two amino-terminal positions defined and the four remaining positions as mixtures. Two more positions of mixtures of amino acids were then added, and the terminal amine acetylated to form N-acetyl 8-mers linked to the rods whose first two amino acid positions were undefined (mixtures), followed by two defined positions, followed by four undefined positions (mixtures), followed by the spacer and then the supporting rods.

The 400 rod-linked N-acetyl 8-mer peptide mixture preparations were then screened in an ELISA assay using a monoclonal antibody to a desired antigenic protein. The 8-mers having the best binding to the antibody were identified. Two sets of further 8-mers that contained the identified best-binding 2-mer sequences within those 8-mers were prepared.

A first set contained mixed amino acids at the three C-terminal positions, followed toward the N-terminus, by a position containing each of the twenty amino acids made by twenty separate couplings, the identified 2-mer sequences, two further mixtures at the next two positions, and an N-terminal acetyl group. The second group contained mixed amino acids at the four C-terminal positions, the identified 2-mer sequences, a position made by separate couplings of each of the twenty amino acids, mixed amino acids as the terminal residues and an N-terminal acetyl group.

Each of those rod-linked N-acetyl 8-mers was again screened in an ELISA with the monoclonal antibody. The best binding sequences for each group were identified, and thus 4-mer, best-binding sequences were identified.

The above process of separately adding each of the amino acids on either side of identified best-binding sequences was repeated until an optimum binding sequence was identified.

The above method, while elegant, suffers from several disadvantages. First, owing to the small size of each rod used, relatively small amounts of each peptide is produced. Second, each assay is carried out using the rod-linked peptides, rather than the free peptides in solution. Third, even though specific amounts of each blocked amino acid are used to prepare the mixed amino acid residues at the desired positions, there is no way of ascertaining that an equimolar amount of each residue is truly present at those positions.

In addition, Furka et al., (1988, 14th International Congress of Biochemistry, Volume 5, Abstract FR:013) described the synthesis of nine tetrapeptides each of which contained a single residue at each of the amino- and carboxy-termini and mixtures of three residues at each position therebetween. The abstract further asserts that those authors' experiments indicated that a mixture containing up to 180 pentapeptides could be easily synthesized in a single run. No biological assays were reported. More recently, Furka et al., *Int. J. Peptide Protein Res.*, 37:487–493 (1991) reported on the synthesis of mixtures of 27 tetrapeptides and 180 pentapeptides prepared by physically mixing reacted resin-linked peptides. Those peptides were synthesized with one or mixtures of three or four residues at each position along the chain. No biological results using those relatively simple mixtures were reported.

Recent reports (Devlin et al., *Science*, 249:404–405 [1990] and Scott et al., *Science*, 249:386–390 [1990]) have described the use of recombinant DNA and bacterial expression to create highly complex mixtures of peptides. For example, a 45-nucleotide base pair stretch of DNA was synthesized in which the individual nucleotide bases were varied to contain all four possible nucleotide bases (guanine, adenine, cytosine and thymidine) at every position in the synthesized DNA chain, except at each third position (3, 6, 9, etc.) which contained only guanine and cytosine. The omission of adenine and thymidine at every third position in the synthesized DNA removed the possibility of chain terminator triplet codons ending in A or T, such as TAA or TGA.

The resulting DNA sequence would then code for a mixture of 15-mer peptides with all combinations of the 20 naturally occurring amino acids at each position.

Those investigators fused the 45 synthetic nucleotide sequence to a gene coding for the coat protein of a simple bacteriophage and created a large library of these bacteriophages. Each member of the library contained a different 45-mer DNA fusion sequence and therefore each member of the library resulted in a different 15-mer peptide fused to the outer coat protein of its corresponding fully assembled bacteriophage particle. Screening of the recombinant bacteriophage particles in a biochemical assay allowed the investigators to find individual peptide-coat protein fusions (bacteriophages) that were active in that assay by enrichment, selection and clonal isolation of the enriched bacteriophages that contained active peptide fusions. By determining the DNA sequence of the cloned bacteriophages, the investigators could deduce which peptide sequences were active in their assay.

That method yielded several peptide sequences from a mixture of $10^7$ or more recombinant bacteriophages. Each of the 15-mer peptides found contained the same four-amino-acid sequence somewhere within its overall sequence, thereby allegedly validating the assay accuracy and methodological approach.

The recombinant DNA method is extremely powerful for screening large numbers of peptides. However, it is limited in that the peptides must be fused to a larger protein as a result of and integral to the design of the method. The peptide-protein fusions (and corresponding bacteriophage particles) are likely to be unreactive in many biochemical, biological and in vivo assays where the peptides must be present in solution without steric hindrance or conformational distortion. In addition, the method results in an over-representation of some sequences of peptides due to the inherent redundancy of the genetic code which has several codons per amino acid in some cases and only one codon per amino acid in others.

Still further, neither group reported data as being definitive for the determination of optimal peptide ligands for strepavidin (Devlin et al.), or for the two monoclonal antibodies raised against myohemerythrin (Scott et al.). Neither group provided a single specific answer comparable to the expected sequence.

More recently, Fodor et al., *Science*, 251:767–773 (1991), described the solid phase synthesis of thousands of peptides or nucleotides on glass microscope slides treated with aminopropyltriethoxysilane to provide amine functional groups. Predetermined amino acids were then coupled to predefined areas of the slides by the use of photomasks. The photolabile protecting group NVOC (nitroveratryloxycarbonyl) was used as the amino-terminal protecting group.

By using irradiation, a photolabile protecting group and masking, an array of 1024 different peptides coupled to the slide was prepared in ten steps. Immunoreaction with a fluorescent-labeled monoclonal antibody was assayed with epifluorescence microscopy.

This elegant method is also limited by the small amount of peptide or oligonucleotide produced, by use of the synthesized peptide or nucleotide affixed to the slide, and also by the resolution of the photomasks. This method is also less useful where the epitope bound by the antibody is unknown because all of the possible sequences are not prepared.

The primary limitation of the above new approaches for the circumvention of individual screening of millions of individual peptides by the use of a combinatorial library is the inability of the peptides generated in those systems to interact in a "normal" manner with acceptor sites, analogous to natural interaction processes (i.e., in solution at a concentration relevant to the receptors, antibody binding sites, enzyme binding pockets, or the like being studied without the exclusion of a large percentage of the possible combinatorial library). Secondarily, the expression vector systems do not readily permit the incorporation of the D-forms of the natural amino acids or the wide variety of unnatural amine acids which would be of interest in the study or development of such interactions.

Yet another approach was reported by Lam et al., *Letters to Nature*, 354:82–84 (1991). Those workers reported the preparation of millions of bead-linked peptides, each bead containing a different peptide. The peptide-linked beads were reacted with a fluorescent- or enzyme-labeled acceptor, the beads bound by the acceptor were physically removed, and the sequence of the bound peptide was analyzed.

The interest in obtaining biologically active peptides for pharmaceutical, diagnostic and other uses would make desirable a procedure designed to find a mixture of peptides or a single peptide within a mixture with optimal activity for a target application. Screening mixtures of peptides enables the researcher to greatly simplify the search for useful therapeutic or diagnostic peptide compounds. Mixtures containing hundreds of thousands or more peptides should be readily screened since many biochemical, biological and small animal assays are sensitive enough to detect activity of compounds that have been diluted down to the nanogram or even picogram per milliliter range, the concentration range at which naturally occurring biological signals such as peptides and proteins operate.

Almost all of the broad diversity of biologically relevant ligand-receptor (or affector-acceptor) interactions occur in the presence of a complex milieu of other substances (i.e., proteins make up approximately 5–10 percent of plasma, e.g. albumin 1–3 percent, antibodies 2–5 percent-salts, lipids/fats, etc.). This is true for virtually all biologically active compounds since most are commonly present, and active, at nanomolar and lower concentrations. These compounds are also, in most instances, produced distant from their affection sites.

That a small peptide (or other molecule) can readily "find" an acceptor system, bind to it, and affect a necessary biological function prior to being cleared from the circulation or degraded suggested that a single specific peptide sequence can be present in a very wide diversity, and concentration, of other individual peptides and still be recognized by its particular acceptor system (antibody, cellular receptor, etc.). If one could devise a means to prepare and screen a synthetic combinatorial library of peptides, then the normal exquisite selectivity of biological affector/acceptor systems could be used to screen through vast numbers of synthetic oligopeptides.

The availability of a wide variety of clearly identified peptides in relatively limited mixtures would greatly facilitate the search for optimal peptides for any particular therapeutic end use application. At the present time, researchers are hampered by the inability to rapidly create, identify and screen large numbers of peptides with specific receptors. Work such as reported by Geysen has been valuable where the general nature of the required amino acid residue sequence could be previously determined, so that the specific peptides of interest could be individually formulated. However, such techniques cannot insure that the optimum peptides are identified for testing.

It would therefore be of considerable interest to have a method for the synthesis of mixtures of peptides in which individual residue positions can be specifically defined, such that a comprehensive array of peptides is available to researchers for the identification of one or more of the optimal peptides for reaction with receptors (acceptors) of interest, from which one can derive optimum therapeutic materials for treatment of various organism dysfunctions.

BRIEF SUMMARY OF THE INVENTION

A plurality of sets of self-solubilizing, unsupported mixed oligopeptides is contemplated in one embodiment of the invention. Each set consists essentially of a mixture of equimolar amounts of linear oligopeptide chains containing the same number of five to ten amino acid residues in each oligopeptide chain. The members of each set have one of at least six different predetermined amino acid residues at a single, predetermined position of the oligopeptide chain, and each set has equimolar amounts of the same at least six different amino acid residues at the same other positions of the oligopeptide chain. The plurality of sets has a different one of the at least six different predetermined amino acid residues present at the same predetermined chain position within each set and has equimolar amounts of the same at least six different amino acid residues at the other positions in the oligopeptide chain.

Another embodiment of the invention is a process that utilizes the above sets and comprises the steps of:

(a) providing separate pluralities of sets of self-solubilizing, unsupported mixed oligopeptides, each of the pluralities having sets that consist essentially of a mixture of equimolar amounts of linear oligopeptide chains containing five to about ten amino acid residues in each chain. The members of each set have one of at least six different predetermined amino acid residues at a single, predetermined position of the oligopeptide chain, and have the at least six different amino acid residues at the same other positions of the oligopeptide chain. Each set has equimolar amounts of the at least six different amino acid residues at the other positions in the oligopeptide chain, but differs from the other sets in that the identity and chain position of the one of at least six predetermined amino acid residues present at the predetermined chain position within each set is different between the sets. Each plurality of sets differs from the other plurality of sets by the chain position of the one of at least six different predetermined amino acid residues.

(b) Each set is separately admixed with the acceptor in an aqueous medium at a set concentration of about 0.1 milligrams per liter to about 100 grams per liter and preferably about 1 milligram per liter to about 100 grams per liter. The binding of each set to the acceptor is separately assayed, and the one or more sets that provided preferential binding for each different chain position is determined.

The identity and position of the amino acid residue of each one or more sets that provided preferential binding for each chain position provides the amino acid residue sequence for the ligand that preferentially binds to the acceptor.

Another embodiment of that process comprises the steps of:

(a) providing a plurality of sets of self-solubilizing, unsupported mixed oligopeptides in which each set consists essentially of a mixture of equimolar amounts of linear oligopeptide chains containing the same number of five to ten amino acid residues in each oligopeptide chain. The members of each set have one of at least six predetermined amino acid residues at a single, predetermined position of the oligopeptide chain, and each set has equimolar amounts of the same at least six different amino acid residues at the same other positions of the oligopeptide chain. The plurality of sets has equimolar amounts of the at least six different amino acid residues at the other positions in the oligopeptide chain but differ in that the one of at least six predetermined amino acid residues present at the predetermined chain position within each set is different between the sets.

(b) Each set from the plurality of sets is separately admixed with the acceptor in an aqueous medium at a concentration of about 0.1 milligrams per liter to about 100 grams per liter and preferably about 1 milligram per liter to about 100 grams per liter. The binding of each set to the acceptor is separately assayed, and the one or more sets of the plurality of sets that provided preferential binding compared to the other sets assayed is determined.

(c) Another plurality of sets of self-solubilizing, unsupported mixed oligopeptides is provided in which each set consists essentially of a mixture of equimolar amounts of linear oligopeptide chains containing the same number of five to ten amino acid residues in each oligopeptide chain and having the same chain length as the first named plurality of sets. The members of each set have one of at least six predetermined amino acid residues at another single, predetermined position of the oligopeptide chain different from the first-named sets, and each set has equimolar amounts of the same at least six different amino acid residues at the same other positions of the oligopeptide chain. This other plurality of sets has equimolar amounts of the at least six different amino acid residues at the other positions in the oligopeptide chain but differs from other set pluralities in that the one of at least six predetermined amino acid residue present at the predetermined chain position within each set is different between the set pluralities.

(d) Each set from the other plurality of sets is separately admixed with the acceptor in an aqueous medium at a concentration of about 1 milligram per liter to about 100 grams per liter. The binding of each other set to the acceptor is separately assayed, and the one or more sets of the other plurality of sets that provided preferential binding compared to the other sets assayed is determined.

(e) Steps (c) and (d) are repeated using further pluralities of sets that differ from each other and the set pluralities of steps (a) and (c) by the chain position of the one of at least six predetermined amino acid residues at the predetermined chain position until at least five pluralities of sets have been assayed.

The identity and position of the one of at least six amino acid residues of each one or more sets that provided preferential binding so determined for each plurality of sets provides the amino acid residue sequence for the ligand that preferentially binds to the acceptor.

Preferably, the at least five pluralities of sets utilized contain the single, predetermined amino acid residues at adjacent positions in the amino acid residue sequence that is determined. Exemplary acceptors for a contemplated process include an antibody combining site-containing molecule and cellular receptors that can be present in living cells or in cell preparations.

The length of each oligopeptide of each of the plurality of sets is preferably five to eight, and more preferably six amino acid residues. It is also preferred that the oligopeptides of each set contain a C-terminal amide (—NH$_2$) group. It is further preferred that the oligopeptides of each plurality of sets have an N-terminal $C_1$–$C_8$ acyl amide group, such as an acetyl group. The positions of the oligopeptides in the set pluralities having equimolar amounts of different amino acid residues are preferably occupied by at least 10 and more preferably about 15 to about 20 amino acid residues.

Specific oligopeptides are also contemplated. Among those contemplated oligopeptides are those of SEQ ID NOS:7–11, 32, 33 and 37–46 that inhibit binding to the mu opoid receptor, those of SEQ ID NOS:59–63 and 80–113 that inhibit hemolysis by melittin, and those of SEQ ID NOS:114–119 that inhibit the action of trypsin.

BRIEF DESCRIPTION OF THE DRAWINGS

In the drawings forming a portion of this disclosure;

FIGS. 2A–2F are a series of six graphs that illustrate inhibition of monoclonal antibody mAb 125–10F3 binding to the antigenic polypeptide SEQ ID NO:1 by six sets of eighteen sets of unsupported mixed 6-mer N-acetyl oligopeptide amides. Each graph provides results for 18 sets in which a different amino acid residue is present at th same position of the 6-mer sequence with the remaining positions of each sequence occupied by equimolar amounts of the eighteen amino acid residues used. The position of the 18 different residues for each 18 sets is denoted by an "O" with a subscript number placed above each graph, wherein "X's" indicate positions of the sequence at which an equimolar mixture of amino acid residues is present, Ac denotes an N-terminal acetyl group and —$NH_2$ indicates a C-terminal amido group. Each vertical bar represents the inhibition observed when the amino acid residue shown along the abscissa in single letter code was used at the position shown by the O in a mixture set.

FIGS. 3A–3F are a series of six graphs that illustrate inhibition of monoclonal antibody 17DO9 binding to the antigenic polypeptide SEQ ID NO:2 by six sets of eighteen sets of unsupported mixed 6-mer N-acetyl oligopeptide amides. The data are presented as in FIG. 2.

Figure 1A:
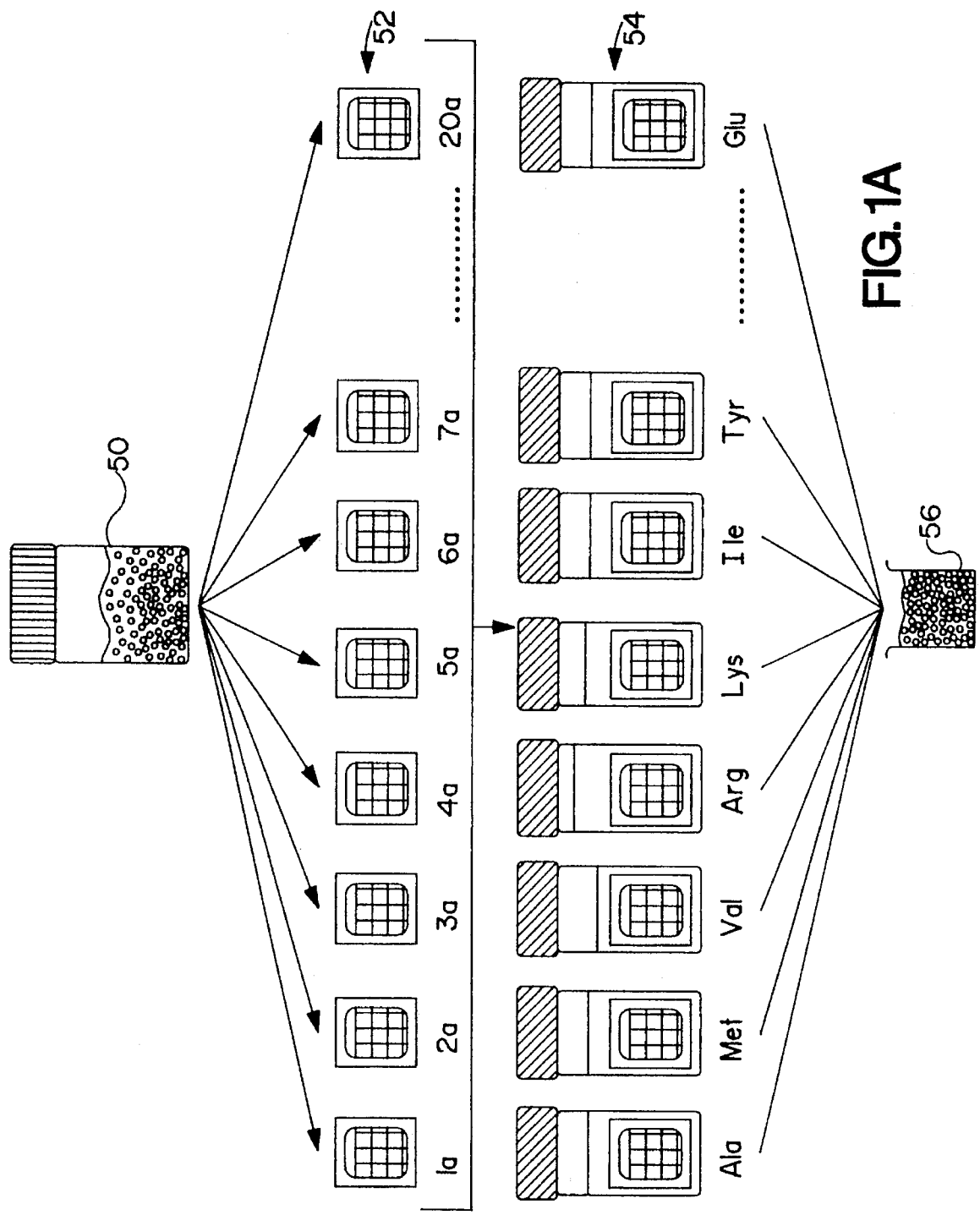
FIGS. 1A–1B are a schematic flow chart in two sheets illustrating a process of this invention in an embodiment in which peptide mixtures are formed from the twenty naturally occurring amino acids.

The present invention has several benefits and advantages.

One benefit of this invention is the facilitation of the formation and identification of specific biologically active oligopeptide sequences for pharmaceutical, diagnostic and other uses, particularly those oligopeptide sequences that are of particular efficacy for the therapeutic treatment of target diseases.

An advantage of the present invention is that an amino acid residue sequence of an oligopeptide ligand that preferentially binds to a preselected receptor can be ascertained in relatively few assays; i.e., such a sequence can be found in a number of assays that equals the number of different amino acids to be used (at least six and more preferably about 15 to about 20) multiplied by the number of adjacent sequence positions used. Thus, for a 6-mer using the 20 natural amino acids, 120 assays (6×20) are used.

Another benefit of the present invention is that aliquots from the same set of unsupported mixed oligopeptides can be used for assays against any receptor to be screened.

Still further benefits and advantages of the invention will be apparent to the skilled worker from the discussion that follows.

DETAILED DESCRIPTION OF THE INVENTION

Introduction

In the description below, the invention will be described in the embodiment in which the oligopeptides that are formed are prepared from most or all of the twenty naturally occurring amino acid residues. It will be understood, however, that the invention can be used with at least six different amino acid residues, and more than twenty different residues.

For instance, one can include one or both isomers of ornithine, norleucine, beta-alanine, hydroxyproline, and the D-stereoisomers of the naturally occurring twenty amino acids. Consequently, as used in the specification and claims herein, the term "amino acid" will, unless otherwise stated, be intended to include not only the naturally occurring L-amino acids but also their D-stereoisomers and the derivatives thereof as well as all other amino acids. The phrases "amino acid derivative", "protected amino acid derivative" or the like are used herein for a protected amino acid added as a reactant, whereas the phrase "amino acid residue", "residue" or the like is used herein for a reacted protected amino acid that is a portion of an oligopeptide chain.

Further, the terms "peptide" and "oligopeptide" are considered to be synonymous (as is commonly recognized) and each term can be used interchangeably as the context requires. The word "polypeptide" is used for chains containing more than ten amino acid residues. All oligopeptide and polypeptide formulas or sequences shown herein are written from left to right and in the direction from amino-terminus to carboxy-terminus.

The abbreviations used herein for derivatives and residues of the twenty natural amino acids are reproduced in the following Table of Correspondence:

| TABLE OF CORRESPONDENCE | | |
|---|---|---|
| Abbreviation | | |
| 1-Letter | 3-Letter | Amino Acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |
| X | Xaa | another residue, or one of several residues |

The word "predetermined" is used in two contexts herein, and has a similar meaning in each context.

A "predetermined" amino acid residue is a single residue whose identity is known or specifically defined, e.g., alanine, glycine, tyrosine, etc., as compared to being a mixture of residues. A "predetermined position" in an oligopeptide mixture sequence or chain is a position, from and including the amino-terminal residue as position 1, occupied by a predetermined amino acid residue or of a mixture of residues, and which position is known and specifically identified.

Thus, a predetermined amino acid, such as arginine, at a predetermined position of an oligopeptide mixture can be at any of positions 1 through 10 from and including the amino-terminus that is chosen in any given synthesis. An oligopeptide mixture contemplated herein has one position occupied by one of the different predetermined residues, as well as at least four remaining positions occupied by a mixture of the coupled residues.

The letter "O" is used to indicate a predetermined, but unspecified amino acid residue. Subscripted letter "O", e.g., $O_1, O_2, O_3 \ldots O_n$ etc. indicate a predetermined amino acid residue that is predetermined (specified) and at the same position (1, 2, 3 ... n) among a set of oligopeptide mixtures or solid support-coupled oligopeptide mixtures. Subscripted numbers need not start at the amino-terminus for any given mixture.

The letter "X" is used to indicate that a position in an oligopeptide formula occupied by that letter is an equimolar mixture of each of at least six amino acid residues coupled, and preferably ten or more such residues. Subscripted letters "X" indicate mixtures at one or more predetermined positions from the N-terminus as indicated by the subscripted numeral.

The letter "B" is used to indicate a solid support used in the syntheses described herein, such as a particulate resin.

The designation Xaa with a subscript numeral adjacent to the X is used as a three-letter indication that the position of the subscript numeral can be occupied by more than one residue as defined thereafter.

A contemplated oligopeptide mixture set contains a single, predetermined amino acid at one predetermined chain position and mixtures of the amino acid residues used for synthesis of the other positions of the oligopeptide chain. At least six different amino acid derivatives are used for the synthesis of the mixed positions and one of those same six residues is the single, predetermined residue for a given set. In preferred practice at least ten different amino acid derivatives are used for synthesis and more preferably still, about 15 to about 20 amino acid derivatives are used for synthesis and are residues of the mixture positions and each can constitute the single, predetermined residue at the single, predetermined position.

Thus, the residue of that single, predetermined position can be one of at least six, preferably ten or more preferably about 15 to about 20 residues. For ease of expression, that residue is usually referred to herein as "a single, predetermined amino acid residue", whereas in other instances that residue is described as "one of at least six amino acid residues" or the like, or more specifically still, as "one of eighteen amino acid residues".

Peptides are one of a number of fundamental classes of biologically relevant effector molecules. Acceptor systems for peptides include: antibodies, enzymes, membrane-bound and internal cellular receptors. Biologically important peptides include bradykinin, oxytocin, β-endorphins, insulin, and the like. Drug discovery involving peptides invariably requires the synthesis and testing of hundreds to thousands of analogs of the original biologically active sequences. In order to understand a given peptide's structure activity relationships (SAR), very large numbers of peptide analogs are needed in all of these areas.

The diversity of the combinatorial possibilities of even the 20 natural amino acids makes the before-described synthesis methods sorely limited in the task of screening for optimal peptide antigens, peptide ligands for biologically relevant acceptor systems, enzyme inhibitors, antimicrobials, and the like [i.e., there are 64,000,000 possible six residue peptides ($20^6$) 1,280,000,000 possible seven residue peptides ($20^7$), and the like]. Although the synthetic methods discussed before have greatly facilitated studies with synthetic peptides, and are available commercially either on a custom basis or for use in kit form, they permit only a very small fraction of possible oligopeptides (composed of either natural or unnatural amino acids) to be prepared.

The studies underlying the present invention began with the premise that for a synthetic peptide combinatorial library (complex mixture set of oligomers) approach to be generally useful, the following criteria would have to be met: (1) mixture sets of oligopeptides would have to be generated in which all of the oligopeptides pertinent to the study would be present in equimolar, or approximately equimolar concentrations; (2) screening of the defined repertoire (set) of oligopeptides would be able to be carried out in solution (i.e., not attached to a solid support or as part of a larger protein); (3) minimal manipulation of the oligopeptide(s) mixture set(s) to be studied would be necessary during their synthesis, characterization and use; (4) screening would be able to be carried out at a high enough solution concentration of the necessary synthetic peptide libraries so that it would be possible to reduce the intended very large repertoire of oligopeptides to a small number of selected "enhanced" sequences for further development; (5) large numbers of peptides would have to be readily prepared in the necessary quantities as needed (10–100s of milligrams) with purities as high as existing chemistries permitted in order to further enhance the activity of initial sequences selected; and finally, (6) the results generated from such a synthetic peptide combinatorial library (SPCL) system would have to be readily verifiable in well-defined existing acceptor systems such as those found in antibodies or cellular receptors.

The first two criteria were considered to be the foundation of the present synthetic method and were deemed important to ensure general applicability to normal assay systems without complicated and/or expensive equipment or systems for its implementation. Equimolarity is also needed if, as expected, the activities found would form a hierarchy of activities and, if for practical consideration, one wished to utilize only the best, or a few of the best, determined sequences that exhibited preferential binding.

Thus, the equimolar amounts of each component making up the repertoire (set) to be studied could be expected to ensure the necessary selectivity of the interactions of the desired oligopeptide in the mixture to be used (i.e., the "needle in the haystack"-finding the correct hexapeptide in the 64,000,000 possible combinations of the 20 natural amino acids would be analogous to finding a single steel needle in 63,999,999 copper needles). As an insight into the extreme selection criterion involved in such a system, it is helpful if one considers that a single six-letter word would have to be readily found in the presence of 63,999,999 other six-letter words (63,999,999 six-letter words would fill approximately 50,000 pages of text of the size found in a usual scientific journal).

The known methods are useful, and have been used for the illustrative oligopeptide mixture sets exemplified. However, a different approach can also be used that a priori ensures substantial equimolarity. This approach involves the separation and recombination of oligopeptide-coupled solid supports. This approach entails the coupling to completion of each of the desired protected amino acids (i.e., t-Boc alanine, etc.) with equimolar portions of starting oligopeptide solid support such as a resin. Assurance that the reactions have all been driven to completion (>99.5 percent for each step) is made by standard assay procedures.

The resulting reacted resins are then combined and thoroughly mixed as solids (physically mixed) to form a pool, and following their deprotection and neutralization, the resulting pooled mixture is again divided into a number of equal portions. Each of these portions (that contain equimolar amounts of the different starting amino acid residue-coupled resins) is reacted with a single, predetermined amino acid derivative or is again separately coupled to completion with each of the desired protected amino acid derivatives. Where the 20 natural amino acids are used at each of the two coupling steps, this yields 20 different dipeptide-coupled resins for each of the 20 single amino acid resins (400 different dipeptide resins in total). This process is then repeated until the desired length of the mixture of oligopeptide-coupled resins has been obtained. The single, predetermined residue is added similarly, but without mixing after the coupling step.

This method can be used with any number or kind of amino acid without limitation, to generate the exact oligopeptide-coupled resin mixture pool (coupled synthetic combinatorial library) required. After cleavage of the oligopeptide mixture from the solid support, amino acid and sequence analyses can be used to confirm the expected results, but the accuracy of the methods used to prepare the resin mixtures as described herein exceeds that of the analysis systems. Thus, the exactitude of physically weighing the resins, mixing them, separating them, and recombining them, along with the assurance of individual amino acid coupling completion by ninhydrin, picric acid or other means, ensures the necessary equimolarity.

In initial preparations, an acetyl group on the N-terminal residue of each component of the combinatorial resin library was radiolabeled with tritium to ensure that complete cleavage of the peptide from its resin had occurred and that all solution concentrations were equal. Following cleavage of a set of exemplary mixtures from their resins, each was extracted until equal solution concentrations were obtained as determined by equal counts per minute (cpm) per milliliter (ml).

Using most or all of the twenty natural amino acids, an initial concern was that the more hydrophobic components of the mixtures would prove highly insoluble. This was not found to be the case due to the mutually self-solvating properties of the different sequences in each mixture set.

Although preferred in some instances and most effective in achieving equimolarity, the above physical mixing of solids is not always required to obtain the equimolarity needed for assay purposes. Rather, a reaction mixture containing amounts of amino acid derivatives calculated to provide reacted equimolarity, as being present in amounts proportional to their coupling constants, can be used (chemical mixture) for the coupling reactions.

Criterion three was met in that no manipulation other than extraction and/or lyophilization was necessary prior to use. Criterion four was met for most studies by the ability to work at solution concentrations of each mixture ranging from about 0.1 to about 100 mg/ml. This permitted the screening of each mixture set in assay systems at concentrations that ensured that a sufficient concentration of every individual oligopeptide was present in each assay.

For example, if the average molecular weight of a hypothetical N-acetyl C-amide hexapeptide (6-mer) oligopeptide mixture set is approximately 785, then a solution of a mixture set of 3,200,000 oligopeptides at a total final concentration of 5 mg/ml yields a concentration of each oligopeptide in each mixture of about 1.56 µg/liter (about 1.5 pmoles/liter). These concentrations, without any consideration of potential positional redundancy, ensure that a sufficient concentration of each peptide is present for normal antigen/antibody interactions, receptor/lipid interactions, and enzyme/substrate interactions.

Criterion five was met by combining the above methods with the simultaneous multiple peptide synthesis (SMPS) approach described before. Hundreds to thousands or millions of individual peptides can be readily prepared with this method using any of the currently existing chemistries. A combination of synthetic chemistries (t-Boc and Fmoc) permits: (1) the removal of all side chain protecting groups without cleaving the peptides from the resin [Tam's "low" HF method; Tam et al., *J. Am. Chem. Soc.*, 105:6442–6455 (1983)] and (2) complete, or virtually complete, removal of all of the mixtures from the resin by a final high HF treatment [Houghten et al., *Intl. J. Peptide Protein Res.*, 16:311–320 (1980)]. Use of the SMPS method is not necessary herein, but facilitates the syntheses.

Examples of the fine mapping of the determinant regions of mAb's raised against anti-peptide antibodies described hereinafter are useful here to illustrate the development of optimal binding sequences for antibodies, thereby illustrating fulfillment of criterion six.

Synthesis Processes

An unsupported set of mixed oligopeptides can be prepared by a number of types of syntheses. Two principal synthetic types and mixtures thereof are particularly preferred. Those two methods or processes for preparation are discussed below and are referred to as the physical and chemical mixture processes, respectively, as noted before.

A. Physical Mixture Process

One synthetic method useful herein utilizes a physical process for the synthesis of a complex mixture pool of solid support-coupled amino acid residues wherein the mixture contains an equimolar representation (amount) of at least six different amino acid residues coupled at at least four positions and a single, predetermined amino acid residue at a single, predetermined position. Solid support-coupled oligopeptide mixture syntheses are discussed using porous containers for simplicity of expression so that each type of synthesis need not be described.

The various solid supports such as particles can be utilized enclosed in a porous container. When that is the case, at least coupling reactions are carried out in such containers. However, porous containers need not be used and coupling reactions can be carried out in beakers, flasks, test tubes or the like as are well known.

Several embodiments of this process are disclosed in Houghten et al., *Nature*, 354:84 (1991) and in WO 92/09300, published Jun. 11, 1992.

According to this process, (a) at least six porous containers, each containing a solid support comprised of particles linked to reactive functional groups are provided. The functional group of the solid support reacts with each amino acid to be reacted. The solid support particles are of a size that is larger than the pores of the container so that the individual solid support particles are maintained within the porous containers. Both the container and solid support are substantially insoluble in and substantially inert to a liquid medium used during the synthesis.

(b) At least six liquid media are provided, each medium containing a different protected amino acid derivative from a plurality of protected amino acid derivatives from which the oligopeptides are to be formed. Each of the protected amino acid derivatives has a first reactive functional group that reacts with the reactive functional group of the solid support, and a second reactive functional group that is capable of reacting during the reaction of the solid support functional group and the first reactive functional group, but is protected from so reacting by a selectively removable, covalently linked protecting group.

It is preferred that the first reactive functional group be the carboxyl group and the second reactive functional group be the α-amino group. In this method of synthesis, the oligopeptide is synthesized from carboxy-terminus to amino-terminus. The reverse synthetic process can also be used, but is not preferred because stereochemical inversion frequently results.

Usual selectively severable protecting groups for second functional groups of such preferred syntheses are t-Boc and Fmoc. Specific selectively severable protecting groups for other amino acid side chain functional groups are discussed hereinafter.

At least 6, more preferably at least 10, and still more preferably about 15 to about 20 different amino acid derivatives, are used. Cysteine is often omitted because of its reactivity, and coupling of methionine, histidine and tryptophan can sometimes be difficult, with the presence of tryptophan sometimes leading to dimerization when t-Boc protecting groups are used. Cysteine is usually omitted when mixtures are made, and tryptophan is usually omitted when t-Boc groups are used.

(c) Each of the containers is placed in a different one of the liquid media and the reactive functional groups of each solid support in each container is therein reacted with a first reactive functional group of a protected amino acid derivative in that respective medium to couple that protected amino acid derivative to the solid support to form a reaction mixture.

(d) Each of the reactions is maintained for a time period and under conditions sufficient for all of the reactive functional groups of the solid support to couple to the protected amino acid derivative to form at least six protected amino acid residue-coupled solid supports.

(e) Each protected amino acid residue-coupled solid support is removed from its respective container.

Equimolar amounts of the protected amino acid residue-coupled solid supports are admixed (the physical mixing step) to form a reaction product pool, wherein equal weights of the formed pool contain the same number of moles of each protected amino acid residue-coupled solid support.

The above mixture pool is useful in the stepwise synthesis of a complex mixture of solid support-coupled oligopeptides in which positions other than that occupied by the single, predetermined residue of each oligopeptide of the coupled mixture contain an equimolar representation of the at least six different amino acid residues added at each synthesis step. That predetermined, single amino acid residue can be present at the terminus of the oligopeptide, e.g. the C-terminus as described here, in which case it is added to the solid support prior to the above steps being carried out, as discussed hereinafter.

The worker using this process will often continue with steps (f)–(k), below, to provide further mixed positions. However, at a predetermined stage in the syntheses, steps (l)–(o) are followed, and then if desired, steps (f)–(k) are carried out. Regardless of the order of synthesis, each of the sets is prepared having each residue to be assayed at single, predetermined positions in the sequence, with all other sequence positions being occupied by equimolar mixtures of the remaining residues being used.

(f) The reaction product pool is separated aliquots is enclosed in another porous container.

(g) The protecting groups are selectively removed from the second reactive functional groups of the pool to form a reacted product pool having free reactive functional groups. Again, step (g) can precede step (f).

(h) Each of the enclosed aliquots having free reactive functional groups is placed into one of at least six liquid media, each medium containing a different protected amino acid derivative from a plurality of protected amino acid derivatives from which the oligopeptides are to be formed to form a reaction mixture, wherein each of said protected amino acid derivatives has a first reactive functional group that reacts with the free reactive groups of the enclosed reacted product pool aliquots and a second reactive functional group that is capable of reacting during the reaction of the free reactive functional groups of the pool, but is protected from so reacting by a selectively removable, covalently linked protecting group.

(i) Each of the reactions is maintained for a time period and under conditions sufficient for all of the free reactive functional groups of the enclosed reactant product pool aliquots to couple to the protected amino acid derivative to form at least six solid support-coupled protected amino acid residue reaction products.

(j) Each of the at least six reaction products formed in step (i) is removed, and equimolar amounts of each of those reaction products are admixed to form a reaction product pool. Equal weights of the reaction product pool contain the same number of moles of each reaction product.

(k) Thereafter, steps (f) through (j) are serially repeated zero or more times until a plurality of solid support-coupled reaction product oligopeptides having the desired number of amino acid residue repeating units is synthesized.

The equimolarity is only limited by the accuracy in driving the reactions to completion, which typically is 99.5 percent or more, and weighing errors in step (a) and in separating the substantially homogeneously mixed resins into aliquots, which can be done to even greater accuracy with a multigram sample.

One specific, predetermined amino acid residue is added at one specific position in the oligopeptide chain. The positions in the chain on either side or both sides of the predetermined amino acid residue contain the equimolar mixture of at least six different reacted amino acid residues.

More specifically, using the before-described oligopeptide mixture synthesis, and remembering that enclosure of the solid support is preferred, but not required, (l) each of the protected amino acid derivative-coupled solid supports of steps (e) or (k) is removed from its respective liquid medium, and container where appropriate. Equimolar amounts of protected amino acid derivative-coupled solid supports are admixed to form a further reaction product pool, wherein equal weights of the reaction product pool contain the same number of moles of each reaction product.

(m) An aliquot of the pool formed in step (l), typically all or a majority of the pool, is enclosed in a further porous container.

(n) The protecting groups are selectively removed from the second reactive functional groups to form a reacted solid support pool having free reactive functional groups. Deprotection can again precede enclosure (when used) of the aliquot, and step (m) is omitted where a porous container is not used.

(o) The pool aliquot (enclosed or not) having free second reactive functional groups is placed into a single liquid medium that contains a single, predetermined protected amino acid derivative to form a reaction mixture in which the free reactive functional groups and single protected amino acid derivative react, the single protected amino acid derivative having a first reactive functional group that reacts with the free reactive groups of the pool aliquot, and a second reactive functional group that is capable of reacting during the reaction of the free reactive functional groups of the pool aliquot, but is protected from so reacting by a selectively removable covalently linked protecting group.

(p) The reaction mixture is maintained for a time period and under conditions sufficient for all of the free reactive functional groups of the pool aliquot to couple with the single protected amino acid derivative and form a solid support-coupled oligopeptide mixture having a single, predetermined amino acid residue in the same position in the oligopeptide chain.

A complex oligopeptide mixture is provided by following steps (a)–(e) that can be represented by the formula X-B, wherein X represents the equimolar mixture of reacted amino acid residues, and B is the solid support. Where steps (f)–(k) are followed, and the number of repeats of steps (f)–(j) carried out in step (k) is zero, an oligopeptide represented by the formula XX-B is formed. Where steps (f)–(j) are repeated once, an oligopeptide represented by the formula XXX-B is formed.

On the other hand, where steps (a)–(e) are followed by steps (l)–(p), a solid support-linked (-coupled) reaction product oligopeptide of the formula OX-B is formed, wherein X and B are as before, and O is the single, predetermined amino acid residue. In this instance, the product formed in step (p) is itself a pool because of the pooling of step (e), and therefore when steps (f)–(k) are followed, with zero repeats of steps (f)–(j), an oligopeptide mixture is synthesized that corresponds to the formula XOX-B.

It is also contemplated herein that one can start with equimolar amounts of a predetermined amino acid coupled to the solid support. In this instance, the reactive functional group of the solid support is a free second reactive functional group of an amino acid residue such as an α-amino group. When that is the case, following steps (a)–(e) and steps (f)–(j) once each [zero repeats of steps (f)–(j) in step (k)] the resulting oligopeptide-linked solid support reaction product can be represented by the formula XXO-B. Steps (l)–(p) can then be carried out, or steps (f)–(j) repeated, or both in any order as desired.

It is further contemplated that a set of mixed oligopeptides be produced by following steps (a)–(e) and then (l)–(p). That procedure forms a solid support-coupled product of the formula OX-B. The reaction product of step (p) is itself a pool because of the mixing carried out in step (e), as noted before, so that steps (f)–(j) can be carried out on that product as many times as desired to form a coupled reaction product such as a mixture pool that includes mixed residues at positions 1–4, a specified residue at position 5 and a mixture of residues at position 6.

It will be apparent to a worker skilled in this art that several further permutations and combinations of the before-described reactions can be utilized. Consequently, no further examples will be provided here.

Figure 1B:
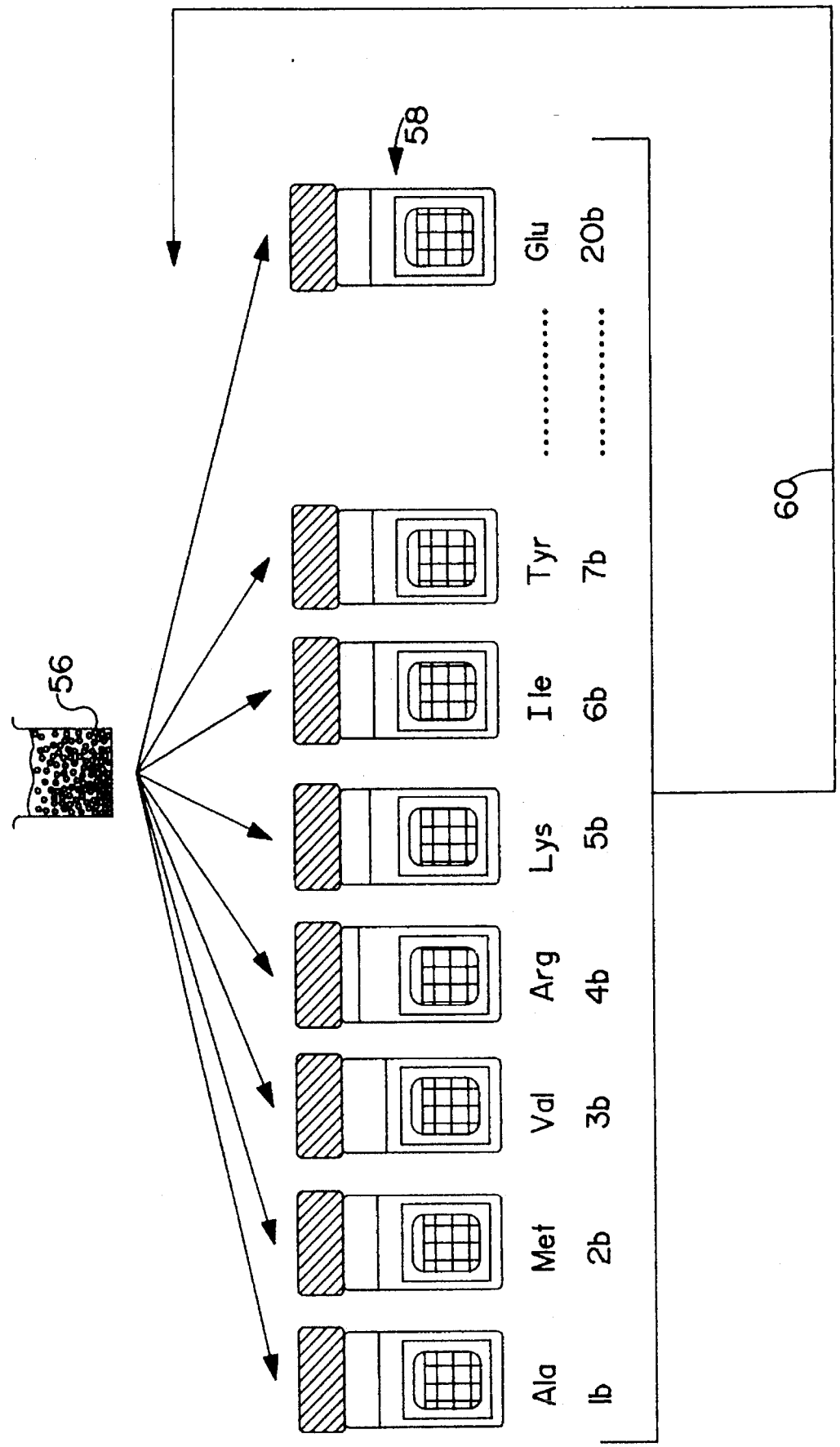

The physical mixture process and porous containers to hold the solid support particles are summarized schematically and exemplified in FIG. 1 of the drawings. A solid support comprised of a particle such as a resin linked to reactive functional groups 50 is distributed to a plurality of first porous containers shown in the row designed 52 in equal portions of moles of functional group or equal weight portions when a single homogeneous functional group-linked solid support is used. Preferred porous containers are mesh bags or packets discussed hereinafter.

For this example, it will be presumed that there are twenty porous containers in row 52, each labeled 1a–20a respectively, although all twenty are not shown for purposes of clarity, and one need not use all twenty natural amino acids in any study, or one can use more than twenty when non-natural amino acids are included. Each first container in row 52 is then separately placed in a liquid medium containing a single amino acid derivative with appropriate blocking by a selectively removable protecting group and one free, reactive functional group, e.g. a carboxyl group. Each medium contains a different amino acid derivative, so that each container is reacted with a different protected amino acid derivative, as indicated at row 54. Each protected amino acid derivative is then reactively coupled to its respective resin, with all reactions being maintained under conditions and for a time period sufficient for the reaction to go to completion, so that at the end of the reactions, each first container 1a–20a holds a support resin optimally loaded and completely reacted with a related single amino acid derivative.

The coupling completion can be determined by standard means such as Gisen's picric acid procedure [Gisen, *Anal. Chem. Acta.*, 58:248–249 (1972)], Lebl's bromophenyl blue procedure [Krchnák et al., *Coll. Czech. Chem. Commun.*, 53:2542 (1988)] or by the quantitative ninhydrin test [Savin et al., *Anal. Biochem.*, 117:147–157 (1981)] after removing a small amount of resin from each container. Given the relatively large amount of resin (solid support) used in these reactions, e.g., several grams, removal of milligram amounts of reaction product for assays does not affect equimolarity in the reaction product.

The twenty reacted solid supports, each containing a single reacted amino acid residue, are then removed from the first porous containers 1a–20a and combined in a single vessel 56 (shown in FIG. 1-A and FIG. 1-B for convenience), in which they are thoroughly mixed to form a substantially homogeneous mixture in which the particles of solid support from each of the porous containers 1a–20a are substantially equally distributed throughout the vessel to form a reaction product pool in which equal weights of the pool contain the same number of moles of each reacted solid support.

This mixture pool is then divided into twenty (or another desired number) equal weight second aliquots and one aliquot is placed (enclosed) in each of twenty second porous containers labelled 1b–20b shown in row 58, so that each second porous container 1b–20b now holds reacted solid support particles with all twenty first amino acids equally represented. After suitable amino acid unblocking (deprotection), each of these second porous containers 1b–20b is placed in a separate liquid medium, each medium again containing only one of the twenty amino acids, also appropriately blocked, and containing a free reactive functional group. Further coupling reactions are run to completion in each medium, so that at the end of the second reaction sequence each second container 1b–20b contains reacted solid support particles onto which are attached (coupled) twenty 2-mer chains of amino acids; i.e., twenty first amino acids each coupled to the single second amino acid of this second reaction step. Thus, each porous container holds twenty different 2-mer peptides in essentially equimolar quantities, and the twenty bags in total contain 400 different 2-mer peptides.

The procedure is repeated (reacted solid support removal, thorough mixing, unblocking, placement in twenty new porous containers and reaction of each oligopeptide-linked solid support in each porous container in a different medium with each medium having only a single amino acid) as shown by arrow 60 until the desired number n of steps have been accomplished. At the end of each step the number of n-mer chain oligopeptides in each container is $20^{n-1}$, and the total number of n-mer oligopeptides in all twenty containers is $20^n$. Serially repeating the steps of separating-reenclosing, unblocking reaction with another blocked amino acid derivative, reaction maintenance and pooling steps provides a complex mixture of oligopeptides having the desired number of amino acid residues in length, with each amino acid utilized being present in equal molar amounts of each residue at each position in the oligopeptide chain.

These n-mer oligopeptides are cleaved from the solid support, e.g., resin, using various methods such as conventional hydrogen fluoride/anisole procedures; see, e.g., Houghten et al., *Intl. J. Peptide Protein Res.*, 16:311–320 (1980).

To consider a process utilized in the invention in detail, the process is described with respect to protocols and chemistry similar to that of the SMPS process referred to before. It will be understood however, as discussed below, that this description is for example only, and that the process can be suitably carried out using other oligopeptide formation protocols and chemistry, and is not limited only to SMPS-type protocols and chemistry.

Considering then the exemplary embodiment, twenty separate porous synthesis containers are prepared, each containing an equal number of moles of functionalized solid support resin. It is important at this step, as in each of the subsequent subdivision steps, that each aliquot contains the same number of moles of resin functional group or coupled peptide derivative, as is appropriate. Thus, where a single lot of functionalized solid support is used, each aliquot contains an equal weight of solid support. Where different lots of functionalized solid support are used, weights of those different supports used are different among the aliquot, but each aliquot contains an equimolar amount of functional group. Thus, weighings should be done as accurately as reasonably possible.

The resin in each packet is separately reacted with a different one of the twenty naturally occurring amino acids. The coupling of the first blocked amino acids to the respective resins is performed with the carboxyl-terminal end of each first amino acid (a first free reactive functional group) reacting and becoming covalently linked to the support resin and the alpha-amino group (the second reactive functional group capable of reacting during the reaction of the other free reactive functional groups) and reactive side chains of the amino acid blocked.

The coupling reactions are typically driven to completion by adding an excess of the blocked amino acids, and each separate reaction carried out under optimal conditions. It is recognized that each coupling reaction requires different reaction conditions and time to provide full completion. Therefore it is understood that some reactions are completed before others. The earlier-completed reactions can be allowed to sit while the other reactions continue to completion, or, if the reaction products might become degraded, they can be removed from the reaction media and maintained under stabilizing conditions.

After completion of the first amino acid coupling, the resin is removed from each container, pooled together with the resins from all of the other containers and mixed thoroughly (substantially homogeneously). The resin mixture is then separated into twenty aliquots of equal weight. As noted above, at this stage, each weighed aliquot contains a mixture of support resin with an equimolar representation of one of the twenty amino acids coupled to the resin. The twenty weighed aliquot mixtures are then each placed into separate porous second containers. Again each aliquot is reacted with an excess of a different one of the twenty naturally occurring blocked amino acids under conditions that drive the coupling reaction to completion. The blocked second reactive functional group, here the α-amino group, can be unblocked before or after pooling, or before or after reenclosure in second containers. Preferably, the protecting group of the second reactive functional group is removed after the reenclosure step.

In one embodiment, the above steps are then repeated for however many cycles are necessary to synthesize the desired length of peptide.

The result can be illustrated by taking three of the samples shown in the Figure as representative for descriptive purposes. Sample 1a is first reacted with alanine, and Sample 2a is first reacted with methionine, and Sample 3a is reacted with threonine, yielding the initial chains of:

1a) resin-ala;

2a) resin-met; and 3a) resin-val.

These three are then mixed, divided, e.g., into three aliquots 4b, 5b and 6b, and separately reacted respectively with, arginine, serine, and lysine, yielding three mixtures of 2-mer peptide chains as follows:

1b) resin-ala-arg, resin-met-arg and resin-val-arg;

2b) resin-ala-lys, resin-met-lys and resin-val-lys; and 3b) resin-ala-ser, resin-met-ser and resin-val-ser.

The total number of different oligopeptides will be seen to be $X^n$, where X represents the number of different amino acids in the initial plurality and n is the number of amino acids in each chain. Thus, with the twenty naturally occurring amino acids as the starting plurality, the process results in $20^n$ different peptide sequences. For example, a chain with a length of six amino acid residues results in $20^6=64,000,000$ different oligopeptide sequences.

Mixtures of peptides can be synthesized with mixtures of at least six to all twenty amino acids or to include D-amino acids or L-, D- or symmetric amino acids at all positions in the sequence but one, with a fixed, single, predetermined amino acid at one position and mixtures in the remaining positions in the peptide chain. An example of a mixture of peptides of this latter sort is the 6-mer peptide mixture pool having alanine in position 1 ($O_1$) and mixtures of residues, $X_{2-6}$, at positions 2–6 so that each $X_n$ represents a mixture of amino acid residues used, yielding a mixture set having 3,200,000 different oligopeptides. The first amino acid can be synthesized on the resin using prior art methods for single amino acid additions, when synthesized N-terminal to C-terminal, and the remaining at least four positions are synthesized using the physical mixing process described herein.

Similarly, one can have a mixture set in which a glutamic acid residue occupies position 3 ($O_3$), and mixed residues at positions 1, 2, 4, 5 and 6 ($X_{1-2}$ and $X_{4-6}$), containing 3,200,000 different peptides. The latter peptide mixture set can be synthesized with a combination of the chemical and physical mixture methodologies at different positions in the overall chain synthesis.

B. Chemical Mixture Process

A subject unsupported set of mixed solid support-coupled oligopeptides can also be prepared by chemical mixture means. Here, instead of physically mixing the reacted amino acid residue-coupled solid supports to form equimolar amounts of mixed residues, the amino acid derivatives are mixed in the reaction medium (chemical mixing step) and reacted together with a deprotected second reactive functional group in a single reaction. The resulting oligopeptide-coupled solid support (resin) obtained after each step thus corresponds to the pools discussed earlier.

Such reactions are discussed in Rutter et al. U.S. Pat. No. 5,010,175 and Geysen's published WO 86/00991 (PCT/AU85/00165) published 13 Feb., 1986, whose disclosures are incorporated by reference. Basically, in both of those methods, and the process discussed hereinafter, the protected amino acid derivatives are mixed in the reaction medium in proportion to their relative coupling constants to each other to achieve equimolarity in coupling and then coupled to the reactive functional groups of the solid support or free second reactive functional group of a deprotected residue to form the positions of the mixtures.

The single, predetermined amino acid residues are then added to separate portions of the sequence of mixtures in a manner as discussed previously. The various sets are then kept separated as further mixture positions are added.

Thus, for example, using X, O and B as previously defined, one can synthesize the mixture set XX-B by separate reactions of the mixed reaction mixture with an intervening deprotection step. After separation into aliquots, deprotection and separate reaction with each desired single, predetermined protected amino acid derivative, the solid support-coupled OXX-B product is obtained.

Changing the order of the above reactions, it is readily seen that the solid support-coupled XOX-B and XXO-B products can be readily formed. Each of those products is then extended by at least two further chemically mixed couplings to form the corresponding at least 5-mer sets having a single, predetermined amino acid residue at a predetermined position of the oligopeptide chain and equimolar amounts of residues at each of the remaining, other positions of the oligopeptide chain.

It should be similarly apparent that longer oligopeptides having the single, predetermined residue further distant from the solid support can also be readily prepared by use of different numbers of reaction/deprotection steps with the chemical mixture of protected amino acid derivatives.

Table 1 below provides the amounts of particular protected amino acid derivatives utilized herein, and by Rutter et al. and Geysen, all protecting groups utilized were N-t-BOC.

TABLE 1*

| Amino Acid | Herein[1] | Rutter et al.[2] | Geysen[3] |
|---|---|---|---|
| Ala | 19 mg | 113 | 32 |
| Asp(Bn) | 33 mg | 238 | 90 |
| Glu(Bn) | 36 mg | 230 | 96 |
| Phe | 20 mg | 177 | 61 |
| Gly | 15 mg | 84 | 27 |
| His(DNP) | 50 mg | 668 | 147(Tsl) |
| Ile | 123 mg | 667 | 51(½H$_2$O) |
| Lys(Cl—CBZ) | 76 mg | 387 | 124(CBZ) |
| Leu | 36 mg | 185 | 55(H$_2$O) |
| Met | 18 mg | 176 | 54 |
| Asn | 37 mg | 171 | 47 |
| Pro | 27 mg | 157 | 42 |
| Gln | 39 mg | 168 | 53 |
| Arg(Tsl) | 82 mg | 286 | 167(Tsl,H$_2$O) |
| Ser(Bn) | 24 mg | 243 | 76 |
| Thr(Bn) | 44 mg | 451 | 83 |
| Val | 72 mg | 510 | 42 |
| Tyr(Br—CBZ) | 60 mg | 485 | 116(Bn) |
| Trp | — | 203 | 78 |

*Parenthesized designations in the left column are used by each group unless another parenthesized protecting group is shown. Bn = benzyl; DNP = dinitrophenyl; Tsl = toluenesulfonyl; CBZ = benzyloxy carbonyl; Cl—CBZ = o-chlorobenzyloxy carbonyl; Br—CBZ = o-bromobenzyloxy carbonyl.
[1]Milligrams (mg) of each protected amino acid derivative present in a chemical mnixture per 1 milliequivalent of resin —NH$_2$ group. Diisopropylcarbodiimide (DIPCD) used as coupling agent. (See Example 2)
[2]Milligrams of each protected amino acid derivative in 6 ml dimethyl formamide (DMF) and 44 ml dichloromethane (DCM). DIPCD used as coupling agent. (U.S. Pat. No. 5,010,175.)
[3]Milligrams of each protected amino acid derivative in 102 ml of DMF. Dicyclohexylcarbodiimide (DCC) used as coupling agent. (WO 86/00991.)

When using Fmoc protecting groups on a cellulose (cotton) solid support, a Fmoc glycine ester is typically first esterified onto the cotton. The remaining available hydroxyl groups are thereafter esterified by reaction of excess acetic anhydride (Ac$_2$O) in the presence of N-methylimidazole (NMI).

After removal of the excess Ac$_2$O and washings, the Fmoc group is removed from the spacer glycine and mixed Fmoc amino acids at 0.3M in DMF are coupled to the support. The mixed Fmoc amino acids typically include all of the naturally occurring amino acids except cysteine. The molar ratios of the Fmoc amino acids in a chemical mixture used herein are shown in Table 2, below, and can also be used with a particulate support such as a resin or bead.

TABLE 2*

| Amino Acid | Mole Ratio |
|---|---|
| Ala | 0.22 |
| Asp(tBu ester) | 0.47 |
| Glu(tBu ester) | 0.62 |
| Phe | 0.35 |
| Gly | 0.20 |
| His(Tr) | 0.72 |
| Ile | 2.51 |
| Lys(tBoc) | 0.59 |
| Leu | 0.48 |
| Met | 0.34 |
| Asn | 1.65 |
| Pro | 0.20 |
| Gln | 2.03 |
| Arg(Mtr) | 1.98 |
| Ser(tBu ether) | 0.80 |
| Thr(tBu ether) | 2.18 |
| Val | 1.85 |
| Tyr(tBu ether) | 0.81 |
| Trp | 0.99 |

*Parenthesized designations in the left column are protecting groups. tBu = t-butyl; Tr = trityl; tBoc = t-butyloxycarbonyl; Mtr = 4-methoxy-2,3,6-trimethylbenzenesulfonyl.

The reactions used for these couplings were basically those of Eichler et al., *Peptide Res.*, 4:296 (1991) and also in U.S. Pat. No. 5,202,418, whose disclosures are incorporated by reference, with the exception that a spacer such as HOCH$_2$C$_6$H$_4$O(CH$_2$)$_3$CO$_2$H of that allowed application was usually not utilized here. These procedures are discussed in greater detail hereinafter.

The previously discussed porous containers are preferably utilized for syntheses at least subsequent to the addition of the single, predetermined amino acid residue. Thus, for a 6-mer whose fourth position is the single, predetermined amino acid residue, the first two mixtures (positions 5 and 6) of the chain) can be added to the solid support in a bulk reaction using two additions with an intermediate deprotection step to form the solid support-coupled peptide XX-B.

That solid support-coupled peptide is then preferably split into aliquots and placed into separate porous containers. After deprotection, each of those containers is then placed in at least six separate reaction media containing each of the same different amino acid derivatives being used to form enclosed solid support-coupled peptides O$_4$XX-B.

Each of the enclosed, solid support-coupled peptides is then placed into the same reaction vessel containing a mixture of at least six different amino acid derivatives for the next coupling, deprotection and coupling reactions. Thus, each of the at least six mixture sets so formed is kept separate with its predetermined, single amino acid residue protected from admixture with the other sets, while maintaining a uniformity of reaction conditions for the addition of the N-terminal three mixture positions.

This chemical mixture process does not provide exact equimolarity as does the physical mixture process described before. For example, U.S. Pat. No. 5,010,175 reported variation from equimolarity in the range of 0.20–0.32 moles and an average of 0.25±0.04, with each amino acid being no more than 0.8 to 1.28 times the desired result. Deviations from equimolarity from that obtained with the physical mixture method of up to about 35 percent have been observed herein with no adverse effect.

Regardless of the deviations from exact equimolarity observed from use of the chemical mixture method, the various oligopeptides required to obtain enhanced binding are present in large enough quantities to be useful in the assay methods discussed hereinafter.

Each of the twenty naturally occurring L-amino acids can be used in either of the above synthetic processes, as can the corresponding D-amino acids and D- and L-forms of non-natural amino acids such as ornithine, norleucine, hydroxyproline and beta-alanine as well as other $C_4$–$C_6$ amino acids so that use of about 50 different D- and L-protected amino acid derivatives is contemplated. Oligopeptides and oligopeptide mixture pools are contemplated that contain all D-amino acid residues and mixtures of both D- and L-forms.

Sets of any of the above mixtures can then readily be reacted with a desired acceptor such as a cellular receptor and then assayed for identification of those sequences that react most strongly with the receptor. This assay process can be repeated as many times as desired with different mixture sets to insure that all reasonable candidates for reaction are assayed.

From the identification of the optimum set sequences for reaction and binding, one can develop appropriate peptides and peptide derivatives to be used for the therapeutic treatments of organism dysfunctions that involved that receptor as an acceptor. A number of pharmaceuticals for the treatment of human, animal and plant diseases can be identified and developed in this manner.

Exemplary assay procedures are discussed in greater detail hereinafter.

A value of the synthetic processes utilized herein lies at least in part in the fact that, since these process provide all possible amino acid sequences in the n-mers in equimolar quantities, and since those sequences are automatically divided into small aliquots of known composition by the identity and position of the single, predetermined amino acid residue, it becomes easy for researchers to quickly and comprehensively react members of each plurality of sets in individual aliquots with the acceptor (receptor) of interest and assay those candidates for the optimum reaction materials. For example, using 18 amino acids at each position of a 6-mer, one need only carry out 108 assays to determine an enhanced binding sequence. This represents a marked advance over prior processes that either required that vast numbers of peptide candidates be separately assayed (a difficult, costly, and time-consuming undertaking) or that one speculate on which type of amino acid residue sequence might be most likely to work, so that sequences of that type could be individually constructed (also time-consuming, and not necessarily likely to actually produce the optimum materials).

C. Termini, Solid Supports and Coupling

In preferred practice, each oligopeptide is coupled to the solid support during synthesis by a selectively severable covalent bond, such as an ester or an amide bond. An ultimately produced oligopeptide mixture set is cleaved (separated or severed) from the solid support and recovered.

As noted earlier, a contemplated oligopeptide set member contains a chain having five to about ten reacted amino acid residue repeating units. More preferably, each oligopeptide contains a chain of about five to about eight reacted amino acid residues. The exemplary oligopeptides discussed in detail hereinafter contain six reacted amino acid residues, and are referred to as 6-mers.

A $C_1$–$C_8$ acyl group is usually bonded to the N-terminus of an oligopeptide used in acceptor binding assays so that an assayed, cleaved oligopeptide is free at the N-terminus of the positive charge a free amino group would provide at near neutral pH values, e.g. about pH 6–8. An acetyl group, a $C_2$ acyl group, is preferred and is often referred to herein as "Ac". Other $C_1$–$C_8$ acyl groups include formyl, propionyl, butyryl, hexanoyl, benzoyl and octanoyl. A $C_1$–$C_8$ acyl group is added by reaction of a corresponding anhydride such as acetic anhydride, acid halide such as octanoyl chloride or by reaction of a suitable activated ester such as N-hydroxysuccinimidyl benzoate.

A $C_1$–$C_8$ acyl group is usually added to a solid support-coupled oligopeptide upon removal of the selectively removable blocking (protecting) group from the second reactive functional group, when that second reactive functional group is an α-amino group. In preferred practice for oligopeptide syntheses, the second reactive functional group is the N-terminal amino group and the selectively removable protecting group is a t-Boc or Fmoc group, as noted before.

Where an oligopeptide mixture pool is coupled to the solid support by an ester group formed from the C-terminal residue, and a C-terminal amide is desired, the oligopeptide set can be severed from the solid support by aminolysis using ammonia. Cleavage of an ester group-bonded oligopeptide from the solid support using HF results in a C-terminal carboxyl group. Cleavage of an amide-bonded oligopeptide from a benzhydrylamine resin solid support with HF results in the formation of a C-terminal amide group [—C(O)NH$_2$], which also is neutral at near neutral pH values.

The containers used for syntheses do not appreciably react chemically with and are substantially insoluble in water, acids such as trifluoroacetic acid and anhydrous hydrogen fluoride, bases such as diisopropylethylamine, and organic solvents such as acetone, benzene, toluene, xylene, ethyl acetate, dimethyl sulfoxide, methylene chloride, chloroform, dimethyl acetamide, N-methyl pyrrolidone, dimethyl formamide and the like. Thus, the container is substantially inert to reaction or dissolution with common laboratory liquids. Suitable containers are preferably prepared from polymerized ethylene, propylene and mixtures thereof. Stainless steel and polytetrafluoroethylene can also be utilized for the container. A container can be in rigid shaped form such as closable cylinders or in flexible form such as the sealable bags used in the SMPS process.

Each container includes a sufficient number of foraminae, pores or openings to permit ready entrance and exit of solvent and solute molecules at the reaction temperature, which is typically that of ambient air in a laboratory. For instance, a container can be prepared from a woven mesh, in which the foraminae are the interstices between the woven fiber. Other suitably inactive perforate or porous materials can also be employed, such as a perforated sheet or a non-woven fabric sheet material, either having equal or unequal foraminae. The container material can be substantially completely foraminous (e.g., being formed substantially entirely from mesh materials) or partially foraminous if desired. Containers can be closed in any suitable manner, such as by sealing with liquid-tight lids, heat sealing, and so forth. Subsequent reopening can be by lid removal, cutting of the sealed container, etc.

The foraminae (pores) are of a size that is smaller than any of the enclosed reactive particles. Exemplary polypropylene mesh is available having in interstices of about 35 about 100 microns. Stated differently, the mesh foraminae are of a size to retain particles that are retained on a 140–400 standard sieve mesh. More preferably, the foraminae are such that particles retained within the foraminae are those that are retained on a 200–400 standard sieve mesh. The foraminae of the containers are large enough to permit draining of all solvents used during a solid phase synthesis within a time period of about five minutes, and more preferably, within a time period of about three minutes, the draining times being measured at the temperature of the organic reaction.

Exemplary foraminous (porous) containers are further described in U.S. Pat. No. 4,631,211, whose disclosures are incorporated by reference.

A container of a synthesis means of this invention encloses a known quantity of solid phase synthesis particles comprised of one or more constituents that includes a covalently linked reactive functional group or a subunit covalently linked to the particle by a selectively severable bond.

Several solid supports containing covalently linked reactive functionalities have been described in the chemical and biochemical literature, and any such support can be utilized so long as the solid support is insoluble in water, in the before-mentioned organic solvents and is substantially chemically inert to the reaction conditions utilized, as discussed before for the containers. The solid support preferably swells in the solvents utilized during the synthesis due to physical, rather than chemical processes.

The solid supports typically fall into one of three general types, each of which is discussed below.

Perhaps the most utilized particles for oligopeptide and oligo- and polynucleotide syntheses are polymerized resins. The polymerized resins are generally in the form of porous beads.

Of the resins, the hydrophobic polymerized styrene cross-linked with divinyl benzene (typically at about 0.5 to about 2 weight percent) resins are the most often utilized, especially for oligopeptide syntheses. The resin beads so prepared are further reacted to provide a known quantity of a benzyl moiety as a portion of the polymerized resin. The benzyl moiety contains a reactive functional group through which the subunits of the sequence to be synthesized may be covalently linked by a selectively severable bond. Although the reactive benzyl moieties are typically added after the resin bead has been synthesized by reaction of a polymerized styrene moiety, such resins are herein generally described as polymerized styrene cross-linked with divinyl benzene and including a known amount of polymerized vinyl benzyl moiety.

The reactive functionality of the benzyl moiety is typically selected from the group consisting of aminobenzyl and halobenzyl such as chlorobenzyl. Polymerized, cross-linked styrene resins containing chlorobenzyl moieties are sometimes referred to in the art as chloromethyl styrene resins, while resins containing aminobenzyl moieties are sometimes referred to as amino-styrene or aminomethyl-styrene resins.

It is noted that the subunit/particle link formed between a particle containing aminobenzyl moiety and a carboxylic acid is not readily cleavable under usual conditions of synthesis. As a consequence, such particles are used with severable linking groups between the particle and first linked subunit, where a free subunit reaction product is desired to be recovered.

Additional useful resin particles are those materials referred to by East et al., *J. Immunol.*, 17:519–525 (1980) as macroreticular resins. Those resins are said to be prepared from cross-linked polystyrene and to include a reactive aminobenzyl moiety. The described resin particles contain pores of a large enough cross-section to permit entry of antibodies and immunoreaction of those antibodies with the synthesized oligopeptide. The macroreticular resins were reported to be obtained from Rohm & Haas under the trademark designation XE-225A.

Resins containing a known amount of chlorobenzyl moieties can be purchased from Sigma Chemical Co., St. Louis, Mo. under the trademark names Merrifield's peptide Resin (chloromethylated co-polystyrene divinylbenzene). Such materials are typically supplied containing about 0.1 to about 2 milliequivalents of chlorine per gram of particle.

The aminobenzyl group can be prepared from polymerized styrene cross-linked with divinyl benzene by reaction with N-(hydroxymethyl)phthalimide under Friedel-Crafts conditions followed by hydrazinolysis of the phthalimide group as is described by Kent et al., *Israel J. Chem.*, 17:243–247 (1978). Particles containing reactive aminobenzyl moieties are also commercially available from Pierce Chemical Company of Rockford Ill. and are reported to contain about 0.3 to about 0.7 millimoles of aminobenzyl moiety per gram of particles.

Intermediate linking groups between the reactive benzyl moiety and the first of a sequence of subunits may also be employed as is the case of the 4-(oxymethyl) phenylacetyl group bonded to an amino benzyl moiety reported by Kent et al., above. Another linking group is the 4-(oxymethyl)phenoxy group bonded to a benzyl moiety as reported by Meienhofer et al., *Int. J. Peptide Protein Res.*, 13:35–42 (1979).

The above-described polystyrene-based particles are frequently used in the synthesis of oligopeptides in which the carboxyl-terminal amino acid residue (subunit) is bonded through a selectively severable covalent bond to the polymerized, reactive vinyl benzyl moiety of the resin. Benzyl ester bonds between the polystyrene-based particle and subunit are stable in the presence of relatively mild acids, but sever when treated with strong acids such as hydrofluoric acid or a mixture of acetic and hydrobromic acids. Oligopeptide syntheses are typically carried out using mild acid- or base-sensitive protecting groups on the alpha amino groups such as N-tert-butoxycarbonyl (t-Boc) or 9-fluorenylmethyloxycarbonyl (Fmoc), while using other, strong acid-sensitive protecting groups on reactive side chains. The photosensitive nitroveratryloxycarbonyl (NVOC) amino-protecting group can also be used.

One of the difficulties in working with large quantities of synthetically prepared oligopeptides relates to the usual practice of using anhydrous hydrogen fluoride (HF) to sever the synthesized oligopeptide reaction product and its side chain protecting groups from the solid support. Hydrogen fluoride is not an easy material to work with and must be handled with great care. In addition, since HF severs both the oligopeptide from the particle and side chain protecting groups from the oligopeptide, the severed oligopeptide must be purified from the side chain protecting groups.

A disulfide-containing linking group that can be bonded to a benzylamine of a before-described resin particle may be utilized to alleviate some of the difficulties encountered in using HF to sever the oligopeptide reaction product and to remove side chain protecting groups. A precursor to that linking group is represented by the formula:

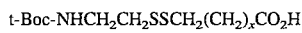

t-Boc-NHCH$_2$CH$_2$SSCH$_2$(CH$_2$)$_x$CO$_2$H wherein t-Boc is tert-butoxycarbonyl, and x is a numeral having the value of zero or one, such that when x is zero, the parenthesized CH$_2$ group is absent.

The carboxyl group of the linking group is bonded to the amino group of a polymerized vinyl benzyl moiety of a reactive resin-containing particle using standard peptide amide bond-forming techniques such as via the anhydride, with dicyclohexylcarbodiimide or another carbodiimide.

The t-Boc group is thereafter removed using mild acid as is well known, the resulting ammonium salt is neutralized to provide a free primary amine and the resulting free primary amine-containing particles are rinsed to remove any excess base-containing reagent used in the neutralization step.

The first amino acid subunit is thereafter coupled through its carboxylic acid group to the free primary amine to form a particle-linked subunit. The amino acid residue is linked to the resin through an amide bond between the carboxyl group of the amino acid and the amino group of the disulfide-containing linking group that is itself bonded by an amide bond to the polymerized vinyl benzyl moiety of the resin. The resulting linking group, written in the direction from left to right and from the amino acid residue toward the benzyl moiety, is represented by the formula:

—NHCH$_2$CH$_2$SSCH$_2$(CH$_2$)$_x$CONH where x is as before-described.

The linking group with any amino acid that may be designated "Z" coupled through its carboxyl group and with the particle bonded through its polymerized vinyl benzyl moiety may be written as described above:

Z—NHCH$_2$CH$_2$SSCH$_2$(CH$_2$)$_x$CONH-Particle.

A particular benefit of using the above-described linking group is that its amide and disulfide bonds are stable to contact with HF and other strong acids used to selectively remove amino acid side chains. Consequently, such acids can be used to remove the side chains of the oligopeptide reaction product while that reaction product is still linked to the resin particle. That selective removal permits the removed side chain protecting groups to be rinsed away from the reaction product-linked resin particle and thereby provides easier purification of the oligopeptide reaction product.

The oligopeptide-linked resin particle is thereafter contacted with a disulfide bond-breaking agent to selectively sever the oligopeptide reaction product from the resin particle. The severed oligopeptide reaction product can thereafter be recovered in relatively pure form using standard procedures such as extraction of the severed reaction product/particle mixture formed with an aqueous composition containing 5 percent acetic acid. The extracted composition can thereafter be lyophilized to provide the reaction product. The reaction product can also be further purified as is known prior to its ultimate recovery.

Several reagents are well known to be useful for breaking the disulfide bond. Exemplary reagents include sodium borohydride, 2-mercaptoethanol, 2-mercaptoethylamine, dithiothreitol and dithioerythritol. Mercaptan-containing carboxylic acids having two to three carbon atoms and their alkali metal and ammonium salts are also useful. Those reagents include thioglycolic acid, thiolactic acid and 3-mercaptopropionic acid. Exemplary salts include sodium thioglycolate, potassium thiolactate, ammonium 3-mercaptopropionate and (2-hydroxyethyl)ammonium thioglycolate.

The disulfide-containing t-Boc-protected linking group precursor may be prepared by standard techniques. For example 2-aminoethyl disulfide may be reacted with two moles of 2-(tert-butoxycarbonyloxylmino)-2-phenylacetonitrile or N-(tert-butoxycarbonyloxy)-phthalimide or a similar reagent to form bis-N-t-Boc-2-aminoethyl disulfide. That disulfide can then be reacted with thioglycolic acid or 3-mercaptopropionic acid to form the precursor shown above.

A relatively newer group of resin particles has been reported by E. Atherton and co-workers. Those particles are based upon copolymers of dimethyacrylamide cross-linked with N,N'-bisacryloylethylenediamine, including a known amount of N-tert-butoxycarbonyl-beta-alanyl-N'-acryloyl-hexamethylenediamine. Several spacer molecules are typically added via the beta-alanyl group, followed thereafter by the amino acid residue subunits. See Atherton et al., *J. Am Chem. Soc.*, 97:6584–6585 (1975).

The β-alanyl-containing monomer can be replaced with an acryloyl sarcosine monomer during polymerization to form resin beads. The polymerization is followed by reaction of the beads with ethylenediamine to form resin particles that contain primary amines as the covalently linked functionality. See Atherton et al., *Bioorga. Chem.*, 8:351–370 (1979) and Atherton et al., *J. C. S. Perkin I*, 538–546 (1981).

The polyacrylamide-based resin particles are relatively more hydrophilic than are the polystyrene resin particles and are usually used with polar parotic solvents. Exemplary solvents include dimethylformamide, dimethylacetamide, N-methylpyrollidone and the like.

The base-sensitive α-amino protecting group N-9-fluorenylmethyloxycarbonyl (Fmoc) can be used in conjunction with the polymerized dimethylacrylimide-based resins as well as the cross-linked sytrene/amino benzyl resin particles and a cellulose solid support such as cotton. See Atherton et al., *J. C. S. Perkin I*, 538–546 (1981) and Meienhofer et al., *Intl. J. Peptide Protein Res.*, 13:35–42 (1979).

A second group of solid supports is based on silica-containing particles such as porous glass beads and silica gel. For example, Parr and Grohmann, *Angew. Chem. Internal. Ed.*, 11, 314–315 (1972) reported on the use of the reaction product of trichloro-[3-(4-chloromethyl)phenyl] propylsilane and porous glass beads (sold under the trademark PORASIL E by Waters Associates, Framingham, Mass.) as solid support for oligopeptide syntheses. Similarly, a mono ester of 1,4-dihydroxylmethylbenzene and a silica (sold under the trademark BIOPAK by Waters Associates) was reported to be a useful solid support for oligopeptides syntheses by Bayer and Jung, *Tetrahedron Lett.*, 4503–4505 (1970). Each of the above solid supports is seen to utilize a reactive benzyl moiety through which the subunit was bonded to the particle.

The third general type of useful solid support may be termed "composites" in that they are constituted by two major ingredients, a resin and another material that is also substantially inert to the organic synthesis reaction conditions employed.

One exemplary composite described by Scott et al., *J. Chrom. Sci.*, 9:577–591 (1971), utilized glass particles coated with hydrophobic, polymerized, cross-linked styrene containing reactive chloromethyl groups. Another exemplary composite was reported to contain a core of fluorinated ethylene polymer onto which was grafted linear polystyrene. See Kent et al., above, and van Rietschoten, in *Peptides 1974*, Y. Wolman ed., 113–116 (1975).

General reviews of useful solid supports (particles) that include a covalently linked reactive functionality may be found in Atherton et al., *Perspectives in Peptide Chemistry*, Karger, 101–117 (1981); Amamath et al., *Chem. Rev.*, 77:183–217 (1977); and Fridkin, *The Peptides*, Volume 2, Chapter 3, Academic Press, Inc., (1979), pp. 333–363.

A porous container can also be provided that encloses a known amount of particles having a known amount of single amino acid residue repeating units linked thereto by selectively severable covalent bonds. Each of such amino acid residues, that is farthest from (distal to) the particle/repeating unit link contains a functional group capable of reacting during the organic synthesis but that is protected from so reacting by a selectively removable, covalently linked protecting group.

Particle-linked, selectively severable amino acid residue repeating units that themselves contain protected reactive functional groups are provided in known amounts linked to the particles by the manufacturer. For example, resin particles of polymerized styrene cross-linked with divinylbenzene and including a known amount of polymerized vinylbenzyl moiety that contain linked amino acid residues having protected reactive functionalities such as N-t-butoxycarbonyl-protected α-amino (t-Boc-protected) groups are provided by several suppliers. Each particulate material is supplied with a statement as to the amount of linked amino acid residue present in the particles.

Another useful synthetic technique, particularly for use in the chemical mixture process, is the process described in the Lebl et al. U.S. Pat. No. 5,202,418, whose disclosures are incorporated herein by reference.

Briefly, a planar circular disk is provided having a circular path defined around the disk. The disk is divided into a plurality of individual compartments, each containing an inert porous material such as cotton cloth as a solid support. The compartments are spaced circumferentially along the circular path defined around the disk. At least one functional group for synthesis of an oligopeptide is anchored onto the porous material to form a plurality of individual functionalized compartments.

A dosing head is arranged at a fixed location adjacent the circular path. The dosing head includes means for directly applying measured quantities of at least one liquid component from a common reservoir of the component such as the individual amino acid derivatives or a chemical mixture thereof.

The disk is positioned so that one of the functionalized compartments is positioned to receive a liquid component directly applied by the dosing head. A measured quantity of a liquid component is directly applied to the individual functionalized compartment from the reservoir via the dosing head. The applied liquid component provides an amino acid derivative or mixture to form a covalent bond with the functional group of the functionalized compartment.

The disk is rotated to position another individual compartment along the circular path to receive the same or another liquid component from the dosing head. After the amino acid derivative(s) of each applied liquid component has reacted, or after all have reacted, the disk is spun to centrifugally separate the liquids from the reacted solid support.

A deprotection step follows, followed by further additions of liquid component, reaction, and centrifugation. Those steps are repeated until an oligopeptide of the desired length is prepared.

It should be apparent from the above discussion that the mixture positions of an oligopeptide set can readily be prepared by use of mixed amino acid derivatives. It should be similarly apparent that the single, predetermined amino acid derivative can be similarly added at its predetermined position.

An ester group is typically utilized to link the oligopeptide to the solid support with Fmoc protecting groups. The synthesized oligopeptide is then cleaved with trifluoroacetic acid.

The Oligopeptide Sets

A complex mixture pool of solid support-coupled oligopeptides described hereinbefore once cleaved or severed from the solid support is referred to herein as an oligopeptide set, an oligopeptide mixture set, by a similar phrase, or more simply as a "set", as well as being sometimes referred to herein as a synthetic peptide combinatorial library. Being severed from the solid support, an oligopeptide set is unsupported, and because of its method of synthesis, such a set is linear.

Contemplated by the invention are a plurality sets of self-solubilizing, unsupported mixed oligopeptides. Each set consists essentially of equimolar amounts of linear oligopeptide chains containing the same number of five to about ten amino acid residues in each chain. Each set, and its members, have a single, predetermined amino acid residue e.g. Ala, D-Glu, β-alanine etc., at a singly predetermined position of the oligopeptide chain, e.g. positions 1, 2, 3 . . . 10 from the amino-terminus. Each set also has equimolar amounts of at least six, preferably at least 10, and more preferably about 15 to about 20, different amino acid residues at the same other positions in the oligopeptide chain.

Thus, each of the plurality of sets has equimolar amounts of at least six different amino acid residues at the positions other than that of the single, predetermined amino acid present at the predetermined chain position. Each of the plurality of sets differs from the other sets by the single, predetermined amino acid at the predetermined chain position.

The single, predetermined amino acid at the predetermined chain position is utilized in the equimolar mixture of amino acid residues present at those other positions. If that single, predetermined residue is not present in the mixture positions, the binding assay results as to that residue become meaningless as to that residue.

Each set of a plurality of sets contains equimolar amounts of its mixed oligopeptides. That equimolarity is provided by the synthesis method used, as discussed before. For a given set such as a 6-mer, using the 20 natural amino acids as building blocks, there are 3,200,000 separate oligopeptides [1(defined position) times (5 mixture positions, each with 20 residues or $20^5$)].

It is presently impossible to assay a mixture of such complexity. However, by using the synthetic methods discussed before, a skilled worker can construct a mixed oligopeptide, which upon hydrolysis and amino acid analysis has molar ratios of each amino acid to each other in the range of about 0.5 to about 1.5; i.e., the molar ratio of one amino acid residue to any other residue is 1:1± about 0.5, more preferably, this ratio is 1:1± about 0.25.

Each chain of a set is also present in an equimolar amount and is of the same length (contains the same number of residues) compared to the other chains present in the set. This equimolarity is also impossible to measure directly. However, by carrying out each reaction to completion and maintaining the previously discussed equimolarity, one can prepare chains that are of the same length and present in equimolar amounts.

The oligopeptides of a set contain the same number of 5 to 10 residues (5- to 10-mers), and more preferably 5 to about 8 residues in each chain. Chain lengths of six residues (6-mers) are preferred. Whatever length is selected, each set and its member chains is the same length.

A chain of greater length, up to about 50 residues can be used, but the remaining 45 to 40 residues at one terminus, the other, or apportioned between the termini are predetermined, constant sequences. In one example, the 35-residue chain of β-endorphin can comprise the carboxy-terminus of all of the members of the set. In another example, a 12-mer is prepared whose six, central residues are known and that contains two amino-terminal and three carboxy-terminal mixture positions, with the third position from the N-terminus being the predetermined residue position.

Each set of mixed oligopeptides has the same single, predetermined amino acid residue at the same single, predetermined position in the oligopeptide chain. The remaining positions of the oligopeptide chain of the set are occupied by an equimolar amount of at least six different amino acid residues.

For example, using glycine (Gly) at position 1 (the N-terminus) of a 5-mer, and the six different amino acid residues being Gly, Phe, Ala, Met, Glu and Lys, one exemplary set is composed of 4096 ($4^6$) different member oligopeptide chains, each starting with Gly and having equimolar amounts of each of Gly, Phe, Ala, Met, Glu and Lys at each of the remaining four positions of the oligopeptide chain. Another set has Phe at the 1-position and include 4096 different member sets having equimolar amounts of Gly, Phe, Ala, Met, Glu and Lys at each of the other positions. The same can be said for each of the sets having Ala, Met, Glu or Lys at position 1 of an oligopeptide chain.

The above exemplary sets are usually equal in number to the number of different amino acid residues present at the mixed positions. Additional members can include residues not present in the mixtures at the termini, particularly at the N-terminus. Those sets constitute one plurality of sets, each set having a single, predetermined position in the chain (the 1-position) and equimolar amounts of the same six different amino acid residues at the remaining positions of the oligopeptide chain (positions 2–5). Of course one can opt to use fewer than the maximum number of sets.

Another plurality of sets is similarly defined for each of the remaining positions along the oligopeptide chain. For each of those remaining sets, the 1-position is occupied by an equimolar amount of the at least six different amino acid residues that comprise the mixture.

In more preferred practice, the number of amino acid residues for the mixture positions, and thus the number of different sets, is at least ten. Most preferably, that number is 15–20. It is particularly preferred to use 18 (t-Boc-synthesized) or 19 (Fmoc-synthesized) sets for each plurality of sets; i.e., the naturally occurring 20 amino acids are used except cysteine that tends to cross-link and tryptophan that is difficult to couple and can also cross-link.

It is thus seen that each set of a first plurality of sets differs from the other sets in that first plurality of sets by the identity of the one of at least six predetermined residues at the predetermined position. That first plurality of sets differs from another plurality of sets by the position of the one of at least six predetermined amino acid residues in each of the sets of the other plurality.

Thus, using a 6-mer as exemplary, the positions of predetermined, single residue and positions of equimolar mixtures of residues are shown below.

| Predetermined Positions | Mixture Positions |
| --- | --- |
| 1 | 2, 3, 4, 5, 6 |
| 2 | 1, 3, 4, 5, 6 |
| 3 | 1, 2, 4, 5, 6 |
| 4 | 1, 2, 3, 5, 6 |
| 5 | 1, 2, 3, 4, 6 |
| 6 | 1, 2, 3, 4, 5 |

There is thus one set of peptides for each of the single, predetermined amino acid residue at position 1. Because at least six amino acid residues are used in the mixture positions and each of those is also used at position 1, the number of the plurality of position-1 sets is six. The same is true for each of the other positions. The sets defined by the position of the single, predetermined amino acid residues can be referred to as positional sets.

These sets of 6-mers can also be referred to as 5× sets because of their five mixture positions. Where the peptides are five residues long or have four mixture positions, the sets can be referred to as 4× sets, and so on.

Because there are six positions in the 6-mer, the number of the plurality of plurality of sets for the above group of positional sets is 6 times 6 or 36. There are, however, $6^6$ or 46,656 total oligopeptides represented by that plurality of set pluralities. Use of 20 amino acid residues for the mixture positions of a 6-mer provides 6 times 20 or 120 positional sets, and a total of 64,000,000 individual oligopeptides.

As noted before, where residues are not included in the mixtures, those residues also normally do not occupy the position of a single, predetermined residue. Exceptions here occur at the N- and C-termini where residues not in the mixtures such as Cys and Trp have been found to provide useful results.

The cleaved, unsupported oligopeptides are also referred to as being "self-solubilizing". Self-solubilization is an unexpected phenomenon observed with these oligopeptide mixtures in that they exhibit a solubility in aqueous media that is unexpectedly high, particularly when hydrophobic residues are utilized. The nature of the interactions leading to the observed enhanced solubility is unknown. However, so long as cysteine or cystine are absent from the sequences, the mixed oligopeptide sets such as those preferred sets prepared from mixtures of 18 residues appear to be quite soluble, as is also noted elsewhere herein by the concentrations of mixed sets that can be utilized.

Optimal or preferential acceptor binding studies can be carried out for each of the sets that varies at each position of the oligopeptide chain. Where the above 6-mers are used, with each of the twenty natural amino acids at each predetermined position "O" in the chain, 120 assays are required. The residue, "O", of the twenty present that exhibits optimal (best or preferential) binding at each position of the chain in those assays defines the residue at that position of an optimal or preferential oligopeptide donor. The sequence of an optimal or preferential binding donor is then determined from the optimal or preferential binding results obtained for each sequence position along the oligopeptide mixture set chain.

Thus, as the data discussed and provided hereinafter show, a scanning SPCL assay can provide a single, optimal binding sequence. Often, several residues at several positions provide similar results. Those similar results can narrow the field of possible best binding sequences for a 6-mer from 64 million to a few thousand or fewer than one hundred, such as about 5 to about 50 sequences. The data thus obtained can then be used to prepare specific 6-mers, for example, based upon combinations of several preferential binding residues at several positions.

It is often preferred that one or both termini of an oligopeptide mixture pool set have amide bonds. To that end, it is preferred that the second reactive functional group of the last added protected amino acid derivative be removed while the complex mixture pool is coupled to the solid support and that the resulting free reactive functional group be reacted to form amide bonds on all of the coupled oligopeptides. A before-described $C_1$–$C_8$ acyl group such as an acetyl group is preferably used to form the amide bond at the N-terminus. An amide bond can also be formed when a carboxyl group is the second reactive functional group, or the first reactive functional group, as discussed previously. Each oligopeptide mixture set is preferably prepared and used an as a N-acetyl C-amide derivative mixture set, and can be represented as Ac-sequence-NH$_2$.

It can also be useful for an oligopeptide mixture set to include a label. A radioactive label such as $^3$H can be used as part of an N-terminal acyl group such as an acetyl group.

Other contemplated labels include chromophores such as the 2,4-dinitrophenyl or 4-nitrophenyl groups and fluorescent molecules such as a dansyl group that can be coupled to an N-terminal amino group using dansyl chloride (5-dimethylamino-1-naphthalenesulfonyl chloride) after cleavage of the terminal blocking group.

A 2,4-dinitrophenyl or 4-nitrophenyl group can be coupled to a deprotected terminal amine of a solid support-bound oligopeptide mixture by means of an appropriate halogen derivative such as a chloro or fluoro group. The resulting nitrophenyl aniline derivatives have a yellow to yellow/orange color that can be readily observed.

It is also contemplated that a photoreactive label be coupled to an oligopeptide mixture set, particularly at the N-terminus. Exemplary photoreactive labels include the 4-azidobenzoyl and 4-azidosalicyl groups that are present as N-terminal amides prepared by reaction of the N-hydroxysuccinimide ester of either group with the free, N-terminal amino group. Each of the esters is available from Sigma Chemical Co., St. Louis, Mo.

As noted from the foregoing discussion, a plurality or set of oligopeptide mixture sets is also contemplated. Each set of the plurality has the same sequence of one predetermined amino acid residue at one predetermined position of the oligopeptide chain and the same sequence of equimolar amounts of at least six different amino acid residues at the remaining positions in the oligopeptide chain. The sets of oligopeptide sets differ in that one predetermined residue present at a predetermined position within each set is different between the sets.

The number of sets within the set of sets is determined by the number of different amino acid residues utilized at the above, single remaining position. Thus, where the twenty naturally occurring amino acid residues are used, each set would contain 20 members of mixtures. The number of individual oligopeptides in each mixture set is determined by multiplying the numbers of residues used at each equimolar mixture position.

The previously discussed 120 oligopeptide mixture sets of 6-mer sets each containing one predetermined position and five mixture positions illustrate six sets of twenty oligopeptide mixture sets. Each set contains a sequence length of six amino acid residues. One position in each set is occupied by one of a plurality of the predetermined at least six different amino acid residues utilized for that position. The remaining five positions of each set are occupied by equal molar amounts of those at least six different amino acid residues. Again, the number of members of each set is determined by the number of predetermined residues utilized, except at the termini, and the number of oligopeptides in each member set is determined by multiplying the number of residues utilized at each equimolar mixture position by the number of the next position and so on. Because the same number is typically used at each position, the number of oligopeptides present is the number in the mixture to the power that is the number of mixture positions. For a 6-mer with 20 different residues at five positions, the number is $20^5$.

Processes and Oligopeptides

The present invention contemplates a process for providing the amino acid residue sequence of an oligopeptide ligand that preferentially (optimally) binds to an acceptor. In accordance with this process, (a) a plurality of sets of self-solubilizing, unsupported mixed oligopeptides in which each set consists essentially of a mixture of equimolar amounts of linear oligopeptide chains containing the same number of five to ten amino acid residues in each oligopeptide chain is provided. As discussed previously, the members of each set have one of at least six different predetermined amino acid residues at a single, predetermined position of the oligopeptide chain, and each set has equimolar amounts of those same at least six different amino acid residues at the same other positions of the oligopeptide chain. The plurality of sets has equimolar amounts of at least six different amino acid residues at the other positions in the oligopeptide chain, but differ in that the single, predetermined amino acid residue present at the predetermined chain position within each set is different between the sets.

(b) Each set from the plurality of sets is separately admixed with the acceptor in an aqueous medium at a set concentration of about 0.1 milligrams per liter to about 100 grams per liter and preferably about 1 milligram per liter to about 100 grams per liter. The binding of each set to the acceptor is separately assayed, and the one or more sets of the plurality of sets that provided preferential binding compared to the other sets assayed is determined.

(c) Another plurality of sets of self-solubilizing, unsupported mixed oligopeptides is provided in which each set consists essentially of a mixture of equimolar amounts of linear oligopeptide chains containing the same number of five to ten amino acid residues in each oligopeptide chain and having the same chain length as the first named plurality of sets. The members of each set have one of at least six different predetermined amino acid residues at another single, predetermined position of the oligopeptide chain different from the position of the first plurality of sets, and each of these sets has equimolar amounts of the same at least six different amino acid residues at the same other positions of the oligopeptide chain. This other plurality of sets has equimolar amounts of at least six different amino acid residues at the other positions in the oligopeptide chain but differs from the first plurality of sets in that the single, predetermined chain position within each set that contains the one of at least six different residues is different between the sets. For example, the above plurality of sets can have its one of at least six different, predetermined amino acid residues at position 1 whereas this plurality of sets has its single, predetermined amino acid residue at any of positions 2–5.

(d) Each set from the other plurality of sets (of step c) is separately admixed with the acceptor in an aqueous medium at a concentration of about 0.1 milligrams per liter to about 100 grams per liter and preferably about 1 milligram per liter to about 100 grams per liter. The binding of each other set to the acceptor is seaprately assayed and the one or more sets of this other plurality of sets that provides preferential binding compared to the other sets assayed is determined, as discussed before.

(e) Steps (c) and (d) are repeated until the desired number of set pluralities (typically at least five for a 5-mer) have been assayed, each of those set pluralities differing from the other pluralities by the position that contains the one of at least six different amino acid residues.

The identity and position of the amino acid residue of each one or more sets that provided preferential binding so determined for each plurality of sets provides an amino acid residue sequence for the ligand that preferentially binds to the acceptor. Thus, because each of the pluralities of positional sets assayed provides the identity of a residue(s) that provide(s) enhanced binding for that position, and because there is equimolar representation of all the other residues at the mixture positions, knowledge of the identity and position of residues that provide enhanced binding for at least five positions provides a sequence for a ligand or donor that provides enhanced binding.

It should be understood that determining the identity and position of two residues that each provide greatly enhanced binding can be extremely useful when preparing completed peptides because several fewer such peptides need be prepared. Of course, knowledge of three identities and positions is more preferred, and knowledge of four is more preferred still.

The above process is referred to as a scanning synthetic peptide combinatorial library (SPCL) process in that residues at each position of a sequence are individually scanned.

It should be understood that one need not utilize the pluralities of sets in any order by position. Thus, although convenient, one need not use the plurality of sets that contain the one of at least six different predetermined residues at position 1 followed by the sets having the one of at least six different predetermined residues at position 2, and so on.

In addition to there being no need to utilize the pluralities of positional sets in any order, it is also not necessary to utilize a single plurality of positional sets followed by another and another, etc. Rather, one can utilize the individual sets in any order because the position of the one of at least six different predetermined amino acid residue of each set is known.

Thus, a more general scanning SPCL process is also contemplated. Here, (a) separate pluralities of sets of self-solubilizing, unsupported mixed oligopeptides are provided. Each set of those pluralities of sets consists essentially of a mixture of equimolar amounts of linear oligopeptide chains containing five to about ten amino acid residues in each chain. Each set has one of at least six different predetermined amino acid residues at a single, predetermined position of the oligopeptide chain, and has the same at least six different amino acid residues at the same other positions of the oligopeptide chain. Each set differs from the other sets in that the identity and chain position of the one of at least six different predetermined amino acid residues present at the predetermined chain position within each set is different between the sets. The maximum number of sets provided is equal to the product of the number of different amino acid residues present at the predetermined chain positions containing the one of at least six different residues times the number of different chain positions containing the one of at least six different predetermined amino acid residues.

(b) Each set is separately admixed with the acceptor in an aqueous medium at a set concentration of about 0.1 milligrams per liter to about 100 grams per liter and preferably about 1 milligram per liter to about 100 grams per liter and the binding of each set to the acceptor is separately assayed for each set. The one or more sets that provided preferential binding for each different chain positions is determined.

The identity and position of the amino acid residue of each one or more sets that provided preferential binding provides the acid residue sequence for the ligand that preferentially binds to the acceptor.

At least five pluralities of positional sets are typically utilized (scanned). It is preferred, but not necessary, that those five pluralities of sets contain single, predetermined residues at adjacent positions in the sequence. For example, in a 5-mer, those positions would be 1–5 of the sequence. However, in a 10-mer, those positions could be positions 6–10, 5–9, 3–7 or the like. Of course, one obtains more precise sequence identification information if adjacent positions of the oligopeptide chain are determined, and if the identity of the residue providing enhanced binding for each chain position is determined.

The length of the oligopeptide chain is that described previously. Again, chains six-residues long are preferred.

Similarly, the previously noted preferences for an N-terminal $C_1$–$C_8$ acyl group and a C-terminal amide group are preferred for use in an above process. This is particularly true where the natural ligand is a protein or large polypeptide. However, where the natural ligand or donor is a peptide as is the case with enkephalins, free N-terminal amino groups and C-terminal carboxyl groups are preferred.

As is illustrated hereinafter, use of an above process can identify a single sequence that exhibits not only preferential binding to an acceptor, but also optimal or best binding to that acceptor. Often, however, one or more residues at a given position provide similar preferential binding.

Those identified residues that exhibit preferential binding within about a factor of two of the best binding residues at that position are typically used to prepare a series oligopeptides using the other identified residues at the other positions to determine which combination provides the best overall properties. Thus, using a 6-mer as exemplary, although one may not be able to determine the single best sequence out of the 64,000,000, the field is typically cut down to about 5–50 or sometimes thousands of sequences, which because of their sequential similarity, can be readily prepared by the SMPS method discussed in U.S. Pat. No. 4,631,211. Even where the scanning SPCL process narrows the possible optimal binding peptide sequences to several thousand, the worker's knowledge has been advanced, and he or she can use a method described in WO 92/09300, or Houghten et al., *Nature*, 354:84 (1991), in U.S. Pat. No. 5,010,175 or in WO 86/00991 to complete the sequence or obtain new optimal binding sequences.

In other instances, all of the at least six different predetermined residues at a predetermined position can provide similar binding. That phenomenon is referred to as positional redundancy or redundancy, and any convenient residue is utilized at that position when an oligopeptide ligand is synthesized.

The aqueous medium used in an assay can be extremely varied and includes tap water, distilled or deionized water, as well as a buffer solution as is used for antibody binding studies or a cell growth medium as is useful for bacteria, plant or animal cells, all of which are well known to skilled workers.

The concentration of an oligopeptide mixture set in the aqueous medium is selected so that the mixtures of the oligopeptide set are present at concentrations of about 0.1 milligrams per liter to about 100 grams per liter and preferably about 1.0 µg/ml to about 100 mg/ml. Thus, when each oligopeptide mixture is made up of 3.2 million individual oligopeptides; i.e., an N-acetyl C-amide 6-mer using the 20 natural amino acid residues, then each peptide within each mixture is present in a preferred concentration of about 1.0 µg/ml/3,200,000=0.31 pg/ml, to about 100 mg/ml/3,200, 000=31.25 ng/ml. Presuming an average molecular weight of an N-acetyl C-amide 6-mer to be 785 gm/mole, then at 1.0 μg/ml, the individual hexamers are present at a concentration of about 0.4 pmolar and at 100 mg/ml the individual hexamers are present at about 40 nmolar. More preferably, concentrations of about 0.5 mg/ml to about 10 mg/ml are used. It is to be understood that the wide breadth of concentrations specified above is intended to take into account the contemplated range of oligopeptide mixture sets that can have up to nine positions as mixtures, and the fact that wide ranges of concentrations are used for determining $IC_{50}$ and $K_i$ values.

An oligopeptide mixture set and its individual members can be looked at as donor (ligand) in donor-acceptor binding complex formation. Exemplary acceptor molecules are antibody combining site-containing molecules such as whole antibodies, F(ab), F(ab')$_2$ and Fv antibody portions, solubilized or non-solubilized cell surface receptor molecules, internal cellular receptors and viral protein receptors, all but the antibody combining site-containing molecules being collectively referred to as "cellular receptors". "Cellular receptors" includes living cells that contain receptors that interact with an oligopeptide set as ligand (donor).

An oligopeptide ligand can also bind to an acceptor molecule that is itself otherwise considered to be a ligand. For example and without wishing to be bound by theory, in the hemolysis inhibition studies discussed hereinafter using melittin as the lysing agent, it is believed that the oligopeptide sets and synthesized individual peptides bind to the melittin and thereby inhibit its lysis of red blood cells (RBC). Thus, melittin that would otherwise be considered a donor for an acceptor on RBC appears to function as an acceptor.

Any well known binding or binding inhibition assay format can be used. For example, a solid phase assay using a solid phase-bound antibody binding site and a radiolabeled oligopeptide mixture set is contemplated. Also contemplated is a competitive binding assay in which a protein or polypeptide is bound to a solid phase as an antigen and a monoclonal antibody binding to that antigen is admixed with an oligopeptide mixture set. Inhibition of binding of the monoclonal antibody by the oligopeptide mixture set provides a measure of the binding between the oligopeptides and monoclonal antibody. Monoclonal antibody binding inhibition and the inhibition of other acceptors' binding can be assayed using enzyme or radiolabels as is well known.

It is often the case that one has receptors such as antibodies to a particular ligand such as an antigen, but the specific ligand (antigen) that binds those antibodies is unknown. Under these circumstances, usual solid phase assay in which the ligand is affixed to a plate or other solid phase matrix cannot be carried out because the relatively short oligopeptide sets contemplated herein do not bind well to microtiter plate walls and similar solid phase matrices.

Avidin binds well to microtiter plate walls and similar matrices. Use of that fact and its well known binding partner, biotin, can be made for those assays in which the ligand bond by the receptor is unknown or is otherwise unavailable.

Thus, avidin is coated on a solid phase matrix such as microtiter plate walls using standard, well known techniques such as adsorption. Biotin, which contains a free carboxyl group, is coupled to the N-terminal residues of a before-described oligopeptide mixture set via that free carboxyl group, using usual coupling chemistry as described herein for coupling amino acids. Upon deprotection and cleavage of the biotinylated oligopeptide set from its solid phase support used for synthesis, if such a support is utilized, the biotinylated set is dissolved in an aqueous medium and admixed with the avidin-coated solid phase matrix to form a solid/liquid phase admixture. That admixture is maintained for a time period sufficient for the avidin and biotinylated oligopeptide set for complex, typically five minutes to about five hours, and form a biotinylated oligopeptide set-containing solid support and a liquid phase depleted of biotinylated oligopeptide. The solid and liquid phases are then separated, and the solid support is typically washed.

The thus prepared solid support that contains an affixed oligopeptide set, is then utilized with the receptor in standard solid phase assays. Where the receptor is an antibody, usual detecting systems such as the use of radiolabeled or enzyme-linked anti-antibodies such as goat anti-mouse antibodies where the receptors are mouse antibodies are utilized to detect binding. Where the receptor is a cellular receptor, radiolabels incorporated into the receptor by culture of the cells in a medium containing radioactive amino acids are typical detecting means of choice.

It is frequently convenient to provide a spacer group between the oligopeptide mixture set and the biotin. Exemplary spacers include one to about five glycine, $C_2$–$C_6$ straight chain ω-amino acids such as glycine, β-alanine, 4-aminobutyric acid (GABA) or 4-aminocaproic acid.

Thus, a N-terminal biotinylated oligopeptide set as otherwise described before is also contemplated. That biotinylated oligopeptide mixture set can further include one to about five $C_2$–$C_6$ straight chain ω-amino acid residues between the amino-terminal oligopeptide set residue and the biotin group.

For a before-discussed chromophore- or fluorescent-labeled oligopeptide mixture set, contact between the acceptor and oligopeptide mixture set can be carried out with the acceptor linked to a solid support such as sepharose or agarose. The non-binding and poorer binding mixture sets can be separated from the solid support-bound acceptor molecules by washing at increasingly higher salt concentrations until a predetermined concentration is reached that is used to define a better or best binding oligopeptide mixture. The choromophoric or fluorescent label can be used to follow the elution. Using the 2,4-dinitrophenyl chromophore as exemplary, the presence of a yellow to yellow/orange color on the solid support for a given mixture set after washing indicates an optimal binding mixture set.

An exemplary assay using a photoreactive label can be carried out with an enzyme having a known substrate. Here, the enzyme as acceptor and photoreactive labeled-oligopeptide are admixed and the admixture maintained so that binding can occur. The admixture is then irradiated using sufficient quanta of light at an appropriate wavelength, as are well known, to cause the decomposition of the photoreactive group such as an azide group and the insertion of the resulting oligopeptide radical into the enzyme polypeptide backbone. That insertion links the resulting oligopeptide to the enzyme and blocks reaction with the enzyme's substrate. Thus, an assay of enzymic activity after irradiation provides a determination of which oligopeptide mixture set bound optimally, with a diminished activity indicating enhanced binding.

Cellular receptor molecules are also particularly contemplated as useful in this assay system. The cellular receptor whose binding is contemplated for assay need not be isolated, but can be part of an intact, living cell such as bacterial, mammalian or plant cells, or viruses. When such intact, living cells are utilized, relative binding amounts can be determined by the growth or inhibition of growth of the admixed, assayed cells. The aqueous medium here is a growth medium, known to promote growth of the assayed cells.

The concentration of free acceptor molecules, including those obtained from cell preparations or those present in intact, living cells used for such binding assays is an assay-effective amount such as is normally used for such assays, and is well known in the art. It is to be understood that different concentrations of free acceptor molecules or those present in intact, living cells can vary with each acceptor studied.

A before-described assay can be carried out in vitro as is specifically illustrated hereinafter, as well as being carried out in vivo. For in vivo assays, living plants such as tobacco, alfalfa, corn (maize), zinnias and the like are contemplated hosts, whereas small laboratory mammals such as rats, mice, guinea pigs and rabbits are contemplated hosts for animal assays.

An oligopeptide mixture set-containing composition can be administered and an oligopeptide mixture contacted with the acceptors internally or externally in plants through watering, misting of foliage, or injection. For the animals, a composition can be administered internally, orally or by injection such as intraperitoneally, subcutaneously or intramuscularly or topically as by application to skin for the contact between donor and acceptor to take place.

Binding here can be assessed by relative growth rate (positive or negative) or by the affect of the composition on one or more tissues, as through microscopic examination, by body temperature where pathogen-infected animals are used, and the like as are well known.

Use of the scanning SPCL process with 5× N-acetyl C-amide oligopeptide mixture 6-mer sets exactly predicted the six-residue antigen (SEQ ID NO:3) bound by monoclonal antibody mAb 17D09 (Example 3). A similar study in Example 4 determined the N-terminal five of six residues of the peptide antigen bound by mAb 125-OF3. The sixth, C-terminal, residue was found to be redundant in this study, as it had been so found in an earlier study [Appel et al., *J. Immunol.*, 144:976–983 (1990)]. Thus, the power of the scanning SPCL process was proven by comparisons with known ligand sequences.

Several useful new oligopeptides have been prepared using a scanning SPCL process of the invention as discussed hereinbefore.

One group of exemplary C-amide oligopeptides competitively inhibits the binding of the synthetic met-enkephalin analog, DAGO, to the mu enkephalin receptor. Using the scanning SPCL process with C-amide 5× oligopeptide mixture sets, this group has the sequence:

TyrGlyX$_3$aaPheX$_5$aaX$_6$aa-NH$_2$   [SEQ ID NO:7]

wherein X$_3$aa is Phe or Gly;

X$_5$aa is Phe, Tyr, Met, Leu or Arg; and

X$_6$aa is Arg, Phe, Tyr, Thr or Lys (Arg, Phe and Tyr being preferred).

A series of 24 6-mer oligopeptides was prepared having each position defined keeping in mind the results of the above scanning assay. Those oligopeptides exhibited IC$_{50}$ values on the order of about 15 nM to about 50 μM. Of those 24 oligopeptides, those shown below exhibited IC$_{50}$ values of about 15 to about 50 nM, and are particularly preferred.

TyrGlyGlyPheMetTyr-NH$_2$   [SEQ ID NO:8];

TyrGlyGlyPheMetArg-NH$_2$   [SEQ ID NO:9];

TyrGlyGlyPheTyrTyr-NH$_2$   [SEQ ID NO:10];

and

TyrGlyGlyPheLeuTyr-NH$_2$   [SEQ ID NO:11].

Thus, the scanning assay process cut the 64 million possible oligopeptides down to about 50, from which were prepared 24 6-mers that were good inhibitors, of which four were excellent inhibitors.

A group of N-acetyl C-amide oligopeptides that also inhibit the mu enkephalin receptor was determined using 5× oligopeptide sets and the scanning SPCL process described herein. A resulting oligopeptide obtained by that method has the sequence:

Ac-ArgPheX$_3$aaX$_4$aaPheX$_6$aa-NH$_2$   [SEQ ID NO:32]

wherein X$_3$aa is Met, Leu, Phe or Tyr (with Met being preferred);

X$_4$aa is Phe, Tyr, Arg, Ala, Leu, Asn, Gly or Lys (with Phe or Tyr being preferred); and X$_6$aa is Phe, Arg, Tyr or Leu (with Phe being preferred).

Thus, the 64,000,000 possible 6-mers were cut down to about 128 and similar sequences. Where the preferred Met group is used, the number becomes 32 6-mers. Where the preferred Met (X$_3$aa), Phe or Tyr (X$_4$aa) and Phe (X$_6$aa) residues are present, two 6-mers result.

Thus, a preferred oligopeptide of this group has the sequence

Ac-ArgPheMetX$_4$aaPhePhe-NH$_2$   [SEQ ID NO:33], wherein X$_4$aa is as above.

Using 6-mer oligopeptide sets having progressively defined positions from N- to C-terminal as described in WO 92/09300 in conjunction with the 5× oligopeptide sets discussed herein, further mu receptor inhibitors were obtained. These N-acetyl C-amide materials having mixtures of the twenty amino acid residues at the C-terminus exhibited IC$_{50}$ values between about 30 and 100 nM, and had sequences quite similar to those identified by the scanning SPCL processes. Those sequences were:

Ac-ArgPheMetTrpMetX$_6$aa-NH$_2$   [SEQ ID NO:34];

Ac-ArgPheMetTrpValX$_6$aa-NH$_2$   [SEQ ID NO:35];

and

Ac-ArgPheMetTrpGlnX$_6$aa-NH$_2$   [SEQ ID NO:36];

wherein X$_6$aa is any of the 20 naturally occurring amino acid residues except Cys and Trp.

Written as a single sequence, those latter oligopeptides can be expressed as

Ac-ArgPheMetTrpX$_5$aaX$_6$aa-NH$_2$   [SEQ ID NO:37], wherein X$_5$aa is Met, Val or Gln; and X$_6$aa is as described above.

Oligopeptides having a Met residue in the X$_5$aa position [SEQ ID NO:34] were particularly active. All twenty 6-mer N-acetyl C-amide peptides were prepared and each exhibited an IC$_{50}$ value of between about 5 and 100 nM, with fifteen such 6-mers having IC$_{50}$ values of less than about 50 nM. Thus, an oligopeptide of SEQ ID NO:34 is a particularly preferred 6-mer N-acetyl C-amide oligopeptide that inhibits DAGO binding to the mu opioid receptor. In most preferred practice, X$_6$aa of SEQ ID NO:34 is Thr, Arg, Gly, Lys, Ser, Leu, Asn, Ala or Met (SEQ ID NOS:38–46).

It is thus seen that use of oligopeptide sets having five mixture positions (5× sets) and one defined position cut down the potential 6-mer candidates from 64 million to just over one hundred, and that with that narrowing, new peptides whose sequences are quite unlike that of the natural ligand or its synthetic analog could be prepared having extremely high potencies. The sequences of the natural and synthetic ligands are shown in Example 5, hereinafter.

Another group of N-acetyl C-amide oligopeptides inhibits the hemolytic activity of the 26-residue polypeptide of honeybee venom, melittin [SEQ ID NO:58]. This peptide is illustrated in Example 6, hereinafter.

Using the scanning SPCL process described herein with one defined position and five undefined positions (5× sets) in N-acetyl C-amide 6-mers, the following was found in descending order of inhibitory preference and within a factor of about two of the best inhibitor: Val, Ile, Gln, Tyr, Met, Leu, Glu, Asn, Phe, Asp and Pro when in the first position, with Ser, Arg and Lys exhibiting the worst inhibition. Ile, Met, His, Gln, Ser, Ala, Gly, Thr and Val were the best for the second position, with Lys, Arg and Pro among the worst. Sixteen of the 18 residues exhibited inhibitions within a factor of two when at the third position, with Val and Gln being best, followed by Leu, and Ser and Arg being the two residues outside the cutoff. A similar finding (17 out of 18) was made at position four, with Ile, Gln, Val and Leu being best, with Arg again outside the cutoff and Lys and Pro being among the worst. Ile, Phe and Val were best at position five, followed by Pro and Tyr, with Ser, Arg and Lys exhibiting the worst inhibitions. Ile and Val were again best inhibitors at position six, with 15 of the 18 residues exhibiting inhibitions within a factor of two of that of Ile, and Pro, Lys and Arg being below the cutoff.

The above results indicated a strong preference for a ligand containing Ile and Val, two relatively small hydrophobic residues. An almost as strong preference for Gln and Leu in the ligand was also shown. A strong preference against residues such as Ser, Pro, Lys and Arg for the ligand was also provided by these results. Thus, again, the 64 million possible 6-mer ligands could again be cut back to a smaller number by using a screening process described herein.

The above results were used to prepare several oligopeptides useful for inhibiting melittin-induced hemolysis that have the sequences shown below:

| Ac-TrpIleGlnIlePheIle-NH$_2$ | [SEQ ID NO:60]; |
| Ac-ValIleGlnGlnPheVal-NH$_2$ | [SEQ ID NO:61]; |
| Ac-ValIleValIleIleIle-NH$_2$ | [SEQ ID NO:62]; | and

| Ac-ValIleLeuValPheVal-NH$_2$ | [SEQ ID NO:63]. |

The above four oligopeptides and similar materials can be represented by the single sequence Ac-X$_1$aaIleX$_3$aaX$_4$aaX$_5$aaX$_6$aa-NH$_2$   [SEQ ID NO:113]

wherein

X$_1$aa is Trp or Val;

X$_3$aa is Gln, Val or Leu;

X$_4$aa is Ile, Gln or Val;

X$_5$aa is Ile or Val; and

X$_6$aa is Ile or Val.

Combining the results obtained above with the progressive identification of further positions as was discussed for the mu opioid receptors, further, narrowed oligopeptide sequences were identified that could inhibit hemolysis caused by melittin. A preferred oligopeptide has the sequence Ac-IleValIleX$_4$aaX$_5$aaX$_6$aa-NH$_2$   [SEQ ID NO:59]

wherein X$_4$aa is Phe or Cys;

X$_5$aa is Phe, Ala, Gly or Asp when X$_4$aa is Phe, and Leu, Phe, Met, Gln, Val, Pro, Asn or Asp when X$_4$aa is Cys; and X$_6$aa is Glu, Trp, Thr, Phe, Gly, Asp, Tyr, Cys, Val, Leu or Ala when X$_4$aa is Phe, and Gln, Asp, Asn, Met, Tyr, Thr, Ser, Glu, Trp, Val, Pro or Cys when X$_4$aa is Cys.

Among the above peptides, two preferences of two residues each were noted. Where X$_4$aa is Cys, X$_5$aa is preferably Gln or Val, and where X$_4$aa is Phe, X$_5$aa is preferably Ala or Asp. Particularly preferred sequences having four defined positions are Ac-IleValIleCysX$_5$aaX$_6$aa-NH$_2$   [SEQ ID NO:111]

wherein X$_5$aa is Gln or Val; and

X$_6$aa is Gln, Asp, Asn, Met, Tyr, Thr or Ser when X$_5$aa is Gln, and Glu, Asp, Met, Thr, Trp, Tyr, Val, Pro, Ser, Cys or Asn when X$_5$aa is Val; and Ac-IleValIlePheX$_5$aaX$_6$aa-NH$_2$   [SEQ ID NO:112]

wherein X$_5$aa is Ala or Asp; and

X$_6$aa is Glu, Trp, Thr, Phe, Gly, Asp or Tyr when X$_5$aa is Ala, and Cys, Trp, Phe, Val, Leu or Ala when X$_5$aa is Asp.

The individual N-acetyl C-amide 6-mer peptides represented by the above two sequences have SEQ ID NOS:80–110, and are particularly preferred, as are the peptides of SEQ ID NOS:60–63.

A variation of the scanning SPCL process was used to identify an oligopeptide that would inhibit the enzyme trypsin. It is well known that trypsin hydrolyzes proteins at the C-terminal side of a Lys or Arg residue.

Thus, two sets of five N-acetyl C-amide 6-mer mixture sets were prepared that contained either a Lys or an Arg residue at each predetermined position in the oligopeptide chain and also one of the naturally occurring amino acid residues bonded at its C-terminus. Fmoc chemistry was used here with a cotton solid support, so nineteen different residues occupied each mixture position. In addition, because of the synthetic method used (Example 7, manual), the prepared 6-mer sets all included a Gly residue at the C-terminal position. That C-terminal position is not considered to be part of the 6-mer.

The predetermined Lys-O or Arg-O dipeptide sequences were placed at each possible position within the 6-mer sets to determine which position and which predetermined O residue provided optimal inhibition and therefore binding. It was found that the sequence Lys-O=LysIle at positions 2 and 3 of the sequence provided optimal inhibition.

The remaining four positions of the 6-mer sequence were then determined as discussed in WO 92/09300 and Houghten et al., *Nature*, 354:84 (1991). The 6-mer optimally inhibiting (binding) sequence so determined was prepared using the machine method of Example 7, and is Ac-AlaLysIleTyrArgPro-NH$_2$   [SEQ ID NO:114], which exhibited an IC$_{50}$ value of 46 μM.

Although 46 μM is an acceptable inhibitory concentration for a small molecule, it was desired to extend the 6-mer to determine if still better binding could be obtained. The well known and defined 58-mer pancreatic trypsin inhibitor exhibits an $IC_{50}$ value of 82 nM under similar conditions.

Thus, using the above 6-mer as a core, that sequence was extended in each direction using the manual synthesis method by first adding three mixture positions at the N-terminus (positions 1-3), each of nineteen residues at the C-terminus of the core (position 10) and then two C-terminal mixture positions. Once the tenth optimal residue (at the C-terminus of the core 6-mer) was determined, a new set was prepared in which the third residue was each of the nineteen residues, with positions 1–2 and 11–12 being occupied by mixtures of the nineteen. The remaining positions were similarly determined until an optimal binding 12-mer sequence was obtained.

That optimal 12-mer was prepared using the machine synthesis and had the sequence Ac-TyrTyrGlyAlaLysIleTyrArgproAspLysMet-NH$_2$ [SEQ ID NO:119].

The oligopeptide of SEQ ID NO:45 exhibited an $IC_{50}$ value of 10 μM, a 5-fold enhancement over the value obtained for the 6-mer core.

Aside from the centrally located lysine residue, the above peptides have little homology to pancreatic trypsin inhibitor. Some other known trypsin inhibitors have a LysIle sequence, but the above peptide is also believed to have different sequences from those inhibitors.

The following examples are intended to illustrate, but not limit, the invention.

EXAMPLE 1

Exemplary Synthesis of a Set of Mixed Oligopeptides having Equimolar Amounts of the Twenty Natural Amino Acid Residues Aliquots of five grams (4.65 mmols) of p-methylbenzhydrylamine hydrochloride resin (MBHA) are placed into twenty porous polypropylene bags. These bags are placed into a common container and washed with 1.0 liter of $CH_2Cl_2$ three times (three minutes each time), then again washed three times (three minutes each time) with 1.0 liter of 5 percent DIEA/$CH_2Cl_2$ (DIEA=diisopropylethylamine). The bags are then rinsed with $CH_2Cl_2$ and placed into separate reaction vessels each containing 50 ml (0.56M) of the respective t-Boc-amino acid/$CH_2Cl_2$. N,N-Diisopropylcarbodiimide (DIPCDI; 25 ml; 1.12M) is added to each container, as a coupling agent.

Twenty amino acid derivatives are separately coupled to the resin in 50/50 (v/v) DMF/$CH_2Cl_2$. After one hour of vigorous shaking, Gisen's picric acid test [Gisen, *Anal. Chem. Acta*, 58:248–249 (1972)] is performed to determine the completeness of the coupling reaction. On confirming completeness of reaction, all of the resin packets are then washed with 1.5 liters of DMF and washed two more times with 1.5 liters of $CH_2Cl_2$.

After rinsing, the resins are removed from their separate packets and admixed together to form a pool in a common bag. The resulting resin mixture is then dried and weighed, divided again into 20 equal portions (aliquots), and placed into 20 further polypropylene bags (enclosed). In a common reaction vessel the following steps are carried out:

(1) deprotection is carried out on the enclosed aliquots for thirty minutes with 1.5 liters of 55 percent TFA/$CH_2Cl_2$; and 2) neutralization is carried out with three washes of 1.5 liters each of 5 percent DIEA/$CH_2Cl_2$.

Each bag is placed in a separate solution of activated t-Boc-amino acid derivative and the coupling reaction carried out to completion as before. All coupling reactions are monitored using the above quantitative picric acid assay. Next, the bags are opened and the resulting t-Boc-protected dipeptide resins are mixed together to form a pool, aliquots are made from the pool, the aliquots are enclosed, deprotected and further reactions are carried out.

This process can be repeated any number of times yielding at each step an equimolar representation of the desired number of amino acid residues in the peptide chain. The principal process steps are conveniently referred to as a divide-couple-recombine (DCR) synthesis.

After at least five such couplings and mixtures are carried out, the polypropylene bags are kept separated to here provide the twenty sets having the amino-terminal residue as the single, predetermined residue, with positions 2–4 being occupied by equimolar amounts of the twenty residues. To prepare sets having the single, predetermined amino acid residue at other than the amino-terminus, the contents of the bags are not mixed after adding a residue at the desired, predetermined position. Rather, the contents of each of the twenty bags are separated into 20 aliquots, deprotected and then separately reacted with the twenty amino acid derivatives. The contents of each set of twenty bags thus produced are thereafter mixed and treated as before-described until the desired oligopeptide length is achieved.

The side chain protecting groups used with α-aminoterminal t-Boc and Fmoc protecting groups are usually different. The side chain protecting groups utilized for one type of synthesis or the other are as shown in the table below. Other usually used side chain protecting groups are also utilized for both types of syntheses.

| Amino Acid Derivative | Side Chain Protecting Group | |
|---|---|---|
| | N-t-Boc Protected | N-Fmoc Protected |
| Arginine | Toluenesulfonyl* | Mtr** |
| Cysteine | p-Methoxybenzyl | t-Butyl ether |
| Glutamic acid | O-Benzyl | t-Butyl ester |
| Histidine | N-im-dinitrophenyl* | Trityl |
| Lysine | N-(o-chlorobenzyl-oxycarbonyl) | t-Boc |
| Serine | O-Benzyl | t-Butyl ether |
| Threonine | O-Benzyl | t-Butyl ether |
| Tyrosine | O-(m-bromobenzenyl-oxycarbonyl) | t-Butyl ether |
| Aspartic acid | O-Benzyl | t-Butyl ester |

*Arginine and histidine are coupled in the presence of N-hydroxylbenztriazole [Hruby et al., Angew. Chem. Int. Ed. Engl., 10:336–339 (1971)].
**Mtr = 4-Methoxy-2,3,6-trimethylbenzenesulfonyl.

For oligopeptide mixture sets not having an N-terminal $C_1$–$C_8$ acyl (e.g. acetyl) group, the following procedure was used for side chain deprotection of N-t-Boc-protected oligopeptide chains. The fully protected solid support-coupled oligopeptide mixtures are treated with 55 percent trifluoroacetic acid in methylene chloride prior to the HF treatment to remove the final t-Boc-protecting group. Then the protected solid support-coupled oligopeptide mixtures, in polypropylene mesh packets [Houghten, *Proc. Natl. Acad. Sci., USA*, 82:5131–5135 (1985)] are rinsed with alternating washes of $CH_2Cl_2$ and isopropanol, and dried under reduced pressure for twenty-four hours.

The low HF step [Tam et al., *J. Am. Chem. Soc.*, 195:6442–6455 (1983)] is carried out in a two liter polypropylene reaction vessel, using a solution of 60 percent dimethylsulfide, 25 percent HF, ten percent p-cresol and five percent ethylenedithiol. HF is condensed at −78° C. After condensation, the HF-scavenger solution is carefully transferred to the reaction vessel that contained the resin-containing packets. The low HF solution is made to give 5 mls per 0.1 mmol of oligopeptide. After the reagents are added, the reaction vessel is placed in an ice water bath and shaken for two hours. The low HF solution is removed and the packets containing the deprotected peptide resins are quickly washed with chilled $CH_2Cl_2$. The $CH_2Cl_2$ wash is repeated nine times (one minute each) followed by ten alternating washes of isopropanol and $CH_2Cl_2$. Finally, the resin is washed five times with DMF, then twice more with $CH_2Cl_2$. Deprotected peptide resin packets are dried under reduced pressure. After this process is completed, the unprotected peptides are ready to be cleaved by anhydrous HF.

The N-terminal Fmoc protecting groups of enclosed, protected solid support-coupled oligopeptide mixtures are removed by treatment with twenty percent piperidine in DMF for ten minutes. Then the resulting N-deprotected, side chain-protected peptide resins in polypropylene packets are washed with DMF twice (five minutes each) followed by two rinses with $CH_2Cl_2$ (one minute each) and dried in a vacuum for twenty-four hours. Although porous containers are not utilized, each solid support-coupled reaction product must still be maintained separately during reactions.

The side chain deprotection is carried out in a two liter polypropylene reaction vessel, using a solution of 85 percent TFA, 5 percent phenol, 4 percent thioanisole, 4 percent deionized $H_2O$ and 2 percent ethanedithiol. The resins are shaken for 3.5 hours at room temperature. The reaction solution is removed, and the packets containing the completely deprotected solid support-coupled oligopeptide mixtures are quickly washed with chilled ether. The ether wash is repeated nine times (one minute each) followed by ten alternating washes of isopropanol and $CH_2Cl_2$. Finally, the solid support-coupled oligopeptide mixtures are washed five times with DMF, then twice more with $CH_2Cl_2$. Deprotected solid support-coupled oligopeptide mixtures and their enclosing packets are dried under reduced pressure. After this process is completed, the unprotected peptides are ready to be cleaved by anhydrous HF.

Where an N-acyl group such as an acetyl group is to be present on an oligopeptide mixture set, the final t-Boc or Fmoc protecting group is removed as above, an excess of acetic anhydride is added and the reaction is maintained until there are no more free amino groups present as discussed elsewhere herein. The above rinsing and drying steps are then carried out, followed by deprotection and cleavage of the oligopeptide mixture set from the solid support.

As noted earlier, use of a benzhydrylamine resin as a solid support and anhydrous HF/anisole for cleavage of the oligopeptide mixture set provides a C-terminal amido group for the oligopeptide mixture set produced. Use of a benzhydrylalcohol resin solid support and that cleavage procedure provides a C-terminal carboxylic acid. Use of a before-discussed disulfide-containing linking group between the solid support and oligopeptide chains and cleavage with a disulfide bond breaking agent as discussed provides a C-terminal mercaptan linking group amide-bonded to the oligopeptide chains.

EXAMPLE 2

Chemical Mixture Synthesis

These syntheses using 18 of the 20 naturally occurring amino acid derivatives (Cys and Trp omitted) were carried out substantially as described in U.S. Pat. No. 4,631,211 and Example 1.

A cross-linked polystyrene resin was used as solid support that also included 0.93 milliequivalents (meq) of benzhydrylamine groups per gram. The solid support resin was typically utilized in an amount of 300 milligrams (mg) so that 2.79 meq of resin-amine were initially provided in each reaction.

The mixture of amino acid derivatives noted in Table 1 at 0.5M in 4 ml of dimethylformamide (DMF) was used for each coupling, as about a 7-fold molar excess over the amount of amine present, as resin-amine or after deprotection to provide N-terminal amine (free amine) groups. One equivalent of DIPCDI as coupling agent and one equivalent of N-hydroxylbenztriazole-$H_2O$ were used per equivalent of mixed amino acid derivative, so both were also present in about a 7-fold excess over the free amine groups present.

Each coupling was carried out at room temperature until there was no remaining free amine groups as in Example 1; about one hour. Deprotection and neutralizations were also carried out as in Example 1.

Each position containing equimolar amounts of amino acid residues was added as described above. Using a 6-mer SPCL whose fifth position is occupied by one of eighteen predetermined amino acid residues as exemplary, the above coupling provides a support-coupled product of the formula X-B.

That support-coupled product was then divided into at least 18 aliquots of equal weight, small portions of the preparation often being retained for analytical purposes. Those aliquots were enclosed in labeled porous packets, as discussed in Example 1, and the 18 individual amino acid derivatives were reacted separately with those aliquots after deprotection and neutralization to form 18 support-coupled products of the formula $O_5$X-B.

Those 18 labeled porous packets containing the $O_5$X-B support-coupled product were then deprotected and neutralized together, and those products were together reacted again as discussed before with the mixed amino acid derivatives, while being maintained in their packets, to form 18 sets of support-coupled products of the formula $XO_5$X-B. This procedure was repeated three more times to form the 18 support-coupled 6-mer sets whose fifth position from the N-terminus was occupied by each of the 18 different predetermined amino acid residues and whose other positions were occupied by equimolar amounts of the 18 amino acid residues present in the reaction mixtures.

Where N-terminal acetyl groups were to be used, as in Examples 3–5 hereafter, the N-terminal t-Boc groups were removed, the resulting free amines neutralized and the support-coupled 6-mers were reacted with acetic anhydride to form N-acetyl (Ac) groups. The N-acetyl coupled peptides were then deprotected and cleaved from the solid support to form a plurality (18) of N-acetyl C-terminal amide 6-mer oligopeptide sets.

The above procedures were similarly used, as appropriate, to prepare the remaining five pluralities of 18 sets (another 90 sets) having one of eighteen predetermined amino acid residues at predetermined positions 1–4 and 6, and mixtures of equal molar amounts of the 18 amino acid residues at the other oligopeptide chain positions.

The relative equimolarity of coupling using the above procedure as compared to the physical mixture methods was determined by amino acid analysis of support-coupled products from a single coupling reaction. A commercial amino acid analyzer was utilized for these assays. The specific manipulations utilized are discussed hereinafter.

As is well known, even commercially available amino acid analyzers do not provide precise determinations because of several factors including decomposition of the amino acids, and the various reactions and responses the machines must carry out and make. On the other hand, the physical mixture method provides equimolar mixtures to a precision that is much greater than that obtained by the machine alone.

Thus, a physical mixture process solid support-coupled product (X-B) of one coupling reaction was prepared as in Example 1, deprotected, cleaved from the solid support resin and collected. A similar X-B solid support-coupled product was prepared by the chemical mixture method of this example. That X-B product was similarly deprotected, cleaved from the solid support resin and collected. Those samples were then sent amino acid analysis.

More specifically, after each of the above t-Boc, side chain-protected mixtures was prepared, the t-Boc groups were removed, and the side chains deprotected. Each of the two mixed amino acid-coupled solid supports (X-B) was dried, and 20 mg of each resin-linked product was placed into 5 ml glass ampules. One milliliter of propionic acid:HCl (50:50, V/V) was added to each ampule. Air was removed from the ampules with a vacuum pump with care being taken not to aspirate the contents of the ampules. Each ampule was then sealed using a propane flame, while under vacuum. The sealed ampules were placed in a dry block heater and maintained at 130° C. for two hours to cleave the reacted amino acids from the solid support resin and form hydrolyzate solutions.

Thereafter, upon cooling to room temperature, the ampules were broken open and their contents filtered into separate 12–75 mm culture tubes. Aliquots (20 μl) of the hydrolyzate solution were placed into 5–50 mm culture tubes in duplicate. Those samples were coded, dried and sealed.

The sealed, coded samples were sent to Core Laboratories, New Orleans, La. for amino acid analysis. The results of that analysis are shown below, for each sample. In addition, because it is known that the physical mixture method provides more precise results than does amino acid analysis, the percentage of deviation from equimolarity for the chemical mixture method was determined by presuming that the value obtained for the individual amino acid residues obtained from the physical mixture method was the correct value of one-eighteenth mole percent (5.56 percent). It is noted that Glu and Gln analyze together as do Asp and Asn because the resin-cleaving step also destroys the Gln and Asn amide bonds, forming Glu and Asp, respectively.

| | Mole Percent | | Deviation from |
|---|---|---|---|
| Amino Acid | Physical Mixture | Chemical Mixture | Equimolarity (Percent) |
| Asp,Asn | 13.84 | 16.73 | +21 |
| Glu,Gln | 10.87 | 11.99 | +10 |
| Ser | 4.11 | 4.14 | −1 |
| Gly | 5.13 | 5.04 | −2 |
| His | 4.84 | 3.16 | −35 |
| Arg | 6.57 | 5.03 | −23 |
| Thr | 5.48 | 6.10 | +11 |
| Ala | 6.36 | 6.48 | +2 |
| Pro | 7.22 | 7.28 | +1 |
| Tyr | 4.31 | 3.53 | −18 |
| Val | 6.08 | 6.76 | +11 |
| Met | 3.38 | 4.13 | +22 |
| Ile | 5.08 | 4.07 | −20 |

-continued

| | Mole Percent | | Deviation from |
|---|---|---|---|
| Amino Acid | Physical Mixture | Chemical Mixture | Equimolarity (Percent) |
| Leu | 6.58 | 5.95 | −10 |
| Phe | 5.17 | 3.78 | −27 |
| Lys | 4.96 | 5.85 | +18 |

EXAMPLE 3

Binding Inhibition of Monoclonal Antibody mAb 17DO9

Monoclonal antibody mAb 17D09 binds to the antigenic oligopeptide

Ac-TyrProTyrAspValProAspTyrAlaSerLeu ArgSer-NH$_2$ (SEQ ID NO:1)

(Wilson et al., *Cell,* 37:767–778 (1984). A SPCL was prepared and scanned using the 18 amino acid derivatives discussed in Example 2 as N-acetyl C-amide derivatives. The results of this study are shown graphically in FIG. 2.

Of the 18 amino acids defined in the first position SPCL, aspartic acid ($IC_{50}$=0.8 mM) was found to most effectively inhibit antibody binding. At the highest concentration tested (6 mM), no other amino acid residue in this position was found to inhibit binding more than 30 percent. The second position SPCL, when defined with valine ($IC_{50}$=5 mM) or isoleucine ($IC_{50}$=6 mM), yielded the most effective inhibiting peptide mixtures. The third position SPCL, defined with proline ($IC_{50}$=1.0 mM), was found to be the most effective inhibitor, followed by glutamic acid ($IC_{50}$=2.6 mM). Strikingly, the fourth and fifth position SPCLs defined with aspartic acid ($IC_{50}$=0.7 mM) and tyrosine ($IC_{50}$=0.3), respectively, were the only inhibiting peptide mixtures for these positional SPCLs. The sixth position SPCL, when defined with alanine ($IC_{50}$=0.4 mM), more effectively inhibited antibody binding than serine ($IC_{50}$=1.4 mM).

The individual amino acid residue yielding the most effective inhibiting peptide mixture for each of the six positions (AspValProAspTyrAla; SEQ ID NO:3) corresponded exactly to the known antigenic determinant for this peptide-antibody interaction. This antigenic determinant was identified in earlier studies using omission and substitution analogs of SEQ ID NO:1 [Pinilla et al., in *Peptides. Proceedings of the Twelfth American Peptide Symposium* (eds Smith, J. A. & Rivier, J. E.) 867–868 (Escom, Leiden, 1992)], and was also found using a previously described SPCL along with a four step iterative selection and synthesis process [Houghten et al., *Nature* 354:84–86 (1991)]. It should be noted that aspartic acid at position one, aspartic acid at position four, and tyrosine at position five were the only amino acids found to show significant inhibition at these positions, thus illustrating the specificity of these residues in the peptide-antibody interaction.

In contrast, a number of peptide mixtures for each of the second, third, and sixth defined positions were found to inhibit antibody binding at a level of 30 percent or greater, which illustrates the relative redundancy of these positions. The pattern of relative positional importance within the antigenic determinant found here using the scanning SPCL corresponds to that found in earlier mapping studies [Pinilla et al., in *Peptides. Proceedings of the Twelfth American Peptide Symposium* (eds Smith, J. A. & Rivier, J. E.) 867–868 (Escom, Leiden, 1992)]. These results are also consistent with the recent structure determination of the interaction of this monoclonal antibody with the N-Ac C-amide peptide of SEQ ID NO:1 at residue positions 3–11 using x-ray crystallographic methods [Rini et al., *Science* 255:959–965 (1992)].

The assay here was a competitive ELISA as described in Houghten et al., *Nature*, 354:84–86 (1991). Briefly, the oligopeptide of SEQ ID NO:1 was adsorbed to microtiter plates at 100 pm/well. After blocking non-specific binding positions, 25 μl of each oligopeptide mixture set (6 mM) was added to each well, followed by the addition of 25 μl of mAb 17DO9 at predetermined dilutions. Percent inhibition of antibody binding by each oligopeptide mixture set was determined relative to the 100 percent binding of the mAb to the antigenic peptide on the plate. The concentration of oligopeptide mixture set necessary to inhibit 50 percent antibody binding ($IC_{50}$) was determined by serially diluting the mixture sets prior to addition of the mAb.

EXAMPLE 4

Binding Inhibition of Monoclonal Antibody mAb 125-10F3

The procedure of Example 3 was followed for monoclonal antibody mAb 125-10F3 that binds to antigenic peptide of the formula

Ac-GlyAlaSerProTyrProAsnLeuSerAsn GlnGlnThr (SEQ ID NO:2)

as discussed in Appel et al., *J. Immunol.*, 144:976–983 (1990). The results of this study are shown graphically in FIG. 3.

The first position SPCL defined with proline ($IC_{50}$=1.5 mM) was found to be the most effective inhibiting peptide mixture, whereas tyrosine inhibited only 25 percent antibody binding. The second position SPCL defined with tyrosine ($IC_{50}$=2.3 mM) was the only peptide mixture found to inhibit antibody binding. Likewise, the third position SPCL defined with proline ($IC_{50}$=0.3 mM) was the only peptide mixture found to inhibit binding. The fourth position SPCL defined with asparagine ($IC_{50}$=0.3 mM) was more effective than proline ($IC_{50}$=>6 mM). The fifth position SPCL defined with leucine ($IC_{50}$=1.8 mM) was the most effective inhibitor, whereas both isoleucine ($IC_{50}$=>6 mM) and asparagine ($IC_{50}$=>6 mM) were found to have lower activity. None of the peptide mixtures of the sixth position SPCL inhibited antibody binding by more than 50 percent at the highest peptide mixture concentration tested (6 mM). However, leucine and arginine were found to be the most effective as defined residues.

The individual amino acid residue of the most effective inhibiting peptide mixture at each of the six positions yielded the sequence ProTyrProAsnLeuLeu (SEQ ID NO:4). The first five positions correspond to the sequence of the known antigenic determinant. This antigenic determinant recognized by mAb 125-10F3 was identified in earlier studies using omission and substitution analogs of SEQ ID NO:2 [Appel et al., *J. Immunol.,* 144:976–983 (1990)], as well as upon using another SPCL in conjunction with an iterative selection and synthesis process [Houghten et al., *Biotechniques* (1992) (in press)]. These studies also found that the sixth position, serine, was relatively redundant.

These assays were conducted as in Example 3 using mAB 125-10F3 in place of mAb 17DO9 and antigenic peptide SEQ ID NO:2 in place of antigenic peptide SEQ ID NO:1.

EXAMPLE 5

Binding to Opioid Receptors The enkephalins; i.e.,

TyrGlyGlyPheNH($CH_3SCH_2CH_2$)$CHCO_2H$ (YGGFM-OH; SEQ ID NO:5) and TyrGlyGlyPheNH[$(CH_3)_2CHCH_2$] $CHCO_2H$ (YGGFL-OH; SEQ ID NO:6) were the first natural ligands found for the opioid receptors. These bind to three known receptor subclasses (mu, delta and kappa) with differing affinities [reviewed in Schiller, *Progress in Medicinal Chemistry,* Ellis et al. eds., Elsevier Science Publishers, U.K. (1990) pages 301–340]. The studies herein utilized an analog of met-enkephalin, [$^3$H]-[D-Ala$^2$,MePhe$^4$,Gly-Ol$^5$] enkephalin (DAGO) that is known to bind specifically to the mu receptor in competitive binding studies with the SPCL mixture sets.

A. Non-Acylated Sets

Hexapeptide (6-mer) oligopeptide mixture sets were prepared as discussed in Example 2 having amino- and carboxamido-termini, as discussed in Example 1 and elsewhere herein. Each of the six sets of 18 positional sets was assayed for competitive binding against DAGO for the mu receptor.

Position 1 was defined only by Tyr ($IC_{50}$=40 μM). Position 2 was defined only by Gly ($IC_{50}$=49 μM). Position 3 was found to have two residues with optimal $IC_{50}$ values within a factor of two of each other, then Phe and Gly ($IC_{50}$=28 and 46 μM, respectively). Position 4 was defined by a single residue, Phe, ($IC_{50}$=45 μM). Position 5 had a total of five residues within a factor of two of optimum, Phe, Tyr, Met, Leu and Arg ($IC_{50}$=96, 107, 156, 162 and 169 μM, respectively). Position 6 also had a total of five residues within a factor of two of optimum, Arg, Phe, Tyr, Thr and Lys ($IC_{50}$=69, 77, 92, 134 and 139 μM, respectively).

A second triplicate study was carried out with substantially identical results at positions 1–5, slight variations being noted in the inhibitory concentrations.

Some residue preferences and inhibitory concentrations were, however noted as different at position 6. Thus, only three residues Phe, Arg and Tyr provided inhibitory concentrations within a factor of two of each other (69±8, 105±26, and 111±24 μM, respectively). Those three residues were, nonetheless, the same three best residues noted in the first assay, and are preferred at position 6.

By so determining the identities and positions of the amino acid residues that exhibited enhanced binding for each set of the plurality of sets, the amino acid residue sequence for a 6-mer oligopeptide that exhibits enhanced binding to the mu receptor is TyrGlyX$_3$aaPheX$_5$aaX$_6$aa-NH$_2$ [SEQ ID NO:7]

wherein X$_3$aa is Phe or Gly;

X$_5$aa is Phe, Tyr, Met, Leu or Arg; and

X$_6$aa is Arg, Phe, Tyr, Thr or Lys.

The above binding studies thus defined three of the five residues and positions of the donor (ligand) molecule with a single residue identical to that present in the same position in the native donor. A fourth position was defined by two residues in these studies, one of which is also present at that position in the native donor molecule. The fifth position of the ligand can be one of two residues in the native 5-mer ligand, and those two residues were among the five determined by the assays.

A series of 6-mer non-acylated oligopeptides was then prepared according to the above sequence, but omitting X$_5$aa=Arg and X$_6$aa=Thr or Lys as those residues produced enhanced, but poorer binding than the other residues. The synthesized oligopeptides were thereafter assayed in the same assay with the results being shown in the table below.

| SEQ ID NO: | Oligopeptide Sequence | $IC_{50} \pm$ s.d. (nM) | Repeats |
|---|---|---|---|
| 8 | YGGFMY—$NH_2$ | 17 ± 3 | 3 |
| 9 | YGGFMR—$NH_2$ | 24 ± 3 | 3 |
| 10 | YGGFYY—$NH_2$ | 40 ± 13 | 4 |
| 11 | YGGFLY—$NH_2$ | 49 ± 17 | 3 |
| 12 | YGGFLR—$NH_2$ | 111 ± 33 | 4 |
| 13 | YGGFFY—$NH_2$ | 137 ± 29 | 4 |
| 14 | YGGFMF—$NH_2$ | 170 ± 62 | 4 |
| 15 | YGFFMY—$NH_2$ | 181 ± 93 | 4 |
| 16 | YGGFFR—$NH_2$ | 196 ± 61 | 3 |
| 17 | YGGFLF—$NH_2$ | 251 ± 92 | 4 |
| 18 | YGGFYR—$NH_2$ | 373 ± 118 | 3 |
| 19 | YGFFYY—$NH_2$ | 477 ± 88 | 3 |
| 20 | YGFFLY—$NH_2$ | 514 ± 180 | 4 |
| 21 | YGFFMR—$NH_2$ | 645 ± 280 | 4 |
| 22 | YGFFLR—$NH_2$ | 745 ± 128 | 4 |
| 23 | YGFFYR—$NH_2$ | 885 ± 217 | 3 |
| 24 | YGGFFF—$NH_2$ | 1290 ± 492 | 4 |
| 25 | YGFFMF—$NH_2$ | 1510 ± 436 | 4 |
| 26 | YGFFFR—$NH_2$ | 2173 ± 173 | 4 |
| 27 | YGGFYF—$NH_2$ | 2379 ± 568 | 3 |
| 28 | YGFFFY—$NH_2$ | 2565 ± 1246 | 4 |
| 29 | YGFFLF—$NH_2$ | 2923 ± 1054 | 4 |
| 30 | YGFFYF—$NH_2$ | 3276 ± 1519 | 4 |
| 31 | YGFFFF—$NH_2$ | 42464 ± 18796 | 4 |

Comparison of the above sequences and their $IC_{50}$ values with the sequence for the two enkephalins shows that the five amino-terminal residues of synthetic oligopeptides prepared based upon the results obtained using the scanning SPCL processs discussed above that exhibited the lowest $IC_{50}$ values were the same as the residues of the native donor molecules. In addition, a new 5-position residue (Tyr) was determined whose presence in a 6-mer sequence provided similar binding to that observed by a natural sequence.

B. N-Ac C-Amide Sets

A study similar to that above was carried out using N-Ac C-amide oligopeptide sets. Here, one residue, Arg, present at position 1 exhibited enhanced binding ($IC_{50}$=41 µM), the next most avid residue was Phe, whose binding was similar to Lys [$IC_{50}$=297 and 312 µM, respectively]. Position 2 was similarly defined by a single residue, Phe [$IC_{50}$=126 µM]. Methionine, Leu, Phe and Tyr exhibited enhanced bindings within about a factor of two of each other when at the 3-position of the sequence [$IC_{50}$=80, 112, 140 and 162, respectively]. Position 4 showed generally similar $IC_{50}$ values for each of the 18 residues, with Phe, Tyr, Arg, Ala, Leu, Asn, Gly and Lys being best and within a factor of two of the best, Phe and Tyr. Position 5 of the sequence was defined by Phe [$IC_{50}$=79 µM]. Position 6 had maximal binding with a Phe residue, followed by Arg, Tyr and Leu [$IC_{50}$=94, 129, 156 and 194, respectively].

The enhanced binding sequence defined by this study are therefore

Ac-ArgPheX$_3$aaX$_4$aaPheX$_6$aa-$NH_2$ (SEQ ID NO:32)

wherein

X$_3$aa is Met, Leu, Phe or Tyr (Met being preferred);

X$_4$aa is Phe, Tyr, Arg, Ala, Leu, Asn, Gly or Lys (Phe and Tyr being preferred); and X$_6$aa is Phe, Arg, Tyr or Leu ( Phe being preferred).

Thus, out of the 64 million possible 6-mers, the above process narrowed the field to two preferred sequences, using Met and Phe at positions 3 and 6 and Tyr or Phe at position 4, or about 128 (4×8×4) sequences when binding within about a factor of two for the optimal binding residues are considered.

The two types of oligopeptide sets produced different specific results. Nevertheless, both types of sets showed a binding preference for Phe with a Met or Leu at an adjacent position to the C-terminal side of the Phe residue as are present within the two natural enkephalins. The binding preference for an oligopeptide having a PheLeu or PheMet sequence appeared at two positions of a peptide of SEQ ID NO:32; i.e., at positions 2 and 3, and again at positions 5 and 6, albeit the 5 and 6 position preference was much smaller.

Sets of N-acetyl C-amide peptides were also constructed as described in WO 92/09300. Three sequences that exhibited $IC_{50}$ values of less than 100 nM were determined. Those sequences, and their $IC_{50}$ values were:

| SEQ ID NO: | Peptide | $IC_{50}$ Value (nM) |
|---|---|---|
| 34 | Ac—ArgPheMetTrpMetX$_6$aa—$NH_2$ | 30 |
| 35 | Ac—ArgPheMetTrpValX$_6$aa—$NH_2$ | 54 |
| 36 | Ac—ArgPheMetTrpGlnX$_6$aa—$NH_2$ | 83 | wherein X$_6$aa was an equimolar mixture of the 18 residues used for the mixed positions.

The twenty sequences corresponding to SEQ ID NO:34 (including Cys and Trp) were then synthesized and assayed along with the SEQ ID NO:34 set of mixed peptides. The results of those assays are shown below, using single letter code, and X as a mixture position.

| SEQ ID NO: | Peptide | $IC_{50}$ Value (nM) |
|---|---|---|
| 38 | Ac—RFMWMT—$NH_2$ | 4 |
| 39 | Ac—RFMWMR—$NH_2$ | 5 |
| 40 | Ac—RFMWMG—$NH_2$ | 6 |
| 41 | Ac—RFMWMK—$NH_2$ | 6 |
| 42 | Ac—RFMWMS—$NH_2$ | 7 |
| 43 | Ac—RFMWML—$NH_2$ | 11 |
| 44 | Ac—RFMWMN—$NH_2$ | 14 |
| 45 | Ac—RFMWMA—$NH_2$ | 15 |
| 46 | Ac—RFMWMM—$NH_2$ | 18 |
| 34 | Ac—RFMWMX—$NH_2$ | 19 |
| 47 | Ac—RFMWMY—$NH_2$ | 21 |
| 48 | Ac—RFMWMH—$NH_2$ | 21 |
| 49 | Ac—RFMWMQ—$NH_2$ | 22 |
| 50 | Ac—RFMWMP—$NH_2$ | 24 |
| 51 | Ac—RFMWMV—$NH_2$ | 27 |
| 52 | Ac—RFMWMW—$NH_2$ | 43 |
| 53 | Ac—RFMWMF—$NH_2$ | 58 |
| 54 | Ac—RFMWMC—$NH_2$ | 65 |
| 55 | Ac—RFMWMI—$NH_2$ | 71 |
| 56 | Ac—RFMWME—$NH_2$ | 82 |
| 57 | Ac—RFMWMD—$NH_2$ | 83 |

As is seen from the above data, the N-acetyl C-amide 6-mers having Thr, Arg, Gly, Lys, Ser. Leu, Asn, Ala and Met (SEQ ID NOS:38–46) exhibited better binding than did the 6-mer having a mixture of residues at position 6; i.e. SEQ ID NO:34.

The above assays were carried out using opioid receptors from rat brains prepared as follows. Particulate membranes were prepared using a modification of the method described by Pasternak et al., Mol. Pharm., 11:340–351 (1975). Rat brains frozen in liquid nitrogen were obtained from Rockland Inc. (Gilbertsville, Pa.). The brains were thawed, the cerebella were removed, and the remaining tissue was weighed. Each brain was individually homogenized in 40 ml Tris-HCl buffer (50 mM, pH 7.4, 4° C.) and centrigued (Sorvall RC5C SA-600 16000 rpm) for ten minutes. The pellets were resuspended in fresh Tris-HCl Buffer and incubated at 37° C. for 40 minutes. Following incubation, the suspensions were centrifuged as before, the resulting pellets were resuspended in 100 volumes of Tris buffer, and the suspensions combined. Membrane suspensions were prepared and used in the same day. Protein content of the crude homogenates ranged from 0.15–0.2 mg/ml as determined using the method described by Bradford, *Anal. Biochem.*, 72:248–254 (1976).

Binding assays were carried out in polypropylene tubes. Each tube contained 0.5 ml of membrane suspension, 8 nM of [$^3$H]-[D-Ala$^2$,MePhe$^4$,Gly-Ol$^5$]enkephalin (DAGO) (specific activity=36 Ci/mmole, 160,000 cpm/tube; obtained from Multiple Peptide Systems, Inc., San Diego, Calif. through NIDA drug distribution program 271-90-7302), and 10 mg/ml of peptide mixture and Tris-HCl buffer in a total volume of 0.65 ml. Assay tubes were incubated for 60 minutes at 25° C. The reaction was terminated by filtration through GF-B filters on a Tomtec harvester (Orange, Conn.). The filters were subsequently washed with 6 ml of Tris-HCl buffer, 4° C. Bound radioactivity was counted on an LKB Beta-plate Liquid Scintillation Counter and expressed in counts per minute (cpm). To determine inter- and intra-assay assay variation, standard curves in which [$^3$H]-DAGO was incubated in the presence of a range of concentrations of unlabeled DAGO (0.13–3900 nM) were included in each plate of each assay (a 96-well format was used). Competitive inhibition assays were performed as above using serial dilutions of the peptide mixtures. IC$_{50}$ values (the concentration necessary to inhibit 50 percent of [$^3$H]-DAGO binding) were then calculated. These were found to be consistent in three separate determinations.

EXAMPLE 6

Inhibition of Melittin Hemolysis

Melittin, a 26-mer polypeptide, is the predominant polypeptide isolated from honeybee venom (*Apis mellifera*). The amino acid residue sequence of melittin is GlyIleGlyAlaValLeuLysValLeuThrThrGly-LeuProAlaLeuIleSer-TrpIleLysArgLysArgGlnGln [SEQ ID NO:58].

Among the several physiological effects of this venom is the lysis of red blood cells (RBCs), or hemolysis. The scanning SPCL assay method was used to identify potential optimal binding sequences for N-acetyl C-amide 6-mer mixture sets prepared as discussed in Example 2. The results of those hemolytic assays are shown in the tables below for each individual predetermined residue at positions 1–6 from the N-terminus as a percentage of melittin lysis inhibited (Inhib.). Data are shown only for those residues at the named, predetermined positions where the percent lysis inhibition was within a factor of two of that of the best residue. Details of the assay procedures used are provided hereinafter.

| Residue | % Inhib. | Residue | % Inhib. |
|---|---|---|---|
| Position-1 | | Position-2 | |
| Val | 41 | Ile | 49 |
| Trp | 36 | Met | 34 |
| Ile | 32 | His | 30 |
| Gln | 32 | Gln | 30 |
| Tyr | 31 | Ser | 28 |
| Met | 31 | Ala | 28 |
| Leu | 30 | Gly | 27 |
| Glu | 28 | Thr | 27 |
| Asn | 28 | Leu | 26 |
| Phe | 27 | Val | 25 |
| Asp | 26 | | |
| Pro | 24 | | |
| Position-3 | | Position-4 | |
| Val | 41 | Ile | 46 |
| Gln | 41 | Gln | 44 |
| Leu | 37 | Val | 42 |
| Asn | 34 | Leu | 42 |
| Phe | 33 | His | 35 |
| Met | 31 | Tyr | 35 |
| Tyr | 29 | Ala | 35 |
| Pro | 26 | Ser | 30 |
| Glu | 26 | Met | 29 |
| Lys | 25 | Phe | 28 |
| Ala | 23 | Gly | 28 |
| Ile | 23 | Glu | 28 |
| His | 22 | Thr | 25 |
| Gly | 22 | Asp | 25 |
| | | Lys | 24 |
| | | Pro | 24 |
| | | Asn | 23 |
| Position-5 | | Position-6 | |
| Ile | 78 | Ile | 46 |
| Phe | 51 | Val | 45 |
| Val | 47 | Leu | 37 |
| Pro | 44 | Ser | 36 |
| Tyr | 42 | Met | 33 |
| | | Thr | 33 |
| | | Phe | 30 |
| | | Asp | 30 |
| | | Gln | 29 |
| | | His | 29 |
| | | Asn | 29 |
| | | Ala | 27 |
| | | Tyr | 25 |
| | | Glu | 24 |
| | | Gly | 23 |

As can be seen from the above data, most of the residues at each position produced similar results. However, several generalities are also apparent. A strong preference for Ile and Val residues can be seen from the appearance of one or both of those two residues near the top of each list. The residues Gln and Leu are also present near the top of each list, typically below Ile and/or Val. Contrarily, the basic residues Lys and Arg are generally not shown above, indicating a strong preference against their presence. An almost as strong contraindication can be noted for Ser and Pro, with Thr appearing near the bottom for several positions.

Several 6-mer N-acetyl C-amide peptides were prepared based upon the above results. Those peptides are shown below in single letter code along with their IC$_{50}$ values in micrograms per milliliter (µg/ml) and SEQ ID NOs.

| SEQ ID NO: | Peptide | IC$_{50}$ Value (µg/ml) |
|---|---|---|
| 60 | Ac—WIQIFI—NH$_2$ | 12 |
| 61 | Ac—VIQQFV—NH$_2$ | 16 |
| 62 | Ac—VIVIII—NH$_2$ | 50 |
| 63 | Ac—VILVFV—NH$_2$ | 58 |
| 64 | Ac—WMLVIC—NH$_2$ | 83 |
| 65 | Ac—IVDQII—NH$_2$ | 85 |
| 66 | Ac—VIMQCV—NH$_2$ | 193 |

Of the above, those of SEQ ID NOS:60–63 are particularly preferred.

The method of WO 92/09300 was then used to prepare alternate sets of 6-mer N-acetyl C-amide melittin-inhibiting peptides. Cysteine and tryptophan were not used in the mixture positions but were present at the "O" positions and proved useful in the inhibiting sequences.

Initial results provided two 6-mers having identical residues at positions 1–3, Ac-IleValIle, and either Phe or Cys at position 4. Extension of the resulting two groups provided 6-mers of the sequences shown below in single letter code along with their $IC_{50}$ values in units of micrograms per milliliter (µg/ml) and SEQ ID NOs, wherein X is an equimolar mixture of 18 amino acid residues as noted before.

| SEQ ID NO: | Peptide | $IC_{50}$ Value (µg/ml) |
|---|---|---|
| 67 | Ac—IVICLX—NH$_2$ | 16 |
| 68 | Ac—IVICFX—NH$_2$ | 17 |
| 69 | Ac—IVICMX—NH$_2$ | 20 |
| 70 | Ac—IVICQX—NH$_2$ | 21 |
| 71 | Ac—IVICVX—NH$_2$ | 22 |
| 72 | Ac—IVICPX—NH$_2$ | 23 |
| 73 | Ac—IVICNX—NH$_2$ | 24 |
| 74 | Ac—IVICDX—NH$_2$ | 28 |
| 75 | Ac—IVICSX—NH$_2$ | 32 |
| 76 | Ac—IVIFFX—NH$_2$ | 22 |
| 77 | Ac—IVIFAX—NH$_2$ | 30 |
| 78 | Ac—IVIFGX—NH$_2$ | 31 |
| 79 | Ac—IVIFDX—NH$_2$ | 32 |

Two sequences from each group, $X_4$aa=Cys with $X_5$aa=Gln or Val, and Xaa=Phe with $X_5$aa-Ala or Asp were selected for expansion to define the sixth position. Groups of resulting, particularly preferred sequences are shown below in single letter code along with their $IC_{50}$ values units of micrograms per milliliter (µg/ml) and SEQ ID NOs.

| SEQ ID NO: | Peptide | $IC_{50}$ Value (µg/ml) |
|---|---|---|
| 80 | Ac—IVICQQ—NH$_2$ | 10 |
| 81 | Ac—IVICQD—NH$_2$ | 13 |
| 82 | Ac—IVICQN—NH$_2$ | 16 |
| 83 | Ac—IVICQM—NH$_2$ | 17 |
| 84 | Ac—IVICQY—NH$_2$ | 19 |
| 85 | Ac—IVICQT—NH$_2$ | 20 |
| 86 | Ac—IVICQS—NH$_2$ | 20 |
| 87 | Ac—IVICVE—NH$_2$ | 8 |
| 88 | Ac—IVICVD—NH$_2$ | 9 |
| 89 | Ac—IVICVM—NH$_2$ | 9 |
| 90 | Ac—IVICVT—NH$_2$ | 9 |
| 91 | Ac—IVICVW—NH$_2$ | 9 |
| 92 | Ac—IVICVY—NH$_2$ | 11 |
| 93 | Ac—IVICVV—NH$_2$ | 12 |
| 94 | Ac—IVICVP—NH$_2$ | 16 |
| 95 | Ac—IVICVS—NH$_2$ | 16 |
| 96 | Ac—IVICVC—NH$_2$ | 16 |
| 97 | Ac—IVICVN—NH$_2$ | 16 |
| 98 | Ac—IVIFAE—NH$_2$ | 18 |
| 99 | Ac—IVIFAW—NH$_2$ | 22 |
| 100 | Ac—IVIFAT—NH$_2$ | 29 |
| 101 | Ac—IVIFAF—NH$_2$ | 29 |
| 102 | Ac—IVIFAG—NH$_2$ | 30 |
| 103 | Ac—IVIFAD—NH$_2$ | 31 |
| 104 | Ac—IVIFAY—NH$_2$ | 31 |
| 105 | Ac—IVIFDC—NH$_2$ | 11 |
| 106 | Ac—IVIFDW—NH$_2$ | 18 |
| 107 | Ac—IVIFDF—NH$_2$ | 21 |
| 108 | Ac—IVIFDV—NH$_2$ | 26 |
| 109 | Ac—IVIFDL—NH$_2$ | 28 |
| 110 | Ac—IVIFDA—NH$_2$ | 34 |

It is noted that Arg and Lys provided the poorest or among the poorest results for inhibition when at positions 4, 5 or 6 of the above-prepared peptides. The contraindication for Ser, Thr and Pro seen in the scanning SPCL study was also noted in this group of studies at several positions along the peptide chain. The above results can be represented as a peptide of SEQ ID NO:59, as follows:

Ac-IleValIleX$_4$aaX$_5$aaX$_6$aa-NH$_2$ wherein X$_4$aa is Phe or Cys;

X$_5$aa is Phe, Ala, Gly or Asp when X$_4$aa is Phe, and Leu, Phe, Met, Gln, Val, Pro, Asn or Asp when X$_4$aa is Cys; and X$_6$aa is Glu, Trp, Thr, Phe, Gly, Asp, Tyr, Cys, Val, Leu or Ala when X$_4$aa is Phe, and Gln, Asp, Asn, Met, Tyr, Thr, Ser, Glu, Trp, Val, Pro or Cys when X$_4$aa is Cys.

Two particularly preferred N-acetyl C-amide 6-mer sequences are obtained from the above data. Those sequences are (1)

Ac-IleValIleCysX$_5$aaX$_6$aa-NH$_2$ [SEQ ID NO:111]

wherein

X$_5$aa is Gln or Val; and

X$_6$aa is Gln, Asp, Asn, Met, Tyr, Thr or Ser when X$_5$aa is Gln, and Glu, Asp, Met, Thr, Trp, Tyr, Val, Pro, Ser, Cys or Asn when X$_5$aa is Val; and (2)

Ac-IleValIlePheX$_5$aaX$_6$aa-NH$_2$ [SEQ ID NO:112]

wherein

X$_5$aa is Ala or Asp; and

X$_6$aa is Glu, Trp, Thr, Phe, Gly, Asp or Tyr when X$_5$aa is Ala, and Cys, Trp, Phe, Val, Leu or Ala when X$_5$aa is Asp.

Each assay was carried out in 96-well culture tissue plates. Four wells per plate contained 125 µl of the non-peptide control surfactant Triton® X-100 (1 percent in deionized water), and four wells per plate contained 125 µl of a control blank of phosphate buffered saline (PBS; 35 mM phosphate buffer, 0.15M NaCl, pH 7.0). The hemolytic peptide, melittin, was used as a comparative control. The controls served to detect possible contamination and to calculate the percent inhibition of each peptide.

Human red blood cells (RBCs) were stored in heparin at 4° C. RBC were washed with PBS and centrifuged to separate them from the serum. RBCs were then resuspended in PBS to a final suspension of 0.5 percent RBCs.

Peptides were added to the plate in duplicate and in 60 µl increments (5 µl of 10× PBS was added to salinate the aqueous peptides). The concentration of peptide necessary to inhibit 50 percent of the lysis of RBCs by melittin (IC$_{50}$), was determined by performing a serial two-fold dilution of the peptide ranging from 1000 ηg/ml to 3.91 µg/ml.

After peptides were prepared in the proper dilutions on the plate, 60 µl of a 30 µg/ml melittin solution in PBS were added to all wells containing peptide. 125 Microliters of the RBC suspension were added to all the wells and the plates were incubated at 37° C. for one hour after a gentle shaking. The samples were then centrifuged at 2800 rpm for five minutes and the release of hemoglobin resulting from the cell lysis was determined by measuring the optical density (OD) at 414 nm of 100 µl of the supernatant. Zero hemolyses (blank) and 100 percent hemolysis controls were determined using a centrifugate of human RBC suspended in PBS or one percent Triton® X-100, respectively.

EXAMPLE 7

Synthesis of Peptide Mixtures on Cotton Carriers

Twenty discs cut out of commercially available cotton fabric (diameter 4.7 cm) were shaken for 15 minutes in 50 ml of dichloromethane (DCM) containing 25 percent trifluoroacetic acid (TFA). The discs were then taken out and placed into a flat ceramic funnel with the same diameter as the cotton discs. The funnel was placed on top of an 1000 ml suction flask with an outlet to a vacuum pump. The 25 percent TFA/DCM was removed from the cotton discs into the suction flask under reduced pressure. The cotton discs were then washed with DCM (2×10 ml), DCM containing 5 percent DIEA (2×10 ml) and DCM (2×10 ml) again. The washings were done by adding the wash solution to the funnel holding the cotton discs and removal of the solvent with a vacuum pump. After the last wash the cotton discs were removed and air dried. All manipulations were at room temperature unless otherwise stated.

A. Manual Synthesis

Fmoc-Glycine (1.118 g, 4 mmol), N-hydroxybenztriazole (HOBt) (540 mg, 4 mmol), N-methylimidazole (NMI) (656 µl, 8 mmol) and DIPCDI (626µ, 4 mmol) were dissolved in 6.7 ml DMF. This corresponds to a 0.5M Fmoc-Gly/HOBt/DIPCDI, 1M NMI solution. The cotton discs were soaked with this solution in a 20 ml scintillation vial and maintained for three hours. After transferring the discs to the ceramic funnel, the cotton carriers were washed with DMF (3×10 ml) and DCM (2×10 ml) as described above. This procedure was repeated once more identically.

The general peptide mixture and single, predetermined peptide coupling procedure was as follows:

1. Fmoc-deprotection: 20 percent piperidine/DMF, 15 minutes.
2. Wash: 3× DMF, 3× DCM.
3. Coupling: 0.3M Fmoc-amino acid/HOBt/DIC in DMF, 90 minutes–two hours.
4. Wash: 3× DMF, 2× DCM.

More specifically, the twenty cotton discs, placed into the ceramic funnel, were soaked with 10 ml 20 percent piperidine/DMF, and maintained for 15 minutes. After removing the 20 percent piperidine/DMF, the cotton discs were washed with DMF (3×10 ml) and DCM (2×10 ml) as described above.

(a) Coupling of the same amino acid to all cotton discs

The Fmoc-amino acid to be coupled (2.4 mmol), HOBt (324 mg, 2.4 mmol) and DIPCDI (380 µl, 2.4 mmol) were dissolved in 7.6 ml DMF. This corresponds to a 0.3M Fmoc-amino acid/HOBt/DIC solution. The cotton discs were soaked with this solution in a 20 ml scintillation vial and maintained for 90 minutes. After transferring the discs to the ceramic funnel, the coupling solution was removed, and the cotton carriers were washed with DMF and DCM, as before.

(b) Coupling of another amino acid to each cotton disc (O-coupling)

The 20 natural amino acids (0.12 mmol each) were separately dissolved in 0.4 ml of a 0.3M solution of HOBt and DIPCDI in DMF (324 mg HOBt and 380 µl DIPCDI dissolved in 7.6 ml DMF). The cotton discs were labeled as to amino acid identify with the letters A through Y, soaked with the amino acid solution, labeled with the letter of the amino acid of the solution, and maintained for 90 minutes. After transferring the discs to the ceramic funnel, the cotton discs were washed with DMF and DCM, as before.

(c) Coupling of the amino acid mixture (X-coupling)

A 0.3M solution of the 20 natural amino acids except Cys in the molar ratio of Table 2 and HOBt in DMF was prepared and aliquoted. The aliquots (7.6 ml each) were stored at −20° C. Before the coupling, the mixture aliquot was warmed up to room temperature, followed by addition of 380 µl DIPCDI. After 20 minutes (preactivation), the 19 cotton discs were soaked with this solution and maintained for two hours. After transferring them to the ceramic funnel, the cotton discs were washed with DMF and DCM, as before.

After coupling of the last (N-terminal) amino acid or mixture, the cotton discs were Fmoc-deprotected and washed. The deprotected cotton discs were soaked with 8 ml of a mixture of acetic anhydride/pyridine/DMF 1:2:3 (v/v/v) and maintained for 60 minutes. After transferring them to the ceramic funnel, the cotton discs were washed with DMF and DCM.

The acetylated cotton discs were placed into a bottle containing 30 ml 50 percent TFA, 5 percent triisobutylsilane in DCM and maintained for two hours. After pouring off the solution, 100 ml DCM were added and the bottle shaken for two minutes. This wash was repeated twice with DCM, then three times with 5 percent DIEA/DCM and again three times with DCM. The cotton discs were taken out, blotted between layers of filter paper and air dried. The dry cotton discs were cut into small discs (diameter 7 mm) with an ordinary hole puncher, labeled and refrigerated.

B. Machine Synthesis

The synthesis was done as described in U.S. Pat. No. 5,202,418, whose disclosures are incorporated by reference, and above. The essential difference between the manual synthesis of peptide mixtures and the synthesis of individual peptides on the synthesizer machine is the following: The manually prepared mixtures were synthesized directly on the glycine-cotton. Upon alkaline hydrolysis of the glycine-cotton ester, the cotton-cleaved peptides therefore contained an additional C-terminal Gly residue. In case of the synthesis of individual peptides on the machine synthesizer, a TFA-cleavable linker, in this case N-f-Moc-2,4-dimethoxy-4'-(carboxymethyloxy)-benzhydrylamine for the synthesis of peptide amides, was coupled onto the amino group of the glycine-cotton ester. After Fmoc-deprotection of the linker, the first amino acid of the peptide was coupled to the amino group of the linker. Upon cleavage of the peptides with TFA, simultaneously with the deprotection of side chains, the peptide amides are formed, with the linker and the glycine remaining bound to the cotton.

EXAMPLE 8

Preparation of Trypsin Inhibitors

Oligopeptides were prepared by the manual and machine procedures described in Example 7, using Fmoc amino protecting groups and 19 amino acids in each mixture.

Two sets of five sets of 4× N-acetyl C-amide sets were first prepared having a Lys or Arg adjacent to the single, predetermined residue (O) at each possible position along the chain, and a Gly at the C-terminus as a free acid. Trypsin is known to cleave at the C-terminal side of Lys or Arg residue, so one or the other of those residues was included in each set of sets.

By placing the Lys-O or Arg-O dipeptide from N-terminus to C-terminus, it was found that the dipeptide LysIle at positions 2 and 3 or 3 and 4 provided the best inhibitions with these 4× sets. No significant inhibition was found with Arg-O at any positions.

With the positions of the LysIle groups within the peptide sequence in hand, the remaining positions were identified using a process described in WO 92/09300 by first identifying the best residues on the N-terminal side of the dipeptide LysIle group.

The best binding 6-mer sequence was determined by repeatedly identifying best-inhibitory adjacent residues on one side of the LysIle group and then the other, with the other positions being mixtures of 19 residues, until the final, C-terminal position was determined. Five peptides that inhibited trypsin were thus identified and had the following sequences in single letter code. $IC_{50}$ Values in units of micromolarity (μM) and SEQ ID NOs are shown for those five peptides that were prepared using the mechanical synthesis process.

| SEQ ID NO: | Peptide | $IC_{50}$ Value (μM) |
|---|---|---|
| 114 | Ac—AKIYRP—NH$_2$ | 46 |
| 115 | Ac—AKIYRE—NH$_2$ | 108 |
| 116 | Ac—AKIYRD—NH$_2$ | 122 |
| 117 | Ac—MTKIFT—NH$_2$ | 133 |
| 118 | Ac—TTKIFT—NH$_2$ | 164 |

Bovine pancreatic trypsin inhibitor, a 8-residue polypeptide, exhibits an $IC_{50}$ value of about 82 nM under similar conditions. It was therefore decided to extend the peptide of SEQ ID NO:114 to 12 residues to determine if better inhibition could be obtained.

This extension was accomplished by placing equimolar mixtures, X's, on either side of the above 6-mer of SEQ ID NO:114, so that that 6-mer occupied core positions 4–9 of the new peptide sets. Position 10 was first scanned and Asp was found to be the best inhibiting residue. Position 3 was then scanned, and Gly was found best. Lys was found best at position 11 and Tyr was best at position 2. Met was best at position 12, with another Tyr being best a position 1. The resulting N-acetyl C-amide 12-mer had the sequence Ac-TyrTyrGlyAlaLysIleTyrArgProAspLysMet-NH$_2$ [SEQ ID NO:119]

The peptide of SEQ ID NO:119 exhibited an $IC_{50}$ value of 10 μM, five-times better than the 6-mer.

Inhibition studies were carried out with $N^{\alpha}$-benzoyl-DL-arginine-p-nitroanilide using the decrease in absorbance at 405 nm in the presence of peptide sets as the basis of the assay. This assay was carried out as discussed in Fritz et al., *Hoppe-Seyler's Z. Physiol. Chem.*, 345:150 (1966) that was modified for performance in a 96-well plate.

Thus, small discs (7 mm in diameter; 0.5 μmoles per disc) were cut from the reacted cotton pieces and placed into the wells of the assay plates. Peptides were released form the discs by alkaline hydrolysis of the cellulose-peptide ester bond (50 μl of a 0.1N NaOH for 15 minutes). A 0.1M Tris-HCl containing 0.025M $CaCl_2$, pH 7.8 was then added (100 μl), as were 15 μl of trypsin (bovine pancreas trypsin, Type I; Sigma Chemicals T 8003; 0.05–0.5 mg/ml in 0.02N HCl) with strong agitation of the resulting solution. Strong agitation is required. The agitated solution was maintained for 30 minutes, and the above substrate was added (100 μl, 1 mg/ml in water). After 10 minutes, 150 μl were removed from each well and transferred to another well. Absorbances at 405 nm were read using a Titertek multichannel photometer after another 20 minutes had elapsed and were expressed as a percentage of the control Ac-Gly-Cotton disc value.

The peptide-linked cotton squares from the machine synthesizer were removed from the polypropylene holders they were attached to during the synthesis, and were placed separately into scintillation vials. Neat TFA containing 5 percent triisobutylsilane (2 ml) was added to each vial. After two hours, 5 ml of water were added to each vial and the vials were vortexed thoroughly. After transferring each solution into another vial, the cotton carriers were vortexed again with another 5 ml of water. The combined cleavage and wash solutions were lyophilized. The lyophilized products were suspended in 10 ml of water and extracted with 10 ml of ethyl ether (for peptides not containing methionine or cysteine) or ethyl acetate (for peptides containing methionine or cysteine). The aqueous phases were filtered through a PTFE membrane syringe filter (1 μm) and lyophilized. Solutions of the lyophilized peptides (0.5–2 mM) were prepared in water and refrigerated prior to use, but used at room temperature.

A solution of the above trypsin (0.05 mg/ml in 0.02N HCl), 35 μl of an above-prepared peptide solution and 100 μl the before-described buffer were mixed in the wells of a 96-well assay plate and incubated for 30 minutes. Then, 100 μl of a substrate solution were added. After 30 minutes, absorbances were read and expressed as a percentage of the control (well without peptide). The values obtained with different peptide concentrations were used to determine the $IC_{50}$ values.

The foregoing is intended as illustrative of the present invention but not limiting. Numerous variations and modifications may be effected without departing from the true spirit and scope of the novel concepts of the invention.

We claim:

1. A process for providing the amino acid residue sequence of an oligopeptide ligand that specifically binds to an acceptor that comprises the steps of:

(a) providing separate pluralities of sets of self-solubilizing, unsupported mixed oligopeptides, each of said pluralities having sets that consist essentially of a mixture of equimolar amounts of linear oligopeptide chains containing five to about ten amino acid residues in each chain, the members of each set having one of at least six different predetermined amino acid residues at a single, predetermined position of the oligopeptide chain, and having said at least six different amino acid residues at the same other positions of the oligopeptide chain, each set having equimolar amounts of said at least six different amino acid residues at said other positions in the oligopeptide chain, but differing from the other sets in that the identity and chain position of the one of at least six predetermined amino acid residues present at the predetermined chain position within each set is different between the sets, each plurality of sets differing from the other plurality of sets by the chain position of said one of at least six different predetermined amino acid residues, the number of sets in said separate pluralities of sets being equal to the product of the number of different amino acid residues present at said predetermined chain positions containing said one of at least six different residues times the number of different chain positions containing said one of at least six predetermined amino acid residues;

(b) separately admixing each set with said acceptor in an aqueous medium at a set concentration of about 0.1 milligrams per liter to about 100 grams per liter, separately assaying the binding of each set to said acceptor, and determining the one or more sets that provided specific binding for each different chain position, the identity and position of the amino acid residue of said each one or more sets that provided specific binding for each chain position providing the amino acid residue sequence for the ligand that specifically binds to said acceptor.

2. The process according to claim 1 wherein the positions of the oligopeptides in the set pluralities having equimolar amounts of different amino acid residues are occupied by about 15 to about 20 different amino acid residues.

3. The process according to claim 1, wherein said acceptor is an antibody or an antibody combining site-containing antibody fragment.

4. The process according to claim 1 wherein said acceptor is a cellular receptor.

5. A process for providing the amino acid residue sequence of an oligopeptide ligand that specifically binds to an acceptor that comprises the steps of:

(a) providing a plurality of sets of self-solubilizing, unsupported mixed oligopeptides in which each set consists essentially of a mixture of equimolar amounts of linear oligopeptide chains containing the same number of five to ten amino acid residues in each oligopeptide chain, the members of each set having one of at least six predetermined amino acid residues at a single, predetermined position of the oligopeptide chain, and each set having equimolar amounts of the same at least six different amino acid residues at the same other positions of the oligopeptide chain, said plurality of sets having equimolar amounts of said at least six different amino acid residues at said other positions in the oligopeptide chain but differing in that said one of at least six predetermined amino acid residues present at the predetermined chain position within each set is different between the sets;

(b) separately admixing each set from said plurality of sets with said acceptor in an aqueous medium at a concentration of about 0.1 milligrams per liter to about 100 grams per liter, separately assaying the binding of each set to said acceptor, and determining the one or more sets of the plurality of sets that provided specific binding compared to the other sets assayed;

(c) providing another plurality of sets of self-solubilizing, unsupported mixed oligopeptides in which each set consists essentially of a mixture of equimolar amounts of linear oligopeptide chains containing the same number of five to ten amino acid residues in each oligopeptide chain and having the same chain length as the first named plurality of sets, the members of each set having one of at least six predetermined amino acid residues at another single, predetermined position of the oligopeptide chain different from said first-named sets, and each set having equimolar amounts of the same at least six different amino acid residues at the same other positions of the oligopeptide chain, said other plurality of sets having equimolar amounts of said at least six different amino acid residues at said other positions in the oligopeptide chain but differing from other set pluralities in that the one of at least six predetermined amino acid residue present at the predetermined chain position within each set is different between the set pluralities;

(d) separately admixing each set from said other plurality of sets with said acceptor in an aqueous medium at a concentration of about 0.1 milligrams per liter to about 100 grams per liter, separately assaying the binding of each other set to said acceptor, and determining the one or more sets of the other plurality of sets that provided specific binding compared to the other sets assayed; and (e) repeating steps (c) and (d) using further pluralities of sets that differ from each other and the set pluralities of steps (a) and (c) by the chain position of the one of at least six predetermined amino acid residues at the predetermined chain position until at least five pluralities of sets have been assayed, the number of sets in each plurality of sets assayed being equal to the number of different amino acid residues present at the positions at which equimolar amounts are present;

wherein the identity and position of the one of at least six amino acid residues of said each one or more sets that provided specific binding so determined for each plurality of sets provides the amino acid residue sequence for said ligand that specifically binds to said acceptor.

6. The process according to claim 5 wherein the at least five pluralities of sets utilized contain said single, predetermined amino acid residues at adjacent positions in the amino acid residue sequence that is determined.

7. The process according to claim 5 wherein said acceptor is an antibody or an antibody combining site-containing antibody fragments.

8. The process according to claim 5 wherein said acceptor is a cellular receptor.

9. The process according to claim 8 wherein said cellular receptor is present in a brain cell preparation.

10. The process according to claim 5 wherein said oligopeptide sets are admixed with said acceptor in an aqueous medium at a concentration of about 1 milligram per liter to about 100 grams per liter.

11. The process according to claim 5 wherein the length of each oligopeptide of each of the plurality of sets is six amino acid residues.

12. The process according to claim 5 wherein each oligopeptide of each plurality of sets has an N-terminal $C_1$–$C_8$ acyl amide group.

13. A process for providing a six amino acid residue sequence of an oligopeptide ligand that specifically binds to an acceptor that comprises the steps of:

(a) providing six separate pluralities of sets of self-solubilizing, unsupported mixed oligopeptides, each of said pluralities having sets that consist essentially of a mixture of equimolar amounts of linear oligopeptide chains containing six amino acid residues in each chain, the members of each set having one of at least ten predetermined amino acid residues at a single, predetermined position of the oligopeptide chain, and having the same at least ten different amino acid residues at the same other positions of the oligopeptide chain, each set of a plurality of sets having equimolar amounts of at least ten different amino acid residues at said other positions in the oligopeptide chain but differing in that the one of the at least ten predetermined amino acid residues present at the predetermined chain position within each set is different between the sets, and each of the plurality of sets differing from the other pluralities of sets by the position of the one of at least ten predetermined amino acid residues in the oligopeptide chain;

(b) separately admixing each set from a first plurality of sets with said acceptor in an aqueous medium at a concentration of about 1 milligram per liter to about 100 grams per liter, separately assaying the binding of each set to said acceptor and determining the one or more sets that provided specific binding for that plurality of sets; and (c) repeating step (b) using each of the remaining pluralities of sets in place of said first plurality of sets;

wherein the identity and position of the amino acid residue of said each one or more sets that provided specific binding for each plurality of sets provides the six amino acid residue sequence for said ligand that specifically binds to said receptor.

14. The process according to claim 13 wherein the positions of the oligopeptides in the set pluralities having equimolar amounts of different amino acid residues are occupied by about 15 to about 20 different amino acid residues.

15. The process according to claim 13 wherein each oligopeptide of each plurality of sets has an N-terminal $C_1$–$C_8$ acyl amide group.

16. The process according to claim 13 wherein each oligopeptide of each plurality of sets has a C-terminal amide group.

17. The process according to claim 13 wherein each oligopeptide of each plurality of sets has an N-terminal $C_1$–$C_8$ acrylamide group and a C-terminal amide group.

* * * * *